US012270051B2

(12) United States Patent
Block et al.

(10) Patent No.: US 12,270,051 B2
(45) **Date of Patent: *Apr. 8, 2025**

(54) AMNIOTIC FLUID CELL-DERIVED EXTRACELLULAR MATRIX AND USES THEREOF

(71) Applicant: STEMBIOSYS, INC., San Antonio, TX (US)

(72) Inventors: Travis Block, San Antonio, TX (US); Edward S. Griffey, San Antonio, TX (US); Mary M. Navarro, San Antonio, TX (US)

(73) Assignee: STEMBIOSYS, INC., San Antonio, TX (US)

( * ) Notice: Subject to any disclaimer, the term of this patent is extended or adjusted under 35 U.S.C. 154(b) by 178 days.

This patent is subject to a terminal disclaimer.

(21) Appl. No.: 17/500,408

(22) Filed: Oct. 13, 2021

(65) Prior Publication Data

US 2022/0106567 A1 Apr. 7, 2022

Related U.S. Application Data

(63) Continuation of application No. 16/592,539, filed on Oct. 3, 2019, now Pat. No. 11,180,732.

(60) Provisional application No. 62/740,817, filed on Oct. 3, 2018.

(51) Int. Cl.
*C12N 5/077* (2010.01)
*C12N 5/074* (2010.01)
*C12N 5/0775* (2010.01)

(52) U.S. Cl.
CPC ......... *C12N 5/0655* (2013.01); *C12N 5/0663* (2013.01); *C12N 5/0696* (2013.01); *C12N 2533/52* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 7,311,904 B2 | 12/2007 | Hariri | |
| 8,084,023 B2 | 12/2011 | Chen et al. | |
| 9,617,511 B2 | 4/2017 | Chen | |
| 2006/0153894 A1 | 7/2006 | Ghabrial et al. | |
| 2008/0281434 A1 | 11/2008 | Schmidt et al. | |
| 2011/0091568 A1* | 4/2011 | Lipton .................. | A61Q 19/08 424/520 |
| 2011/0293667 A1 | 12/2011 | Baksh et al. | |
| 2012/0142102 A1 | 6/2012 | Chen et al. | |
| 2015/0246072 A1 | 9/2015 | Bhatia et al. | |
| 2016/0157982 A1 | 6/2016 | Matheny et al. | |
| 2017/0182216 A1 | 6/2017 | Thomas et al. | |
| 2017/0281686 A1 | 10/2017 | Zamilpa et al. | |
| 2017/0335286 A1 | 11/2017 | Zamilpa et al. | |
| 2018/0320140 A1 | 11/2018 | Block et al. | |

FOREIGN PATENT DOCUMENTS

| | | |
|---|---|---|
| WO | WO 2009/035612 | 3/2009 |
| WO | WO 2009/052132 | 4/2009 |
| WO | WO 2016/161192 | 10/2016 |
| WO | WO 2017/136786 | 8/2017 |

OTHER PUBLICATIONS

Chen et al., "Extracellular Matrix Made by Bone Marrow Cells Facilitates Expansion of Marrow-Derived mesenchymal Progenitor Cells and Prevents their Differentiation into Osteoblasts," *Journal of Bone and Mineral Research*, 2007, 22:1943-1956.

Lai et al., "Reconstitution of marrow-derived extracellular matrix ex vivo: a robust culture system for expanding large-scale highly functional human mesenchymal stem cells," *Stem Cells and Development*, 2010, 19:1095-1107.

Marinkovic, et al., "One size does not fit all: developing a cell-specific niche for in vitro study of cell behavior" *Matrix Biol.*, 2016, 54-55:426-441.

Hoynowski, et al. "Characterization and Dfferentiation of Equine Umbilical Cord-Derived Matrix cells," Biochemical and Biophysical Research Communications, 362:347-353, 2007.

Ilic, et al. "Stem Cells in Regenerative Medicine: Introduction," British Medical Bulletin, 98:117-126, 2011.

Kusuma, et al. "Decellularized Extracellular Matrices Produced from Immortal Cell Lines Derived from Different Parts of the Placenta Support Primary Mesenchymal Stem Cell Expansion," PLOS One, 1-18, 2017.

Murphy & Atala, "Amniotic Fluid Stem Cells," Perinatal Stem Cells. Second Ed. 2013 Wiley-Blackwell, p. 1-15.

Alitalo et al., "Extracellular Matrix Components Synthesized by Human Amniotic Epithelial Cells in Culture" *Cell* 1980,19, 1053-1062.

Deutsch et al., "Stem cell-synthesized extracellular matrix for bone repair" *Journal of Materials Chemistry* 2010,20, 8942-8951.

International Search Report and written opinion issued in corresponding application No. PCT/US2019/054528, dated Jan. 22, 2020.

Gosden, C M, "Amniotic Fluid Cell Types and Culture" *British Medical Bulletin* 1983, 39(4), 348-354.

International Search Report and Written Opinion issued in Corresponding PCT Application No. PCT/US2020/019311, dated Apr. 5, 2020.

Parveen et al., "Amniotic membrane as novel scaffold for human iPSC-derived cardiomyogenesis" *In Vitro Cellular & Developmental Biology—Animal* 2019,55,272-284.

(Continued)

*Primary Examiner* — Teresa E Knight

(74) *Attorney, Agent, or Firm* — Norton Rose Fulbright US LLP

(57) ABSTRACT

Disclosed is a cell-derived extracellular matrix (ECM) derived in vitro from cells isolated from amniotic fluid, and methods of use for the isolation, maintenance, and proliferation of adherent cells including stem cells, as well as for the differentiation of stem cells.

16 Claims, 10 Drawing Sheets

(56) References Cited

OTHER PUBLICATIONS

Cananzi, M et al., "CD117+ amniotic fluid stem cells", *Organogenesis*, 8(3); pp. 77-88, 2012.
Office Action issued in corresponding Japanese Patent Application No. 2021-518504, dated Sep. 6, 2024. (English Translation Provided).
Feaster, Tromondae K., et al., "Matrigel: A Methods for the Generation of Single Contracting Human-Induced Pluripotent Stem Cell-Derived Cardiomyocytes." *Circulation Research*, vol. 117, No. 12, Dec. 2015.
Herron, Todd J. et al., "Extracellular Matrix-Mediated Maturation of Human Pluripotent Stem Cell-Derived Cardiac Mono layer Structure and Electrophysiological Function." *Circ Arrhythm Electrophysiol.* 9(4); Apr. 2016.
Strauss, "Extracellular Matrix Dynamic and Fetal Membrane Rupture", *Reproductive Sciences*, 20(2); pp. 140-153, 2013.

* cited by examiner

AMNIOTIC FLUID CELL-DERIVED EXTRACELLULAR MATRIX AND USES THEREOF

CROSS REFERENCE TO RELATED APPLICATIONS

This application is a continuation of U.S. patent application Ser. No. 16/592,539 filed Oct. 3, 2019, which claims the benefit of U.S. Prov. Pat. App. No. 62/740,817 filed Oct. 3, 2018. The contents of each of the referenced applications are incorporated into the present application by reference.

FIELD OF THE INVENTION

The invention generally relates to cell-derived extracellular matrices and uses thereof including isolation, maintenance, and proliferation of mammalian cells and differentiation of stem cells.

BACKGROUND

In vitro cell culture is perhaps the most ubiquitous, important, and poorly understood aspect of all cell biology as well as the developing fields of regenerative medicine and tissue engineering. Firstly, it allows for the observation of cell behavior so that various aspects of cell function may be studied in detail. Secondly, it allows for increase in numbers of specific cell groups. For basic research, as well as many clinical applications, it is necessary to achieve large quantities of relatively rare cells from small biological samples. In vitro cell culture permits small numbers of cells to be expanded outside the body to achieve more relevant numbers. Lastly, it permits the storage of cells for later use. By expanding cell numbers in vitro, and freezing viable cells for later use, relatively small biological samples can yield cells for multiple experiments over the span of days, months, or even years.

Despite the omnipresence of cell culture, the effects that in vitro culture has on the native characteristics of the cells it is still relatively poorly understood. Many of our current practices have arisen not from deliberate thought, planning, and experimentation, but instead from chance observations. Mammalian cell culture began in the early 1900s when, in 1911, Alexis Carrel and Montrose Burrows first published an academic paper on the cultivation of mammalian tissues in vitro. They were studying the physiology and anatomy of tissues by cutting sections of mammalian tissues and placing them on microscope slides. They then noticed that some cells migrated out of the tissue onto the slide. They went on to describe techniques for culturing cells in perpetuity. It now appears that some of their observations may not have been valid, but their work paved the way for modern cell culture.

After the discovery of hematopoietic stem cells (HSCs), groups all over the world were studying (HSCs). During their culture (in suspension), it was observed that a subpopulation of bone marrow cells stuck to the bottom of the plastic flasks and began to proliferate. These cells were later recognized to be distinct from HSCs, and were eventually dubbed mesenchymal stem cells (MSCs). Because of this chance observation that lead to the discovery of MSCs, plastic adherence is still widely used as a defining attribute of MSCs and many other mammalian cell types.

The practice of culturing cells on plastic substrates is problematic because there is substantial evidence, that is now widely accepted in the literature, demonstrating the critical role of the microenvironment in regulating cell function. The microenvironment has been shown to help direct the differentiation of stem and progenitor cells, and regulate the behavior of mature cell types.

When cells are removed from their native environment to be expanded in vitro they lose important cues from their surrounding extracellular matrix or microenvironment which relay important information to the cells regarding the composition and state of their surroundings. Changes to a cell's microenvironment have a profound effect on the behavior of those cells. The current standard for isolation and expansion of most adherent cells in vitro is to place the cells in culture vessels composed of polystyrene (plastic). The polystyrene may have been treated in some manner to facilitate cell attachment and growth but the surface is, in most cases, completely foreign to the cell. In other cases, the surface may be coated with individual matrix proteins (e.g. fibronectin or collagen) or some combination of proteins. These simple substrates disregard the complexity of the native microenvironment as well as the critical role of the microenvironment in normal cell function. The cell will immediately begin to respond to this foreign environment in a manner that is much different than when the cell is in its native environment.

Five major approaches are currently employed to address this issue of culturing cells on plastic substrates:

1. Ignore the problem.—Instead of trying to achieve a desired function that matches what would be expected in vivo, a multitude of cell types can be tested in various media in order to find cells that will exhibit a specific desired function without the appropriate matrix substrate. This approach is unsophisticated and often fails to produce desired results because of the complex interplay of variables and the breadth of interactions between cells and the extracellular matrix.
2. Identify key components.—Many academic laboratories and several companies have taken the approach of considering the tissue from which cells are isolated and looking for unique elements of that tissue that may be important for cell function. Cells are then cultured on simple substrates consisting of only one or a few matrix components. This approach often fails because matrices are naturally very complex environments including over one-hundred different proteins in some cases. Cells respond just as strongly to signals they need and fail to receive, as to signals they do not need and do receive.
3. Shotgun approach—The use of protein gels like MATRIGEL™ employs a sort of shotgun approach. A gel is created that contains many different matrix proteins with the hopes that it will contain the necessary binding motifs for many different cell types. This approach may fail by providing cues that push cells in a particular direction or by failing to provide all the cues that cells are expecting.
4. Tissue-derived matrices—This is a biomimetic approach that typically involves isolating a tissue of interest from a genetically similar animal, physically disrupting or chemically digesting the tissue to obtain a solution or uniform suspension, and then coating culture vessels with the deconstructed tissue. For example, someone who wishes to culture satellite cells, might collect muscle, homogenize the tissue, and then coat a culture vessel in homogenized muscle prior to seeding the cells. This method often fails for a few key reasons. Firstly, even within a specific tissue type, the stem cell/progenitor cell niche, may be distinct from the rest of the tissue. Simply homogenizing muscle does not guarantee that an appropriate niche is being created. Secondly, the niche consists of structural and physical cues, in addition to biochemical cues. Even if many/most of the biochemical cues are present in a tissue homogenate, the structure has been destroyed, and cells may sense very different mechanical cues. Lastly, manufacturability of tissue derived matrices is dependent on availability of tissues. This affects the total amount of cell culture possible and contributes to lot-to-lot variability.

5. Cell-derived matrices—Cells in culture can be induced to secrete a matrix in their culture vessel. This matrix is the best approximation available of the in vivo niche, and can be manufactured in vitro. Cells can be induced in vitro to elaborate a matrix and then the cells can subsequently be eliminated from the matrix, for example by using non-ionizing detergent to retain structure and chemistry of the matrix. This approach has several key advantages. (1) The matrix structure can be recreated and left undisturbed. (2) The matrix can be customized based on tissue/cell type of interest. (3) The matrix can be specific to stem and progenitor cell niche. (4) The matrix can be manufactured in large quantities.

With respect to cell-derived matrices, not all cell types can be efficiently isolated and expanded on any given cell-derived matrix. In fact, pluripotent stem cells (PSCs) appear to have much different requirements for a supportive growth substrate than do other types of cells. It is known that the specific cell type used to produce a matrix will have an effect on the composition of the matrix, and therefore, the reaction of various cell types to that matrix (see Marinkovic, M. et al., One size does not fit all: developing a cell-specific niche for in vitro study of cell behavior. *Matrix Biol.* 54-55, 426-441 (2016)). Prior work disclosed in US 8,084,023 has described the production and composition of an extracellular matrix produced by bone marrow stromal or mesenchymal stem cells (see also Chen, X. et al., Extracellular Matrix Made by Bone Marrow Cells Facilitates Expansion of Marrow-Derived Mesenchymal Progenitor Cells and Prevents Their Differentiation into Osteoblasts. *Journal of Bone and Mineral Research* 22, 1943-1956 (2007) and Lai, Y. et al., Reconstitution of marrow-derived extracellular matrix ex vivo: a robust culture system for expanding large-scale highly functional human mesenchymal stem cells. *Stem cells and development* 19, 1095-107 (2010)). This bone marrow cell derived matrix has been shown to support the expansion of other MSCs but has not been effective for the attachment and growth of other types of stem cells, specifically, induced pluripotent stem cells (iPSCs). iPSCs have exhibited an expanded potential to form cells and tissues from a much broader category than MSCs. This represents a particularly interesting challenge, because the difficulty of growing a confluent monolayer of iPSCs in standard culture conditions makes it impractical to produce a cell-derived matrix from iPSCs. A major limitation of previous cell-derived matrices, is that in order to make a tissue-specific matrix (e.g., bone marrow matrix from bone marrow MSCs, adipose matrix from adipose MSCs, or endothelial matrix from hUVECs), it is necessary that the target population of cells already be capable of adhering to the starting substrate. A difficulty with iPSCs, embryonic stem cells (ES), and many other cell types is that they do not readily adhere to simple substrates.

SUMMARY OF THE INVENTION

The present invention provides a solution to at least some of the aforementioned limitations and deficiencies in the art relating to cell-derived extracellular matrices (ECMs) to support the isolation, expansion and proliferation of pluripotent stem cells (PSCs), including but not limited to induced pluripotent stem cells (iPSCs) and embryonic stem cells (ES). The solution is premised on the use of an amniotic fluid cell-derived extracellular matrix. The use of uncommitted, readily adherent, and highly proliferative perinatal cells found in amniotic fluid allows for the creation of an extracellular matrix (ECM) that surprisingly, supports adhesion, isolation, expansion, and proliferation of these PSCs. This technical achievement was not possible with the cell-derived ECMs of the prior art. Additionally, the amniotic fluid cell-derived extracellular matrix (AFC-ECM) of the present invention is effective for the isolation, expansion, and proliferation of adherent cell types including but not limited to other stem cells such as mesenchymal stem cells, somatic cells, progenitor cells, mature cells, and cells from multiple germ layers. Surprisingly, the AFC-ECM of the invention supports increased proliferation of MSCs produced by bone marrow relative to a bone marrow cell-derived ECM. Furthermore, the AFC-ECM of the invention can support differentiation of stem cells into differentiated cell types.

In one aspect of the invention, disclosed is a cell-derived extracellular matrix (ECM) derived in vitro from cells isolated from amniotic fluid. In some embodiments, the ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises fibronectin and/or an isoform thereof. In some embodiments, the cell-derived ECM does not contain any one of or all of decorin, perlecan, and collagen (III). In some embodiments, the cells isolated from amniotic fluid comprise stem cells. In some embodiments, the cell-derived ECM is decellularized. In some embodiments, the cell-derived ECM includes any one of, any combination of, or all of the components listed in Table 2 (see Example 2) and/or any variants, derivatives, or isoforms thereof listed in Table 2, preferably all of the components listed in Table 2 and/or any derivatives or isoforms thereof.

In another aspect of the invention, disclosed is method of proliferating adherent cells in culture, the method comprising culturing the adherent cells in the presence of a cell-derived extracellular matrix (ECM) in a culture media thereby proliferating the adherent cells, wherein the cell-derived ECM is derived in vitro from cells isolated from amniotic fluid. In some embodiments, the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises fibronectin and/or an isoform thereof. In some embodiments, the cell-derived ECM does not contain decorin, perlecan, or collagen (III). In some embodiments, the cells isolated from amniotic fluid comprise stem cells. In some embodiments, the cell-derived ECM is decellularized. In some embodiments, the adherent cells comprise mammalian adherent cells. In various embodiments, the adherent cells comprise stem cells, somatic cells, progenitor cells, mature cells, or cells from multiple germ layers. In some embodiments, the adherent cells comprise stem cells. In some embodiments, the stem cells are maintained in an undifferentiated state. In some embodiments, the stem cells comprise pluripotent stem cells (PSCs). In some embodiments, the PSCs comprise induced PSCs (iPSC) and/or embryonic stem cells (ES). In some embodiments, the stem cells comprise mesenchymal stem cells (MSCs). In some embodiments, the MSCs are obtained from bone marrow. In some embodiments, the adherent cells comprise progenitor cells. In some embodiments, the progenitor cells comprise endothelial progenitor cells. In some embodiments, the adherent cells comprise mature cells. In some embodiments, the mature cells comprise chondrocytes. In some embodiments, the cell-derived ECM includes any one of, any combination of, or all of the components listed in Table 2 and/or any variants, derivatives, or isoforms thereof listed in Table 2, preferably all of the components listed in Table 2 and/or any derivatives or isoforms thereof.

In another aspect of the invention, disclosed is a method of inducing differentiation of stem cells into differentiated cell types, the method comprising culturing the stem cells in the presence of a cell-derived extracellular matrix (ECM) in a differentiation media, wherein the cell-derived ECM is derived in vitro from cells isolated from amniotic fluid. In some embodiments, the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises fibronectin and/or an isoform thereof. In some embodiments, the cell-derived ECM does not contain decorin, perlecan, or collagen (III). In some embodiments, the cells isolated from amniotic fluid comprise stem cells. In some embodiments, the cell-derived ECM is decellularized. In some embodiments, the stem cells comprise pluripotent stem cells (PSCs). In some embodiments, the PSCs comprise induced PSCs (iPSC). In some embodiments, the PSCs comprise embryonic stem cells (ES). In some embodiments, the stem cells comprise mesenchymal stem cells (MSCs). In some embodiments, the MSCs are obtained from bone marrow. In some embodiments, the differentiated cell types comprise adipocytes, osteoblasts, chondrocytes, or myocytes. In some embodiments, the cell-derived ECM includes any one of, any combination of, or all of the components listed in Table 2 and/or any variants, derivatives, or isoforms thereof listed in Table 2, preferably all of the components listed in Table 2 and/or any derivatives or isoforms thereof.

In another aspect of the invention, disclosed is a method of producing a cell-derived extracellular matrix (ECM) in vitro, the method comprising:

(a) isolating cells from amniotic fluid,
(b) seeding the isolated cells onto a cell culture container or onto a cell culture container coated with a substrate,
(c) adding a culture media to the cell culture container, and
(d) culturing the cells, thereby producing a cell-derived ECM, and
(e) optionally decellularizing the cell-derived ECM.

In some embodiments, the isolated cells from the amniotic fluid comprise stem cells. In some embodiments, the substrate is fibronectin. In some embodiments, the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises fibronectin and/or an isoform thereof. In some embodiments, the cell-derived ECM does not contain decorin, perlecan, or collagen (III). In some embodiments, the cell-derived ECM includes any one of, any combination of, or all of the components listed in Table 2 and/or any variants, derivatives, or isoforms thereof listed in Table 2.

In another aspect of the invention, disclosed is an amniotic fluid cell-derived extracellular matrix (AFC-ECM) produced in vitro by the method comprising:

(a) isolating cells from amniotic fluid,
(b) seeding the isolated cells onto a cell culture container or onto a cell culture container coated with a substrate,
(c) adding a culture media to the cell culture container, and
(d) culturing the cells, thereby producing the AFC-ECM, and
(e) optionally decellularizing the AFC-ECM.

In some embodiments, the isolated cells from the amniotic fluid comprise stem cells. In some embodiments, the substrate is fibronectin. In some embodiments, the AFC-ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the AFC-ECM further comprises fibronectin and/or an isoform thereof. In some embodiments, the AFC-ECM does not contain decorin, perlecan, or collagen (III). In some embodiments, the AFC-ECM includes any one of, any combination of, or all of the components listed in Table 2 and/or any variants, derivatives, or isoforms thereof listed in Table 2.

In another aspect of the invention, disclosed is a cell-derived extracellular matrix (ECM) derived in vitro from cells isolated from an umbilical cord. In some embodiments, the cells isolated from the umbilical cord are from the cord blood and/or the Wharton's jelly.

In another aspect of the invention, disclosed is a cell-derived extracellular matrix (ECM) derived in vitro from cells isolated from placenta tissue. In some embodiments, the cells isolated from the placenta tissue are from the membrane sheets (amnion and/or chorion), the villi, and/or the blood.

Also disclosed in the context of the present invention are embodiments 1 to 53. Embodiment 1 is a cell-derived extracellular matrix (ECM) derived in vitro from cells isolated from amniotic fluid. Embodiment 2 is the cell-derived ECM of embodiment 1, wherein the ECM comprises laminin, collagen alpha-1 (XVIII), basement membrane-specific heparan sulfate proteoglycan core protein, agrin, vimentin, and collagen alpha-2 (IV), and/or isoforms thereof. Embodiment 3 is the cell-derived ECM of embodiment 2, wherein the isoform of collagen alpha-1 (XVIII) is isoform 2, and/or wherein the isoform of agrin is isoform 6. Embodiment 4 is the cell derived ECM of any one of embodiments 2 or 3, wherein the cell-derived ECM further comprises fibronectin and/or an isoform thereof. Embodiment 5 is the cell-derived ECM of any one of embodiments 1 to 4, wherein the cell-derived ECM does not contain decorin, perlecan, and/or collagen (III). Embodiment 6 is the cell-derived ECM of any one of embodiments 1 to 5, wherein the cells isolated from amniotic fluid comprise stem cells. Embodiment 7 is the cell-derived ECM of any one of embodiments 1 to 6, wherein the cell-derived ECM is decellularized.

Embodiment 8 is a method of proliferating adherent cells in culture, the method comprising culturing the adherent cells in the presence of a cell-derived extracellular matrix (ECM) in a culture media thereby proliferating the adherent cells, wherein the cell-derived ECM is derived in vitro from cells isolated from amniotic fluid. Embodiment 9 is the method of embodiment 8, wherein the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. Embodiment 10 is the method of embodiment 9, wherein the isoform of collagen alpha-1 (XVIII) is isoform 2, and/or wherein the isoform of agrin is isoform 6. Embodiment 11 is the method of any one of embodiments 9 or 10, wherein the cell-derived ECM further comprises fibronectin and/or an isoform thereof. Embodiment 12 is the method of any one of embodiments 8 to 11, wherein the cell-derived ECM does not contain decorin, perlecan, and/or collagen (III). Embodiment 13 is the method of any one of embodiments 8 to 12, wherein the cells isolated from amniotic fluid comprise stem cells. Embodiment 14 is the method of any one of embodiments 8 to 13, wherein the cell-derived ECM is decellularized prior to contact with the adherent stem cells. Embodiment 15 is the method of any one of embodiments 8 to 14, wherein the adherent cells comprise mammalian adherent cells. Embodiment 16 is the method of any one of embodiments 8 to 15, wherein the adherent cells comprise stem cells, somatic cells, progenitor cells, mature cells, or cells from multiple germ layers. Embodiment 17 is the method of embodiment 16, wherein the adherent cells comprise stem cells. Embodiment 18 is the method of embodiment 17, wherein the stem cells are maintained in an undifferentiated state. Embodiment 19 is the method any one of embodiments 17 or 18, wherein the stem cells comprise pluripotent stem cells (PSCs). Embodiment 20 is the method of embodiment 19, wherein the PSCs comprise induced PSCs (iPSC). Embodiment 21 is the method of embodiment 19, wherein the PSCs comprise embryonic stem cells (ES). Embodiment 22 is the method of any one of embodiments 17 or 18, wherein the stem cells comprise mesenchymal stem cells (MSCs). Embodiment 23 is the method of embodiment 22, wherein the MSCs are obtained from bone marrow. Embodiment 24 is the method of embodiment 16, wherein the adherent cells comprise progenitor cells. Embodiment 25 is the method of embodiment 24, wherein the progenitor cells comprise endothelial progenitor cells. Embodiment 26 is the method of embodiment 16, wherein the adherent cells comprise mature cells. Embodiment 27 is the method of embodiment 26, wherein the mature cells comprise chondrocytes.

Embodiment 28 is a method of inducing differentiation of stem cells into differentiated cell types, the method comprising culturing the stem cells in the presence of a cell-derived extracellular matrix (ECM) in a differentiation media, wherein the cell-derived ECM is derived in vitro from cells isolated from amniotic fluid. Embodiment 29 is the method of embodiment 28, wherein the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. Embodiment 30 is the method of embodiment 29, wherein the isoform of collagen alpha-1 (XVIII) is isoform 2, and/or wherein the isoform of agrin is isoform 6. Embodiment 31 is the method of any one of embodiments 29 or 30, wherein the cell-derived ECM further comprises fibronectin and/or an isoform thereof. Embodiment 32 is the method of any one of embodiments 28 to 31, wherein the cell-derived ECM does not contain decorin, perlecan, and/or collagen (III). Embodiment 33 is the method of any one of embodiments 28 to 32, wherein the cells isolated from amniotic fluid comprise stem cells. Embodiment 34 is the method of any one of embodiments 28 to 33, wherein the stem cells comprise pluripotent stem cells (PSCs). Embodiment 35 is the method of embodiment 34, wherein the PSCs comprise induced PSCs (iPSC). Embodiment 36 is the method of embodiment 34, wherein the PSCs comprise embryonic stem cells (ES). Embodiment 37 is the method of any one of embodiments 28 to 33, wherein the stem cells comprise mesenchymal stem cells (MSCs). Embodiment 38 is the method of embodiment 22, wherein the MSCs are obtained from bone marrow. Embodiment 39 is the method of any one of embodiments 37 or 38, wherein the differentiated cell types comprise adipocytes, osteoblasts, chondrocytes, or myocytes.

Embodiment 40 is a method of producing a cell-derived extracellular matrix (ECM) in vitro, the method comprising: (a) isolating cells from amniotic fluid; (b) seeding the isolated cells onto a cell culture container or onto a cell culture container coated with a substrate; (c) adding a culture media to the cell culture container; and (d) culturing the cells, thereby producing a cell-derived ECM; and (e) optionally decellularizing the cell-derived ECM. Embodiment 41 is the method of embodiment 40, wherein the isolated cells from the amniotic fluid comprise stem cells. Embodiment 42 is the method of embodiment 40 or 41, wherein the substrate is fibronectin. Embodiment 43 is the method of any one of embodiments 40 to 42, wherein the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. Embodiment 44 is the method of embodiment 43, wherein the isoform of collagen alpha-1 (XVIII) is isoform 2, and/or wherein the isoform of agrin is isoform 6. Embodiment 45 is the method of any one of embodiments 43 or 44, wherein the cell-derived ECM further comprises fibronectin and/or an isoform thereof. Embodiment 46 is the method of any one of embodiments 40 to 45, wherein the cell-derived ECM does not contain decorin, perlecan, and/or collagen (III).

Embodiment 47 is an amniotic fluid cell-derived extracellular matrix (AFC-ECM) produced in vitro by the method comprising: (a) isolating cells from amniotic fluid, (b) seeding the isolated cells onto a cell culture container or onto a cell culture container coated with a substrate, (c) adding a culture media to the cell culture container, and (d) culturing the cells, thereby producing the AFC-ECM, and (e) optionally decellularizing the AFC-ECM. Embodiment 48 is the method of embodiment 47, wherein the isolated cells from the amniotic fluid comprise stem cells. Embodiment 49 is the method of embodiment 47 or 48, wherein the substrate is fibronectin. Embodiment 50 is the method of any one of embodiments 47 to 49, wherein the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. Embodiment 51 is the method of any embodiment 50, wherein the isoform of collagen alpha-1 (XVIII) is isoform 2, and/or wherein the isoform of agrin is isoform 6. Embodiment 52 is the method of any one of embodiments 50 or 51, wherein the cell-derived ECM further comprises fibronectin and/or an isoform thereof. Embodiment 53 is the method of any one of embodiments 47 to 52, wherein the cell-derived ECM does not contain decorin, perlecan, and/or collagen (III).

The term "stem-like characteristic" or "sternness" refers a characteristic that can be observed in or associated with a stem cell. For example, one of the stem-like characteristics can be chosen from an ability of differentiating into different cell types, an ability of self-renewal, an ability of survival under certain conditions (including hypoxia conditions), an ability to resist chemotherapeutic agents, and an expression of a wide variety of markers.

The term "isoform" refers to different forms of a biomolecule or a protein. The different forms of the biomolecule or protein may be produced by a variety of processes or mechanisms. In embodiments in which the biomolecule is a protein, the isoforms may be proteins that differ in sequence by one or more amino acids. For example, the protein isoforms may be genetic alleles. Alternatively, the protein isoforms may be the products of alternate splicing, RNA editing, posttranslational processing, and the like.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the transitional phrase "consisting essentially of," in one non-limiting aspect, a basic and novel characteristic of the cell-derived extracellular matrix of the present invention is that it (1) is derived in vitro from cells isolated from amniotic fluid and (2) provides an environment that supports adhesion, isolation, expansion, and/or proliferation of PSCs.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
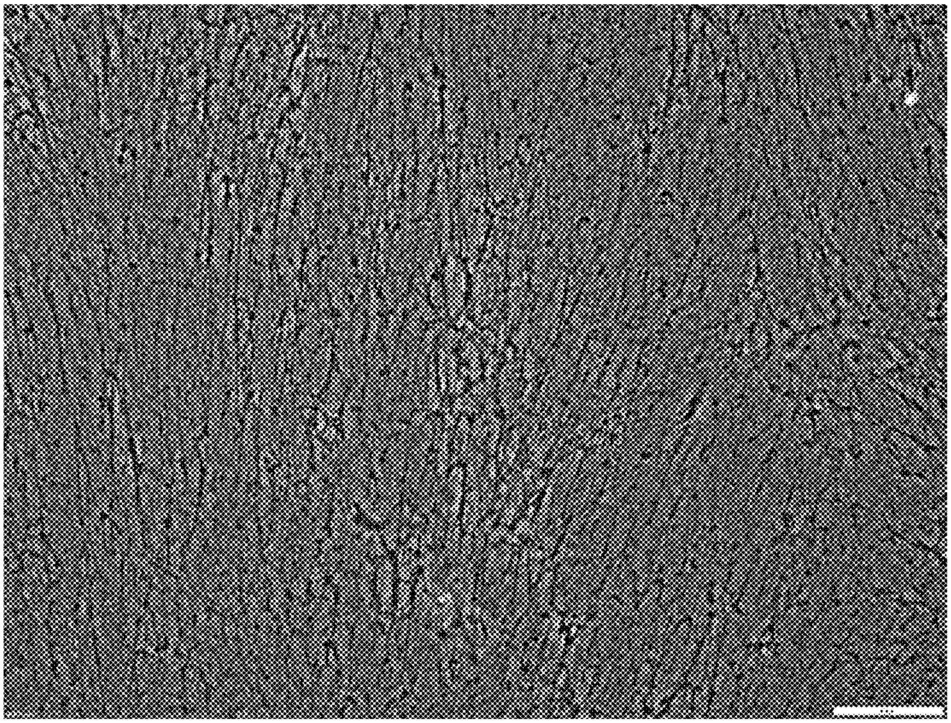
FIG. 1: a photomicrograph of a Brightfield Image of the amniotic fluid cell-derived ECM at 100× power using a 10× objective lens

The present invention discloses a cell-derived extracellular matrix (ECM) derived in vitro from cells isolated from amniotic fluid and methods of making the ECM. Also disclosed are methods of using the ECM for the isolation, maintenance, and expansion/proliferation of adherent cells which can be mammalian cells.

The function of mammalian cells is determined, largely, by the environment, e.g., an extracellular matrix, in which they reside. They react to signals that are present in their environment (positive signals) and also to signals that are required but are not present (negative signals). It is likely that uncommitted stem cells can produce a matrix that contains niche motifs necessary to maintain stem cell viability and stemness, but lack many lineage specific signals that more mature cells may secrete which would push a stem cell toward a particular fate. Without being bound by theory, it is suggested that a less mature cell, e.g., a perinatal cell or perinatal stem cell, may produce an ECM that is different from ECMs disclosed previously in the art, such as bone marrow stromal cell-derived ECMs, and may allow for better isolation and expansion/proliferation of stem cells with higher potential than mesenchymal stem cells (MSCs), such as pluripotent stem cells (PSCs). Mass spectrometry demonstrated, that compared to previously known cell-derived ECMs, the amniotic fluid cell-derived ECM of the invention contains matrix proteins found in all 3 germ layers and lacked specific proteins strongly associated with osteogenic lineages. Moreover, the ECM of the invention contained specific motifs, such as laminin, that are known to facilitate pluripotent cell adhesion and expansion.

A. Amniotic Fluid Cell-Derived Extracellular Matrix (AFC-ECM)

Perinatal cells can be divided into three groups: cells from amniotic fluid; cells from the placenta; and cells from the umbilical cord. Amniotic fluid has several sources of cells including cells derived from the developing fetus sloughed from the fetal amnion membrane, skin, and alimentary, respiratory, and urogenital tracts. Placenta also has several sources of cells including the membrane sheets (amnion and chorion), the villi, and the blood. Umbilical cord cells generally come from two sources, cord blood and Wharton's jelly. The cells from these three perinatal sources can include stem cells. The cells used to produce the amniotic fluid cell-derived ECM of the invention are obtained from the amniotic fluid of a mammal including but not limited to a human (*Homo sapiens*), murine, rabbit, cat, dog, pig, equine, or primate. In preferred embodiments, the cells are from the amniotic fluid of a human. The amniotic fluid can be sourced from humans at full-term births (greater than about 37 weeks gestational age) or pre-term births (less than about 37 weeks gestational age). Pre-term births include late pre-term births (about 33 to about 37 weeks gestational age) moderate pre-term births (about 29 to about 33 weeks gestational age), and extreme pre-term births (about 23 to about 29 weeks gestational age). The amniotic fluid can be sourced from humans prior to birth at any gestational age where amniotic fluid is present, and can be combined with sources of amniotic fluid from births. Generally, prior to birth, amniotic fluid is collected by an amniocentesis procedure. In some embodiments the amniotic fluid is sourced from humans at full-term births, at pre-term births, at late pre-term births, at moderate pre-term births, at extreme pre-term births, or prior to birth, or combinations thereof. In some embodiments, the amniotic fluid is sourced prior to birth and is collected from about 10 weeks gestational age up to birth, or from about 10 weeks to about 23 weeks gestational age, or from about 10 weeks to about 16 weeks gestational age, or from about 12 weeks gestational age up to birth, or from about 12 weeks to about 23 weeks gestational age, or from about 12 weeks to about 16 weeks gestational age. In some embodiments, the amniotic fluid sourced prior to birth is collected by an amniocentesis procedure. The cells can be obtained and isolated from amniotic fluid by techniques known in the art, such as those disclosed in Murphy et. al., Amniotic Fluid Stem Cells, *Perinatal Stem Cells*, Second Ed. 2013.

Amniotic fluid is comprised of cells having the ability to differentiate into cell types derived from all 3 embryonic germ layers (ectoderm, endoderm, mesoderm) spontaneously or as a result of treatment with specific growth factors or combinations of growth factors known to one of skill in the art. That is, a single cell has the capacity to be induced to express genes which are specific to any of the three germ layers. Amniotic fluid also contains a mixture of different cell types including cells derived from the developing fetus sloughed from the fetal amnion membrane, skin, and alimentary, respiratory, and urogenital tracts. Because of the origin of the amniotic fluid and placental membranes, these cells can maintain highly multipotent differentiation potential and comprise a cell population that contains cells of all three germ layers. The amniotic fluid cells can comprise stem cells. In some embodiments, the amniotic fluid cells are isolated stem cells. In some embodiments, the amniotic fluid cells comprise stem cells having the ability to differentiate into cell types derived from all 3 embryonic germ layers (ectoderm, endoderm, mesoderm) and/or multipotent stem cells, and/or pluripotent stem cells.

The amniotic fluid cell-derived ECM of the invention is comprised of various proteins. The proteins of the ECM can be identified by techniques known in the art and include mass spectroscopy and immunohistochemical staining. The ECM can include, but is not limited to the components listed in Table 2 (see Example 2 below) and any variants, derivatives, or isoforms thereof. The amniotic fluid-cell derived ECM can include any combination of any of the components and any variants, derivatives, or isoforms thereof from Table 2. In some embodiments, a combination can comprise, consist essentially of, or consist of: laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises, consist essentially of, or consists of fibronectin and/or an isoform thereof. In some embodiments, the amniotic fluid cell-derived ECM does not contain any one of or all of decorin, perlecan, and collagen (III). The most abundant collagens in Table 2 are collagens I, IV, and XVIII. Some noteworthy differences in proteins between the amniotic fluid cell-derived ECM of the present inventions and a bone marrow cell-derived matrix are described in Table 1.

TABLE 1

Differences Between the Amniotic Fluid Cell-Derived ECM (AFC-Matrix) and a Bone Marrow Cell-Derived Matrix (BM-Matrix)

| Protein/ Gene Code | Difference between AFC-Matrix & BM-Matrix | Physiologic Relevance |
|---|---|---|
| Laminin | 5 sub-units are abundant in AFC Matrix; Low expression in BM-Matrix | Laminin is known to support adhesion and expansion of pluripotent cells. |
| Collagen XVIII | Abundant in AFC Matrix; Absent in BM-Matrix | Important for ocular development |
| Agrin | Present in AFC Matrix; Absent in BM-Matrix | produced by motoneurons to induce aggregation of acetylcholine receptors |

TABLE 1-continued

Differences Between the Amniotic Fluid Cell-Derived ECM (AFC-Matrix) and a Bone Marrow Cell-Derived Matrix (BM-Matrix)

| Protein/ Gene Code | Difference between AFC-Matrix & BM-Matrix | Physiologic Relevance |
|---|---|---|
| Biglycan | Abundant in BM-Matrix; Low expression in AFC Matrix | Regulates bone and muscle development |
| Collagen I | Overexpressed in BM-Matrix relative to AFC Matrix | Key to fibrillar proteins; highly abundant in bone |
| Periostin | Present in BM-Matrix; Absent in AFC Matrix | Regulates mineralization; Marker of noncardiomyocyte lineage cells in heart |

The amniotic fluid cell-derived ECM (AFC-ECM) of the invention can be produced in vitro by the following process:

(a) isolating cells from amniotic fluid,
(b) seeding the isolated cells onto a cell culture container or onto a cell culture container coated with a substrate,
(c) adding a culture media to the cell culture container, and
(d) culturing the cells, thereby producing the AFC-ECM, and
(e) optionally decellularizing the AFC-ECM.

Disclosed herein is a method of producing in vitro a cell-derived extracellular matrix (ECM), the method comprising:

(a) isolating cells from amniotic fluid,
(b) seeding the isolated cells onto a cell culture container or onto a cell culture container coated with a substrate,
(c) adding a culture media to the cell culture container, and
(d) culturing the cells, thereby producing a cell-derived ECM, and
(e) optionally decellularizing the cell-derived ECM.

Disclosed herein is an amniotic fluid cell-derived extracellular matrix (AFC-ECM) produced in vitro by the method comprising:

(a) isolating cells from amniotic fluid,
(b) seeding the isolated cells onto a cell culture container or onto a cell culture container coated with a substrate,
(c) adding a culture media to the cell culture container, and
(d) culturing the cells, thereby producing the AFC-ECM, and
(e) optionally decellularizing the AFC-ECM.

Any seeding density may be used which allows cells to form a confluent monolayer immediately or after a period of time in culture. In some embodiments, the seeding density is about 10 cells/$cm^2$—about 100,000 cells/$cm^2$, or about 100 cells/$cm^2$—about 75,000 cells/$cm^2$, or about 500 cells/$cm^2$—about 50,000 cells/$cm^2$, or about 500 cells/$cm^2$—about 10,000 cells/$cm^2$, or about 500 cells/$cm^2$—about 5,000 cells/$cm^2$, or about 500 cells/$cm^2$—about 2,500 cells/$cm^2$, or about 1,000 cells/$cm^2$—about 25,000 cells/$cm^2$, or about 2,000 cells/$cm^2$—about 10,000 cells/$cm^2$, or about 3,000 cells/$cm^2$—about 5000 cells/$cm^2$.

Any type of container suitable for cultivation of cells can be used for the present invention. Examples include, but are not limited to cell culture flasks, T-flasks, stirred flasks, spinner flasks, fermenters, and bioreactors. Rocking bottles, shaking flasks, tubes, and other containers are also suitable containers when placed on a rocking platform or shaker. The cell culture container can be coated with a substrate to allow for better cell adhesion. A non-limiting example of a suitable substrate for coating the cell container is fibronectin.

Various commercially available cell culture media, e.g., alpha Minimum Essential Media (a-MEM) culture media (Thermo Fisher Scientific, Grand Island, NY), are suitable for culturing amniotic fluid cells. The commercially available culture media can be modified by adding various supplemental substances to the media, e.g. sodium bicarbonate, L-glutamine, penicillin, streptomycin, Amphotericin B and/or serum. The serum can be fetal bovine serum. The media can also be serum free. Additionally, substances such as L-ascorbic acid can be added to the media or modified media to induce cell production of an ECM.

The initial culture media can be changed and/or replaced with another media at various times during the culturing process. For example, the initial media can be a "Complete Media" and then be replaced by an "Inducing Media" during the culturing process. A non-limiting example of a "Complete Media" contains (α-MEM) plus 2 mM L-Glutamine plus antibiotic-antimycotic plus 15% Fetal Bovine Serum. A non-limiting example of an "Inducing Media" contains the "Complete Media" plus 50 mM L-Ascorbic Acid.

The culturing of the amniotic fluid cells can take place in an incubator at 37° C., 5% $CO_2$, and 90% humidity. Culturing can take place under various environmental conditions including, but not limited to normoxic, i.e., 20-21% oxygen in the atmosphere, or hypoxic conditions.

Decellularizing the amniotic fluid cell-derived ECM of the amniotic fluid cells can include removing the viable amniotic fluid cells or rendering the amniotic fluid cells non-viable. The amniotic fluid cells can be decellularized from the ECM by using methods known in the art and can include, but are not limited to lysing the amniotic fluid cells and then removing the lysed amniotic fluid cells by washing. Various substances can be used to remove the amniotic fluid cells from the ECM. Non-limiting examples include an "Extraction Buffer" containing TRITON X-100 and ammonium hydroxide in PBS buffer. After the ECM has been decellularized of amniotic fluid cells, the resulting ECM is thereby essentially cell-free or free of viable amniotic fluid cells. If feeder cells are used, then the decellularizing methods also apply to any viable feeder cells present on the ECM, thereby resulting in the ECM being essentially free or free of viable feeder cells. The decellularizing methods also apply to any viable cells present on the ECM, thereby resulting in the ECM being essentially free or free of any viable cells. Thus, a decellularized ECM means that the ECM is acellular, meaning that the ECM is free of any viable cells.

In some embodiments, the amniotic fluid cell-derived ECM is a three-dimensional (3D) ECM.

The methods described supra also apply to producing cell-derived ECMs from other perinatal cells such as cells from the umbilical cord including the cord blood and Wharton's jelly; and cells from placenta tissue including the membrane sheets (amnion and chorion), the villi and the blood.

In one embodiment, a perinatal cell-derived ECM is produced in vitro by the following process:

(a) isolating cells from an umbilical cord,
(b) seeding the isolated cells onto a cell culture container or onto a cell culture container coated with a substrate,
(c) adding a culture media to the cell culture container, and
(d) culturing the cells, thereby producing a cell-derived ECM, and
(e) optionally decellularizing the cell-derived ECM.

In some embodiments, the cells isolated from the umbilical cord are from the cord blood and/or the Wharton's jelly.

In another embodiment, a perinatal cell-derived ECM is produced in vitro by the following process:

(a) isolating cells from placenta tissue, (b) seeding the isolated cells onto a cell culture container or onto a cell culture container coated with a substrate, (c) adding a culture media to the cell culture container, and (d) culturing the cells, thereby producing a cell-derived ECM, and (e) optionally decellularizing the cell-derived ECM.

In some embodiments, the cells isolated from the placenta tissue are from the membrane sheets (amnion and/or chorion), the villi, and/or the blood.

In one aspect of the invention, disclosed is a cell-derived extracellular matrix (ECM) derived in vitro from cells isolated from an umbilical cord. In some embodiments, the cells isolated from the umbilical cord are from the cord blood and/or the Wharton's jelly.

In another aspect of the invention, disclosed is a cell-derived extracellular matrix (ECM) derived in vitro from cells isolated from placenta tissue. In some embodiments, the cells isolated from the placenta tissue are from the membrane sheets (amnion and/or chorion), the villi, and/or the blood B. Methods to Expand/Proliferate Adherent Cells Methods to expand/proliferate adherent cells include obtaining the adherent cells and culturing them in the presence of the amniotic fluid cell-derived ECM of the invention. In some embodiments, the adherent cells are mammalian adherent cells. Any seeding density may be used which allows cells to form a confluent monolayer immediately or after a period of time in culture. In some embodiments, the seeding density is about 10 cells/cm$^2$—about 100,000 cells/cm$^2$, or about 100 cells/cm$^2$—about 75,000 cells/cm$^2$, or about 500 cells/cm$^2$—about 50,000 cells/cm$^2$, or about 500 cells/cm$^2$—about 10,000 cells/cm$^2$, or about 500 cells/cm$^2$—about 5,000 cells/cm$^2$, or about 500 cells/cm$^2$—about 2,500 cells/cm$^2$, or about 1,000 cells/cm$^2$—about 25,000 cells/cm$^2$, or about 2,000 cells/cm$^2$—about 10,000 cells/cm$^2$, or about 3,000 cells/cm$^2$—about 5000 cells/cm$^2$. In various embodiments, the adherent cells are stem cells, somatic cells, progenitor cells, mature cells, and/or cells from multiple germ layers.

In some embodiments, the adherent cells are stem cells. In some embodiments, the stem cells are pluripotent stem cells (PSCs) or mesenchymal stem cells (MSCs). Pluripotent stem cells (PSCs) can self-renew and differentiate into any of the three germ layers: ectoderm, endoderm, and mesoderm, from which all tissues and organs develop. Embryonic stem cells (ES) are currently the only known natural pluripotent stem cells. Induced pluripotent stem (iPSCs) cells also are PSCs. iPSCs are derived from cells generally taken from adult tissue or adult cells, and reprogrammed to the level of embryonic stem cells. Methods for producing iPSCs are known in the art. Mesenchymal stem cells (MSCs) are multipotent stromal cells. MSCs can be obtained from the following non-limiting sources: bone marrow, umbilical cord tissue, e.g. Wharton's jelly, umbilical cord blood, adipose tissue, and amniotic fluid. In some embodiments the stem cells are maintained in an undifferentiated state and maintain their stemness.

In some embodiments, the adherent cells are somatic cells also known as vegetal cells, which are any biological cells in a multicellular organism other than reproductive cells, gametes, germ cells, gametocytes, or undifferentiated stem cells.

In some embodiments, the adherent cells are cells from multiple germ layers including cells from the ectoderm, endoderm, and/or mesoderm.

In some embodiments, the adherent cells are progenitor cells including but not limited to endothelial progenitor cells (EPCs), angioblasts, pancreatic progenitor cells, progenitor cells from the periosteum, and bone marrow stromal cells.

In some embodiments, the adherent cells are mature cells including but not limited to chondrocytes and osteoblasts.

Cell culture techniques suitable for proliferation of adherent cells in culture are known in the art and can be followed. Suitable commercially available culture media for cell proliferation includes, but is not limited to: StemMACS™ iPS-Brew XF available from Miltenyl Biotec; alpha minimum essential media (aMEM) which can be supplemented with fetal bovine serum, antibiotic-antimycotic (anti-anti), and/or GlutaMax™ available from Gibco; and Iscove's Modified Dulbecco's Medium (IMDM) which can be supplemented with fetal bovine serum, antibiotic-antimycotic (anti-anti), GlutaMax and/or growth factors such as EGF and FGF. In some embodiments, no Rock inhibitor is used. Once cells begin to approach confluence (e.g., as determined by brightfield microscopy), cells can be passaged manually, by cutting large colonies into smaller colonies and then re-plate those by physically lifting them off the dish and placing them on a fresh plate of amniotic fluid cell-derived ECM. This procedure can be repeated indefinitely. In some embodiments disclosed is a method of proliferating adherent cells in culture, the method comprising culturing the cells in the presence of a cell-derived extracellular matrix (ECM) in a culture media thereby proliferating the adherent cells, wherein the cell-derived ECM is derived in vitro from cells isolated from amniotic fluid.

The methods of expanding/proliferating adherent cells described supra also apply to the use of expanding/proliferating adherent cells in culture in the presence of other perinatal cell-derived ECMs. In some aspects, disclosed is a method of proliferating adherent cells in culture, the method comprising culturing the adherent cells in the presence of a cell-derived extracellular matrix (ECM) in a culture media thereby proliferating the adherent cells, wherein the cell-derived ECM is derived in vitro from cells isolated from an umbilical cord or placenta tissue. In some embodiments, the cells isolated from the umbilical cord are from the cord blood and/or the Wharton's jelly. In other embodiments, the cells isolated from the placenta tissue are from the membrane sheets (amnion and/or chorion), the villi, and/or the blood.

C. Methods to Induce Differentiation of Stem Cells

Disclosed herein are methods of inducing differentiation of stem cells into differentiated cell types, the method comprising culturing the stem cells in the presence of a cell-derived extracellular matrix (ECM) in a differentiation media, wherein the cell-derived ECM is derived in vitro from cells isolated from amniotic fluid, i.e. the amniotic fluid cell-derived ECM of the invention. In some embodiments, the cell-derived ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises fibronectin and/or an isoform thereof. In some embodiments, the cell-derived ECM does not contain decorin, perlecan, or collagen (III). In some embodiments, the cells isolated from amniotic fluid comprise stem cells. In some embodiments, the cell-derived ECM is decellularized. The stem cells can be pluripotent stem cells (PSCs), such as induced PSCs (iPSC) or embryonic stem cells (ES). The stem cells can be mesenchymal stem cells (MSCs). MSCs can be obtained from the following non-limiting sources: bone marrow, umbilical cord tissue, e.g. Wharton's jelly, umbilical cord blood, adipose tissue, and amniotic fluid. In some embodiments, the MSCs are obtained from bone marrow. In some embodiments, the differentiated cell types can be adipocytes, osteoblasts, chondrocytes, or myocytes.

Cell culture techniques for differentiation of stem cells into differentiated cell types are known in the art and can be followed. Various commercially available differentiation media are suitable for use and can be specific for a particular desired differentiated cell type. For example, an adipogenic differentiation media can comprise DMEM containing FBS, IBMX, dexamethasone, insulin, and/or indomethacin. Another example is an osteoblast differentiation media which can be a growth media supplemented with dexamethasone and/or L-ascorbate-2-phosphate.

The methods of inducing differentiation of stem cells described supra also apply to the use of culturing stem cells in the presence of other perinatal cell-derived ECMs in differentiation media. In some aspects, disclosed is a method of inducing differentiation of stem cells into differentiated cell types, the method comprising culturing the stem cells in the presence of a cell-derived extracellular matrix (ECM) in a differentiation media, wherein the cell-derived ECM is derived in vitro from cells isolated from an umbilical cord or placenta tissue. In some embodiments, the cells isolated from the umbilical cord are from the cord blood and/or the Wharton's jelly. In other embodiments, the cells isolated from the placenta tissue are from the membrane sheets (amnion and/or chorion), the villi, and/or the blood.

EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

A. Example 1—Production of an Amniotic Fluid Cell-Derived ECM

Four amniotic fluid cell-derived ECMs (Matrix A, Matrix B, Matrix C, and Matrix D) were made using the following procedure: cells aseptically isolated from amniotic fluid collected from full term birth (>37 weeks gestational age) from 4 donors were seeded onto fibronectin coated tissue-culture treated flasks and cultured in Complete Media at 37° C., 5% $CO_2$ and 90% RH in an incubator. The Complete Media was alpha Minimum Essential Media (aMEM) plus 2 mM L-Glutamine plus antibiotic-antimycotic plus 15% Fetal Bovine Serum.

At day 3-4, one-half of the complete medium was aspirated from the flasks and replaced with one-half of new Complete Media. The flasks were placed back into the incubator at the same conditions as stated above.

At day 7-8, the Complete Media was aspirated from the culture flasks and was replenished with Inducing Media. The flasks were placed back into the incubator at the same conditions as stated above. The Inducing Media was Complete Media plus 50 mM L-Ascorbic Acid.

At day 10-11, the Inducing Media was aspirated from the culture flasks and the ECM which had formed inside the flasks was washed one time with phosphate buffered saline (PBS). Then the PBS was aspirated from the flasks. An Extraction Buffer was added to the flasks and incubated for 7-10 minutes at RT to decellularize each ECM, then the Extraction Buffer was aspirated from the flasks. The Extraction Buffer was PBS containing 0.5% (v/v) TRITON-X100 and 20 mM ammonium hydroxide ($NH_4OH$).

Each of the decellularized ECMs in the flasks was washed three times with PBS followed by one wash with sterile water and then the sterile water was aspirated from the flasks. The four decellularized ECMs in the flasks were allowed to dry at RT and then stored at 4° C.

Figure 2:
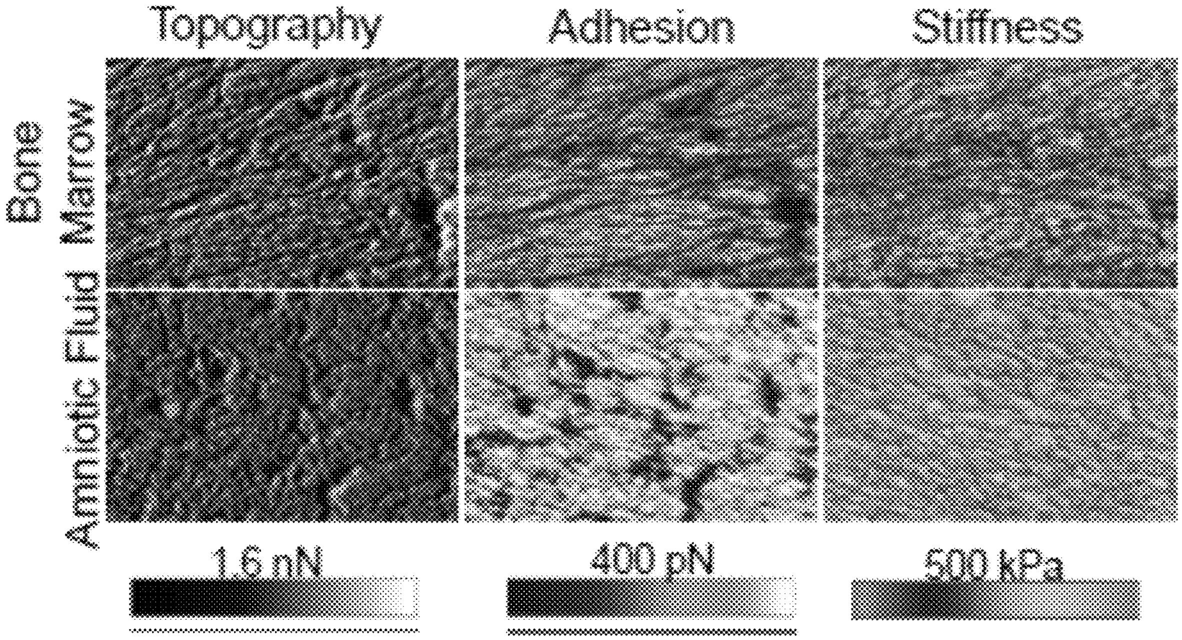
FIG. 2: an atomic force photomicrograph of 3 representative 40×40 um sections of the amniotic fluid cell-derived ECM and a bone marrow cell-derived ECM showing topography, adhesion, and stiffness.
Figure 3A:
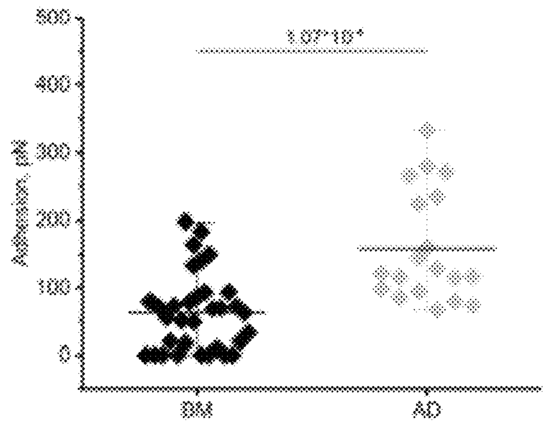
FIG. 3A: a scatter plot showing quantification of adhesion of bone marrow- and amniotic fluid-cell-derived ECMs. Each point represents an independent point of measurement.
Figure 3B:
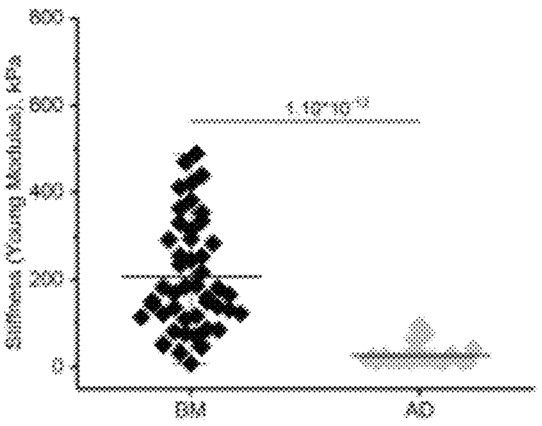
FIG. 3B: a scatter plot showing quantification of stiffness (elastic modulus) of bone marrow- and amniotic fluid-cell-derived ECMs. Each point represents an independent point of measurement.

A photomicrograph of a Brightfield Image of an amniotic fluid cell-derived ECM (Matrix B) is shown in FIG. 1 at 100× power using a 10× objective lens. An atomic force photomicrograph of 3 representative 40×40 um sections of the amniotic fluid cell-derived ECM (Matrix B) and a bone marrow cell-derived ECM showing topography, adhesion, and stiffness is shown in FIG. 2. The bone marrow- and amniotic fluid-cell-derived ECMs are structurally and physically distinct. Quantification of adhesion and stiffness (elastic modulus) of bone marrow- and amniotic fluid-cell-derived ECMs show bone marrow ECM is 10-fold stiffer, and 3-fold less adhesive, relative to amniotic fluid ECM as shown in the scatter plots in FIG. 3*a* (Adhesion) and FIG. 3*b* (Stiffness) where BM=bone marrow cell-derive ECM, AD=amniotic fluid cell-derived ECM (Matrix B). Each point represents an independent point of measurement.

B. Example 2—Composition of Amniotic Fluid Cell-Derived ECM

The composition of the each of the amniotic fluid cell-derived ECMs produced in Example 1 was determined by mass spectrometry. The components with their spectral count and molecular weight are listed in Table 2.

TABLE 2

Amniotic Fluid Cell-Derived ECM Components

| Protein | MW | Total Spectra Count<br>Matrix A | Matrix B | Matrix C | Matrix D |
|---|---|---|---|---|---|
| Isoform 7 of Fibronectin OS = *Homo sapiens* OX = 9606 GN = FN1 | 269 kDa | 817 | 13965 | 1143 | 794 |
| Isoform 3 of Fibronectin OS = *Homo sapiens* OX = 9606 GN = FN1 | 259 kDa | 807 | 13836 | 1150 | 790 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Fibronectin OS = *Homo sapiens* OX = 9606 GN = FN1 PE = 1 SV = 4 | 263 kDa | 802 | 13851 | 1138 | 781 |
| Isoform 14 of Fibronectin OS = *Homo sapiens* OX = 9606 GN = FN1 | 249 kDa | 770 | 12625 | 1103 | 763 |
| Isoform 10 of Fibronectin OS = *Homo sapiens* OX = 9606 GN = FN1 | 240 kDa | 758 | 12506 | 1082 | 746 |
| Myosin-9 OS = *Homo sapiens* OX = 9606 GN = MYH9 PE = 1 SV = 4 | 227 kDa | 564 | 3923 | 295 | 340 |
| SWISS-PROT: P60712 (Bos taurus) Actin, cytoplasmic1 | 42 kDa | 293 | 2496 | 450 | 395 |
| Vimentin OS = *Homo sapiens* OX = 9606 GN = VIM PE = 1 SV = 4 | 54 kDa | 263 | 1179 | 178 | 338 |
| Neuroblast differentiation-associated protein AHNAK OS = *Homo sapiens* OX = 9606 GN = AHNAK PE = 1 SV = 2 | 629 kDa | 250 | 803 | 17 | 184 |
| Histone H2B type 1-D OS = *Homo sapiens* OX = 9606 GN = HIST1H2BD PE = 1 SV = 2 | 14 kDa | 212 | 1121 | 176 | 187 |
| Isoform 2 of Filamin-A OS = *Homo sapiens* OX = 9606 GN = FLNA | 280 kDa | 212 | 342 | 12 | 143 |
| Basement membrane-specific heparan sulfate proteoglycan core protein OS = *Homo sapiens* OX = 9606 GN = HSPG2 PE = 1 SV = 4 | 469 kDa | 202 | 0 | 402 | 338 |
| Isoform 4 of Plectin OS = *Homo sapiens* OX = 9606 GN = PLEC | 516 kDa | 185 | 337 | 10 | 83 |
| SWISS-PROT: P02769 (Bos taurus) Bovine serum albumin precursor | 69 kDa | 122 | 112 | 53 | 72 |
| Tubulin beta chain OS = *Homo sapiens* OX = 9606 GN = TUBB PE = 1 SV = 2 | 50 kDa | 117 | 0 | 36 | 92 |
| Spectrin alpha chain, non-erythrocytic 1 OS = *Homo sapiens* OX = 9606 GN = SPTAN1 PE = 1 SV = 3 | 285 kDa | 107 | 342 | 10 | 78 |
| Tubulin beta-4B chain OS = *Homo sapiens* OX = 9606 GN = TUBB4B PE = 1 SV = 1 | 50 kDa | 107 | 0 | 34 | 84 |
| Isoform 3 of Spectrin alpha chain, non-erythrocytic 1 OS = *Homo sapiens* GN = SPTAN1 | 282 kDa | 106 | 345 | 0 | 77 |
| Histone H4 OS = *Homo sapiens* OX = 9606 GN = HIST1H4A PE = 1 SV = 2 | 11 kDa | 100 | 1257 | 91 | 96 |
| Tubulin beta-4A chain OS = *Homo sapiens* OX = 9606 GN = TUBB4A PE = 1 SV = 2 | 50 kDa | 99 | 0 | 31 | 76 |
| Protein-glutamine gamma-glutamyltransferase 2 OS = *Homo sapiens* OX = 9606 GN = TGM2 PE = 1 SV = 2 | 77 kDa | 94 | 188 | 73 | 25 |
| SWISS-PROT: P00761\|TRYP_PIG Trypsin - Sus scrofa (Pig). | 24 kDa | 94 | 362 | 121 | 96 |
| Tubulin alpha-1B chain OS = *Homo sapiens* OX = 9606 GN = TUBA1B PE = 1 SV = 1 | 50 kDa | 93 | 295 | 37 | 86 |
| Isoform 2 of Clathrin heavy chain 1 OS = *Homo sapiens* OX = 9606 GN = CLTC | 188 kDa | 92 | 97 | 1 | 15 |
| Tubulin beta-2A chain OS = *Homo sapiens* OX = 9606 GN = TUBB2A PE = 1 SV = 1 | 50 kDa | 92 | 0 | 32 | 73 |
| Elongation factor 1-alpha 1 OS = *Homo sapiens* OX = 9606 GN = EEF1A1 PE = 1 SV = 1 | 50 kDa | 89 | 132 | 14 | 70 |
| Isoform 2 of Tubulin alpha-1A chain OS = *Homo sapiens* OX = 9606 GN = TUBA1A | 46 kDa | 88 | 305 | 34 | 82 |
| Talin-1 OS = *Homo sapiens* OX = 9606 GN = TLN1 PE = 1 SV = 3 | 270 kDa | 88 | 109 | 4 | 41 |
| Myosin-10 OS = *Homo sapiens* GN = MYH10 PE = 1 SV = 3 | 229 kDa | 84 | 417 | 56 | 46 |
| Spectrin beta chain, non-erythrocytic 1 OS = *Homo sapiens* OX = 9606 GN = SPTBN1 PE = 1 SV = 2 | 275 kDa | 84 | 260 | 7 | 61 |
| Pyruvate kinase PKM OS = *Homo sapiens* OX = 9606 GN = PKM PE = 1 SV = 4 | 58 kDa | 83 | 73 | 21 | 46 |
| Tubulin alpha-1C chain OS = *Homo sapiens* OX = 9606 GN = TUBA1C PE = 1 SV = 1 | 50 kDa | 83 | 0 | 0 | 78 |
| Major vault protein OS = *Homo sapiens* OX = 9606 GN = MVP PE = 1 SV = 4 | 99 kDa | 82 | 360 | 68 | 108 |
| Actin, aortic smooth muscle OS = *Homo sapiens* OX = 9606 GN = ACTA2 PE = 1 SV = 1 | 42 kDa | 78 | 0 | 126 | 77 |
| Actin, gamma-enteric smooth muscle OS = *Homo sapiens* OX = 9606 GN = ACTG2 PE = 1 SV = 1 | 42 kDa | 76 | 313 | 122 | 73 |
| Alpha-actinin-4 OS = *Homo sapiens* OX = 9606 GN = ACTN4 PE = 1 SV = 2 | 105 kDa | 75 | 199 | 11 | 76 |
| Isoform 8 of Filamin-B OS = *Homo sapiens* OX = 9606 GN = FLNB | 282 kDa | 75 | 123 | 2 | 94 |
| Tubulin alpha-4A chain OS = *Homo sapiens* OX = 9606 GN = TUBA4A PE = 1 SV = 1 | 50 kDa | 73 | 262 | 0 | 65 |
| Glyceraldehyde-3-phosphate dehydrogenase OS = *Homo sapiens* OX = 9606 GN = GAPDH PE = 1 SV = 3 | 36 kDa | 71 | 145 | 24 | 66 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Cytoplasmic dynein 1 heavy chain 1 OS = *Homo sapiens* OX = 9606 GN = DYNC1H1 PE = 1 SV = 5 | 532 kDa | 65 | 49 | 0 | 5 |
| Histone H2A.J OS = *Homo sapiens* OX = 9606 GN = H2AFJ PE = 1 SV = 1 | 14 kDa | 65 | 216 | 62 | 79 |
| Serpin H1 OS = *Homo sapiens* OX = 9606 GN = SERPINH1 PE = 1 SV = 2 | 46 kDa | 64 | 731 | 128 | 97 |
| Histone H2A type 2-C OS = *Homo sapiens* OX = 9606 GN = HIST2H2AC PE = 1 SV = 4 | 14 kDa | 63 | 0 | 61 | 82 |
| Alpha-actinin-1 OS = *Homo sapiens* GN = ACTN1PE = 1 SV = 2 | 103 kDa | 62 | 217 | 19 | 77 |
| Histone H2AX OS = *Homo sapiens* OX = 9606 GN = H2AFX PE = 1 SV = 2 | 15 kDa | 61 | 0 | 69 | 75 |
| Tubulin beta-3 chain OS = *Homo sapiens* OX = 9606 GN = TUBB3 PE = 1 SV = 2 | 50 kDa | 58 | 194 | 28 | 53 |
| Endoplasmic reticulum chaperone BiP OS = *Homo sapiens* OX = 9606 GN = HSPA5 PE = 1 SV = 2 | 72 kDa | 57 | 0 | 35 | 46 |
| Myosin regulatory light chain 12A OS = *Homo sapiens* OX = 9606 GN = MYL12A PE = 1 SV = 1 | 20 kDa | 57 | 0 | 244 | 153 |
| Myosin regulatory light chain 12B OS = *Homo sapiens* OX = 9606 GN = MYL12B PE = 1 SV = 2 | 20 kDa | 57 | 0 | 240 | 149 |
| Elongation factor 2 OS = *Homo sapiens* OX = 9606 GN = EEF2 PE = 1 SV = 4 | 95 kDa | 53 | 72 | 3 | 45 |
| Filamin-C OS = *Homo sapiens* OX = 9606 GN = FLNC PE = 1 SV = 3 | 291 kDa | 53 | 62 | 3 | 63 |
| Histone H3.1 OS = *Homo sapiens* OX = 9606 GN = HIST1H3A PE = 1 SV = 2 | 15 kDa | 53 | 0 | 24 | 33 |
| 60 kDa heat shock protein, mitochondrial OS = *Homo sapiens* OX = 9606 GN = HSPD1 PE = 1 SV = 2 | 61 kDa | 52 | 58 | 14 | 58 |
| Tubulin beta-6 chain OS = *Homo sapiens* OX = 9606 GN = TUBB6 PE = 1 SV = 1 | 50 kDa | 52 | 0 | 23 | 52 |
| Isoform 4 of Collagen alpha-1(XII) chain OS = *Homo sapiens* OX = 9606 GN = COL12A1 | 325 kDa | 51 | 35 | 36 | 27 |
| Nucleophosmin OS = *Homo sapiens* OX = 9606 GN = NPM1 PE = 1 SV = 2 | 33 kDa | 48 | 103 | 15 | 43 |
| Prelamin-A/C OS = *Homo sapiens* OX = 9606 GN = LMNA PE = 1 SV = 1 | 74 kDa | 48 | 149 | 20 | 39 |
| Heat shock protein HSP 90-beta OS = *Homo sapiens* OX = 9606 GN = HSP90AB1 PE = 1 SV = 4 | 83 kDa | 47 | 0 | 3 | 31 |
| Ras GTPase-activating-like protein IQGAP1 OS = *Homo sapiens* OX = 9606 GN = IQGAP1 PE = 1 SV = 1 | 189 kDa | 47 | 0 | 11 | 36 |
| Heat shock cognate 71 kDa protein OS = *Homo sapiens* OX = 9606 GN = HSPA8 PE = 1 SV = 1 | 71 kDa | 46 | 130 | 28 | 56 |
| Annexin A2 OS = *Homo sapiens* OX = 9606 GN = ANXA2 PE = 1 SV = 2 | 39 kDa | 43 | 111 | 5 | 40 |
| Isoform 2 of Collagen alpha-1(XVIII) chain OS = *Homo sapiens* OX = 9606 GN = COL18A1 | 154 kDa | 42 | 575 | 77 | 61 |
| Myosin regulatory light polypeptide 9 OS = *Homo sapiens* OX = 9606 GN = MYL9 PE = 1 SV = 4 | 20 kDa | 42 | 380 | 131 | 81 |
| Isoform 6 of Agrin OS = *Homo sapiens* OX = 9606 GN = AGRN | 215 kDa | 41 | 168 | 42 | 70 |
| Histone H3.2 OS = *Homo sapiens* OX = 9606 GN = HIST2H3A PE = 1 SV = 3 | 15 kDa | 40 | 0 | 17 | 25 |
| Isoform 1 of Core histone macro-H2A.1 OS = *Homo sapiens* OX = 9606 GN = H2AFY | 39 kDa | 40 | 450 | 43 | 49 |
| ATP synthase subunit beta, mitochondrial OS = *Homo sapiens* OX = 9606 GN = ATP5F1B PE = 1 SV = 3 | 57 kDa | 39 | 94 | 14 | 45 |
| T-complex protein 1 subunit alpha OS = *Homo sapiens* OX = 9606 GN = TCP1 PE = 1 SV = 1 | 60 kDa | 39 | 0 | 25 | 36 |
| Isoform 2 of Heat shock protein HSP 90-alpha OS = *Homo sapiens* GN = HSP90AA1 | 98 kDa | 38 | 80 | 1 | 20 |
| Transitional endoplasmic reticulum ATPase OS = *Homo sapiens* OX = 9606 GN = VCP PE = 1 SV = 4 | 89 kDa | 38 | 86 | 1 | 37 |
| TREMBL: Q3KNV1; Q96GE1 Tax__Id = 9606 Gene__Symbol = KRT7 keratin 7 | 51 kDa | 38 | 334 | 58 | 133 |
| (Bos taurus) similar to alpha-2-macroglobulin isoform 1 | 164 kDa | 37 | 14 | 9 | 13 |
| Heterogeneous nuclear ribonucleoprotein U OS = *Homo sapiens* OX = 9606 GN = HNRNPU PE = 1 SV = 6 | 91 kDa | 35 | 64 | 12 | 29 |
| Histone H3.3 OS = *Homo sapiens* OX = 9606 GN = H3F3A PE = 1 SV = 2 | 15 kDa | 35 | 0 | 17 | 43 |
| Microtubule-associated protein 4 OS = *Homo sapiens* OX = 9606 GN = MAP4 PE = 1 SV = 3 | 121 kDa | 35 | 73 | 8 | 26 |
| Beta-actin-like protein 2 OS = *Homo sapiens* OX = 9606 GN = ACTBL2 PE = 1 SV = 2 | 42 kDa | 34 | 147 | 42 | 31 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Keratin, type I cytoskeletal 10 OS = *Homo sapiens* OX = 9606 GN = KRT10 PE = 1 SV = 6 | 59 kDa | 34 | 464 | 32 | 37 |
| Ribosome-binding protein 1 OS = *Homo sapiens* OX = 9606 GN = RRBP1 PE = 1 SV = 5 | 152 kDa | 34 | 80 | 17 | 22 |
| Cytoskeleton-associated protein 4 OS = *Homo sapiens* OX = 9606 GN = CKAP4 PE = 1 SV = 2 | 66 kDa | 33 | 139 | 30 | 35 |
| DNA-dependent protein kinase catalytic subunit OS = *Homo sapiens* OX = 9606 GN = PRKDC PE = 1 SV = 3 | 469 kDa | 33 | 10 | 0 | 5 |
| Adenylyl cyclase-associated protein 1 OS = *Homo sapiens* OX = 9606 GN = CAP1 PE = 1 SV = 5 | 52 kDa | 32 | 33 | 2 | 37 |
| Keratin, type I cytoskeletal 9 OS = *Homo sapiens* OX = 9606 GN = KRT9 PE = 1 SV = 3 | 62 kDa | 31 | 643 | 61 | 50 |
| Laminin subunit alpha-5 OS = *Homo sapiens* OX = 9606 GN = LAMA5 PE = 1 SV = 8 | 400 kDa | 31 | 50 | 7 | 13 |
| (Bos taurus) similar to fibulin-1 C isoform 1 | 77 kDa | 30 | 71 | 40 | 18 |
| 60S ribosomal protein L4 OS = *Homo sapiens* OX = 9606 GN = RPL4 PE = 1 SV = 5 | 48 kDa | 30 | 75 | 26 | 25 |
| Alpha-enolase OS = *Homo sapiens* OX = 9606 GN = ENO1 PE = 1 SV = 2 | 47 kDa | 30 | 61 | 3 | 26 |
| ATP synthase subunit alpha, mitochondrial OS = *Homo sapiens* OX = 9606 GN = ATP5F1A PE = 1 SV = 1 | 60 kDa | 30 | 52 | 12 | 34 |
| Heterogeneous nuclear ribonucleoprotein M OS = *Homo sapiens* OX = 9606 GN = HNRNPM PE = 1 SV = 3 | 78 kDa | 30 | 114 | 12 | 30 |
| Histone H2A.V OS = *Homo sapiens* OX = 9606 GN = H2AFV PE = 1 SV = 3 | 14 kDa | 30 | 131 | 23 | 34 |
| Lysyl oxidase homolog 2 OS = *Homo sapiens* OX = 9606 GN = LOXL2 PE = 1 SV = 1 | 87 kDa | 30 | 320 | 94 | 52 |
| MICOS complex subunit MIC60 OS = *Homo sapiens* OX = 9606 GN = IMMT PE = 1 SV = 1 | 84 kDa | 30 | 98 | 20 | 36 |
| SWISS-PROT: P12763 (Bos taurus) Alpha-2-HS-glycoprotein precursor | 38 kDa | 30 | 42 | 18 | 19 |
| Endoplasmin OS = *Homo sapiens* OX = 9606 GN = HSP90B1 PE = 1 SV = 1 | 92 kDa | 29 | 71 | 3 | 22 |
| TREMBL: Q0IIK2 (Bos taurus) Transferrin | 78 kDa | 29 | 15 | 2 | 16 |
| Laminin subunit beta-1 OS = *Homo sapiens* OX = 9606 GN = LAMB1 PE = 1 SV = 2 | 198 kDa | 28 | 30 | 4 | 11 |
| T-complex protein 1 subunit beta OS = *Homo sapiens* OX = 9606 GN = CCT2 PE = 1 SV = 4 | 57 kDa | 27 | 117 | 19 | 31 |
| T-complex protein 1 subunit delta OS = *Homo sapiens* OX = 9606 GN = CCT4 PE = 1 SV = 4 | 58 kDa | 27 | 73 | 19 | 26 |
| Heterogeneous nuclear ribonucleoprotein K OS = *Homo sapiens* OX = 9606 GN = HNRNPK PE = 1 SV = 1 | 51 kDa | 26 | 28 | 3 | 26 |
| Bifunctional glutamate/proline--tRNA ligase OS = *Homo sapiens* OX = 9606 GN = EPRS PE = 1 SV = 5 | 171 kDa | 25 | 20 | 0 | 1 |
| Isoform 1 of Vinculin OS = *Homo sapiens* OX = 9606 GN = VCL | 117 kDa | 25 | 25 | 1 | 26 |
| Isoform 2 of MICOS complex subunit MIC60 OS = *Homo sapiens* OX = 9606 GN = IMMT | 83 kDa | 25 | 99 | 17 | 34 |
| T-complex protein 1 subunit theta OS = *Homo sapiens* OX = 9606 GN = CCT8 PE = 1 SV = 4 | 60 kDa | 25 | 100 | 21 | 30 |
| Isoform LCRMP-4 of Dihydropyrimidinase-related protein 3 OS = *Homo sapiens* OX = 9606 GN = DPYSL3 | 74 kDa | 24 | 11 | 4 | 40 |
| Thrombospondin-1 OS = *Homo sapiens* OX = 9606 GN = THBS1 PE = 1 SV = 2 | 129 kDa | 24 | 103 | 3 | 1 |
| Isoform Short of 14-3-3 protein beta/alpha OS = *Homo sapiens* OX = 9606 GN = YWHAB | 28 kDa | 23 | 18 | 2 | 14 |
| Isoform Smooth muscle of Myosin light polypeptide 6 OS = *Homo sapiens* OX = 9606 GN = MYL6 | 17 kDa | 23 | 204 | 37 | 28 |
| Keratin, type I cytoskeletal 18 OS = *Homo sapiens* OX = 9606 GN = KRT18 PE = 1 SV = 2 | 48 kDa | 23 | 376 | 99 | 120 |
| Keratin, type II cytoskeletal 8 OS = *Homo sapiens* OX = 9606 GN = KRT8 PE = 1 SV = 7 | 54 kDa | 23 | 1404 | 107 | 155 |
| Lamin-B1 OS = *Homo sapiens* OX = 9606 GN = LMNB1 PE = 1 SV = 2 | 66 kDa | 23 | 67 | 7 | 21 |
| L-lactate dehydrogenase A chain OS = *Homo sapiens* GN = LDHA PE = 1 SV = 2 | 37 kDa | 23 | 18 | 2 | 10 |
| Profilin-1 OS = *Homo sapiens* OX = 9606 GN = PFN1PE = 1 SV = 2 | 15 kDa | 23 | 0 | 6 | 17 |
| Protein disulfide-isomerase OS = *Homo sapiens* OX = 9606 GN = P4HB PE = 1 SV = 3 | 57 kDa | 23 | 0 | 6 | 19 |
| T-complex protein 1 subunit gamma OS = *Homo sapiens* GN = CCT3 PE = 1 SV = 4 | 61 kDa | 23 | 72 | 17 | 26 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| 40S ribosomal protein S15 OS = *Homo sapiens* OX = 9606 GN = RPS15 PE = 1 SV = 2 | 17 kDa | 22 | 0 | 26 | 38 |
| ATP-citrate synthase OS = *Homo sapiens* OX = 9606 GN = ACLY PE = 1 SV = 3 | 121 kDa | 22 | 20 | 2 | 18 |
| Isoform 2 of Transgelin-2 OS = *Homo sapiens* OX = 9606 GN = TAGLN2 | 24 kDa | 22 | 47 | 1 | 20 |
| Versican core protein OS = *Homo sapiens* OX = 9606 GN = VCAN PE = 1 SV = 3 | 373 kDa | 22 | 188 | 33 | 27 |
| 60S acidic ribosomal protein P0 OS = *Homo sapiens* OX = 9606 GN = RPLP0 PE = 1 SV = 1 | 34 kDa | 21 | 56 | 14 | 19 |
| Histone H1.5 OS = *Homo sapiens* OX = 9606 GN = HIST1H1B PE = 1 SV = 3 | 23 kDa | 21 | 53 | 11 | 20 |
| Importin subunit beta-1 OS = *Homo sapiens* OX = 9606 GN = KPNB1 PE = 1 SV = 2 | 97 kDa | 21 | 19 | 1 | 6 |
| Isoform 2 of Fructose-bisphosphate aldolase A OS = *Homo sapiens* OX = 9606 GN = ALDOA | 45 kDa | 21 | 37 | 0 | 21 |
| Microtubule-associated protein 1B OS = *Homo sapiens* OX = 9606 GN = MAP1B PE = 1 SV = 2 | 271 kDa | 21 | 104 | 0 | 22 |
| TREMBL: Q3SX09 (Bos taurus) similar to HBGprotein | 22 kDa | 21 | 26 | 11 | 9 |
| 5'-nucleotidase OS = *Homo sapiens* OX = 9606 GN = NT5E PE = 1 SV = 1 | 63 kDa | 20 | 129 | 21 | 17 |
| 60S ribosomal protein L3 OS = *Homo sapiens* OX = 9606 GN = RPL3 PE = 1 SV = 2 | 46 kDa | 20 | 65 | 15 | 24 |
| 60S ribosomal protein L6 OS = *Homo sapiens* OX = 9606 GN = RPL6 PE = 1 SV = 3 | 33 kDa | 20 | 0 | 19 | 25 |
| ATP-dependent 6-phosphofructokinase, platelet type OS = *Homo sapiens* OX = 9606 GN = PFKP PE = 1 SV = 2 | 86 kDa | 20 | 9 | 0 | 18 |
| Collagen alpha-1(I) chain OS = *Homo sapiens* OX = 9606 GN = COL1A1 PE = 1 SV = 5 | 139 kDa | 20 | 41 | 43 | 27 |
| T-complex protein 1 subunit eta OS = *Homo sapiens* OX = 9606 GN = CCT7 PE = 1 SV = 2 | 59 kDa | 20 | 72 | 15 | 22 |
| Trifunctional enzyme subunit alpha, mitochondrial OS = *Homo sapiens* OX = 9606 GN = HADHA PE = 1 SV = 2 | 83 kDa | 20 | 78 | 16 | 13 |
| 40S ribosomal protein S7 OS = *Homo sapiens* OX = 9606 GN = RPS7 PE = 1 SV = 1 | 22 kDa | 19 | 104 | 25 | 28 |
| 60S ribosomal protein L9 OS = *Homo sapiens* OX = 9606 GN = RPL9 PE = 1 SV = 1 | 22 kDa | 19 | 0 | 14 | 21 |
| Actin-related protein 3 OS = *Homo sapiens* OX = 9606 GN = ACTR3 PE = 1 SV = 3 | 47 kDa | 19 | 0 | 16 | 18 |
| Annexin A5 OS = *Homo sapiens* OX = 9606 GN = ANXA5 PE = 1 SV = 2 | 36 kDa | 19 | 0 | 0 | 15 |
| Calpain-2 catalytic subunit OS = *Homo sapiens* OX = 9606 GN = CAPN2 PE = 1 SV = 6 | 80 kDa | 19 | 4 | 0 | 8 |
| Heterogeneous nuclear ribonucleoprotein Al OS = *Homo sapiens* OX = 9606 GN = HNRNPA1 PE = 1 SV = 5 | 39 kDa | 19 | 55 | 10 | 23 |
| Integrin beta-1 OS = *Homo sapiens* OX = 9606GN = ITGB1 PE = 1 SV = 2 | 88 kDa | 19 | 16 | 4 | 18 |
| Interleukin enhancer-binding factor 2 OS = *Homo sapiens* OX = 9606 GN = ILF2 PE = 1 SV = 2 | 43 kDa | 19 | 0 | 4 | 15 |
| Isoform 2 of Nidogen-2 OS = *Homo sapiens* OX = 9606 GN = NID2 | 141 kDa | 19 | 55 | 0 | 3 |
| Matrin-3 OS = *Homo sapiens* OX = 9606 GN = MATR3 PE = 1 SV = 2 | 95 kDa | 19 | 46 | 5 | 20 |
| T-complex protein 1 subunit zeta OS = *Homo sapiens* OX = 9606 GN = CCT6A PE = 1 SV = 3 | 58 kDa | 19 | 64 | 23 | 28 |
| 40S ribosomal protein S2 OS = *Homo sapiens* OX = 9606 GN = RPS2 PE = 1 SV = 2 | 31 kDa | 18 | 0 | 14 | 17 |
| 40S ribosomal protein S3 OS = *Homo sapiens* OX = 9606 GN = RPS3 PE = 1 SV = 2 | 27 kDa | 18 | 82 | 19 | 20 |
| Collagen alpha-2(IV) chain OS = *Homo sapiens* OX = 9606 GN = COL4A2 PE = 1 SV = 4 | 168 kDa | 18 | 209 | 44 | 33 |
| Epiplakin OS = *Homo sapiens* OX = 9606 GN = EPPK1 PE = 1 SV = 3 | 556 kDa | 18 | 22 | 1 | 39 |
| Heat shock 70 kDa protein 1A OS = *Homo sapiens* OX = 9606 GN = HSPA1A PE = 1 SV = 1 | 70 kDa | 18 | 31 | 0 | 23 |
| Heterogeneous nuclear ribonucleoproteins C1/C2 OS = *Homo sapiens* OX = 9606 GN = HNRNPC PE = 1 SV = 4 | 34 kDa | 18 | 52 | 6 | 22 |
| Isoform 2 of Gelsolin OS = *Homo sapiens* OX = 9606 GN = GSN | 81 kDa | 18 | 87 | 36 | 24 |
| Isoform 5 of Septin-9 OS = *Homo sapiens* OX = 9606 GN = SEPT9 | 65 kDa | 18 | 42 | 1 | 16 |
| Laminin subunit gamma-1 OS = *Homo sapiens* OX = 9606 GN = LAMC1 PE = 1 SV = 3 | 178 kDa | 18 | 48 | 0 | 6 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Nucleolin OS = *Homo sapiens* OX = 9606 GN = NCL PE = 1 SV = 3 | 77 kDa | 18 | 58 | 8 | 16 |
| Voltage-dependent anion-selective channel protein 1 OS = *Homo sapiens* OX = 9606 GN = VDAC1 PE = 1 SV = 2 | 31 kDa | 18 | 50 | 4 | 19 |
| X-ray repair cross-complementing protein 6 OS = *Homo sapiens* OX = 9606 GN = XRCC6 PE = 1 SV = 2 | 70 kDa | 18 | 33 | 2 | 14 |
| Actin-related protein 2 OS = *Homo sapiens* OX = 9606 GN = ACTR2 PE = 1 SV = 1 | 45 kDa | 17 | 43 | 17 | 28 |
| Heat shock protein beta-1 OS = *Homo sapiens* OX = 9606 GN = HSPB1 PE = 1 SV = 2 | 23 kDa | 17 | 0 | 9 | 35 |
| Histone H1.4 OS = *Homo sapiens* OX = 9606 GN = HIST1H1E PE = 1 SV = 2 | 22 kDa | 17 | 14 | 10 | 13 |
| Isoform 2 of AP-2 complex subunit beta OS = *Homo sapiens* OX = 9606 GN = AP2B1 | 106 kDa | 17 | 33 | 1 | 15 |
| Isoform 2 of Calnexin OS = *Homo sapiens* OX = 9606 GN = CANX | 72 kDa | 17 | 21 | 1 | 19 |
| Isoform 2 of Dolichyl-diphosphooligosaccharid--protein glycosyltransferase subunit 2 OS = *Homo sapiens* OX = 9606 GN = RPN2 | 68 kDa | 17 | 35 | 8 | 25 |
| Moesin OS = *Homo sapiens* OX = 9606 GN = MSN PE = 1 SV = 3 | 68 kDa | 17 | 61 | 3 | 15 |
| Protein disulfide-isomerase A3 OS = *Homo sapiens* OX = 9606 GN = PDIA3 PE = 1 SV = 4 | 57 kDa | 17 | 26 | 0 | 14 |
| Stress-70 protein, mitochondrial OS = *Homo sapiens* OX = 9606 GN = HSPA9 PE = 1 SV = 2 | 74 kDa | 17 | 33 | 0 | 10 |
| SWISS-PROT: P34955 (Bos taurus) Alpha-1-antiproteinase precursor | 46 kDa | 17 | 66 | 19 | 16 |
| T-complex protein 1 subunit epsilon OS = *Homo sapiens* OX = 9606 GN = CCT5 PE = 1 SV = 1 | 60 kDa | 17 | 110 | 18 | 22 |
| 14-3-3 protein zeta/delta OS = *Homo sapiens* OX = 9606 GN = YWHAZ PE = 1 SV = 1 | 28 kDa | 16 | 35 | 4 | 19 |
| 40S ribosomal protein S4, X isoform OS = *Homo sapiens* OX = 9606 GN = RPS4X PE = 1 SV = 2 | 30 kDa | 16 | 77 | 20 | 20 |
| 60S ribosomal protein L10 OS = *Homo sapiens* OX = 9606 GN = RPL10 PE = 1 SV = 4 | 25 kDa | 16 | 27 | 7 | 12 |
| Ezrin OS = *Homo sapiens* OX = 9606 GN = EZR PE = 1 SV = 4 | 69 kDa | 16 | 43 | 4 | 23 |
| High mobility group protein HMG-I/HMG-Y OS = *Homo sapiens* OX = 9606 GN = HMGA1 PE = 1 SV = 3 | 12 kDa | 16 | 52 | 7 | 11 |
| Hypoxia up-regulated protein 1 OS = *Homo sapiens* OX = 9606 GN = HYOU1 PE = 1 SV = 1 | 111 kDa | 16 | 37 | 0 | 18 |
| Isoform 2 of Ubiquitin-like modifier-activating enzyme 1 OS = *Homo sapiens* OX = 9606 GN = UBA1 | 114 kDa | 16 | 21 | 0 | 5 |
| Isoform 3 of Heterogeneous nuclear ribonucleoprotein Q OS = *Homo sapiens* OX = 9606 GN = SYNCRIP | 63 kDa | 16 | 37 | 5 | 20 |
| Nidogen-1 OS = *Homo sapiens* OX = 9606 GN = NID1 PE = 1 SV = 3 | 136 kDa | 16 | 56 | 1 | 7 |
| 14-3-3 protein epsilon OS = *Homo sapiens* OX = 9606 GN = YWHAE PE = 1 SV = 1 | 29 kDa | 15 | 26 | 3 | 16 |
| 40S ribosomal protein S5 OS = *Homo sapiens* OX = 9606 GN = RPS5 PE = 1 SV = 4 | 23 kDa | 15 | 0 | 10 | 12 |
| 60S ribosomal protein L5 OS = *Homo sapiens* OX = 9606 GN = RPL5 PE = 1 SV = 3 | 34 kDa | 15 | 0 | 16 | 16 |
| 60S ribosomal protein L7 OS = *Homo sapiens* OX = 9606 GN = RPL7 PE = 1 SV = 1 | 29 kDa | 15 | 61 | 14 | 14 |
| Caprin-1 OS = *Homo sapiens* OX = 9606 GN = CAPRIN1 PE = 1 SV = 2 | 78 kDa | 15 | 18 | 0 | 14 |
| Catenin alpha-1 OS = *Homo sapiens* OX = 9606 GN = CTNNA1 PE = 1 SV = 1 | 100 kDa | 15 | 13 | 0 | 12 |
| Eukaryotic initiation factor 4A-I OS = *Homo sapiens* OX = 9606 GN = EIF4A1 PE = 1 SV = 1 | 46 kDa | 15 | 28 | 2 | 8 |
| Heterogeneous nuclear ribonucleoproteins A2/B1 OS = *Homo sapiens* OX = 9606 GN = HNRNPA2B1 PE = 1 SV = 2 | 37 kDa | 15 | 58 | 6 | 20 |
| Isoform 2 of Coatomer subunit alpha OS = *Homo sapiens* OX = 9606 GN = COPA | 139 kDa | 15 | 8 | 0 | 0 |
| Isoform 2 of Protein disulfide-isomerase A6 OS = *Homo sapiens* OX = 9606 GN = PDIA6 | 54 kDa | 15 | 23 | 0 | 15 |
| Isoform 3 of Septin-2 OS = *Homo sapiens* OX = 9606 GN = SEPT2 | 43 kDa | 15 | 55 | 6 | 16 |
| Staphylococcal nuclease domain-containing protein 1 OS = *Homo sapiens* OX = 9606 GN = SND1 PE = 1 SV = 1 | 102 kDa | 15 | 33 | 0 | 6 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Triosephosphate isomerase OS = *Homo sapiens* OX = 9606 GN = TPI1 PE = 1 SV = 3 | 31 kDa | 15 | 15 | 0 | 11 |
| UDP-glucose 6-dehydrogenase OS = *Homo sapiens* OX = 9606 GN = UGDH PE = 1 SV = 1 | 55 kDa | 15 | 24 | 2 | 15 |
| ADP/ATP translocase 2 OS = *Homo sapiens* OX = 9606 GN = SLC25A5 PE = 1 SV = 7 | 33 kDa | 14 | 27 | 9 | 17 |
| ATP-dependent RNA helicase A OS = *Homo sapiens* OX = 9606 GN = DHX9 PE = 1 SV = 4 | 141 kDa | 14 | 25 | 1 | 9 |
| Cofilin-1 OS = *Homo sapiens* OX = 9606 GN = CFL1 PE = 1 SV = 3 | 19 kDa | 14 | 0 | 4 | 11 |
| eIF-2-alpha kinase activator GCN1 OS = *Homo sapiens* OX = 9606 GN = GCN1 PE = 1 SV = 6 | 293 kDa | 14 | 0 | 0 | 6 |
| Isoform 2 of Kinectin OS = *Homo sapiens* OX = 9606 GN = KTN1 | 150 kDa | 14 | 62 | 1 | 8 |
| Isoform 2 of Spliceosome RNA helicase DDX39B OS = *Homo sapiens* OX = 9606 GN = DDX39B | 51 kDa | 14 | 25 | 1 | 12 |
| Isoleucine--tRNA ligase, cytoplasmic OS = *Homo sapiens* OX = 9606 GN = IARS PE = 1 SV = 2 | 145 kDa | 14 | 0 | 0 | 0 |
| Keratin, type II cytoskeletal 2 epidermal OS = *Homo sapiens* OX = 9606 GN = KRT2 PE = 1 SV = 2 | 65 kDa | 14 | 123 | 28 | 21 |
| Ribonuclease inhibitor OS = *Homo sapiens* OX = 9606 GN = RNH1 PE = 1 SV = 2 | 50 kDa | 14 | 0 | 1 | 8 |
| SWISS-PROT: P02070 (Bos taurus) Hemoglobin subunit beta | 16 kDa | 14 | 0 | 0 | 0 |
| SWISS-PROT: Q9DCV7 Tax_Id = 10090 Gene_Symbol = Krt7 Keratin, type II cytoskeletal 7 | 51 kDa | 14 | 0 | 14 | 18 |
| Tubulointerstitial nephritis antigen-like OS = *Homo sapiens* OX = 9606 GN = TINAGL1 PE = 1 SV = 1 | 52 kDa | 14 | 173 | 78 | 38 |
| 26S proteasome non-ATPase regulatory subunit 2 OS = *Homo sapiens* OX = 9606 GN = PSMD2 PE = 1 SV = 3 | 100 kDa | 13 | 18 | 0 | 10 |
| 40S ribosomal protein S8 OS = *Homo sapiens* OX = 9606 GN = RPS8 PE = 1 SV = 2 | 24 kDa | 13 | 0 | 9 | 15 |
| 60S ribosomal protein L23 OS = *Homo sapiens* OX = 9606 GN = RPL23 PE = 1 SV = 1 | 15 kDa | 13 | 0 | 14 | 10 |
| 60S ribosomal protein L7a OS = *Homo sapiens* OX = 9606 GN = RPL7A PE = 1 SV = 2 | 30 kDa | 13 | 68 | 12 | 14 |
| ADP/ATP translocase 3 OS = *Homo sapiens* OX = 9606 GN = SLC25A6 PE = 1 SV = 4 | 33 kDa | 13 | 0 | 8 | 18 |
| Arginine--tRNA ligase, cytoplasmic OS = *Homo sapiens* OX = 9606 GN = RARS PE = 1 SV = 2 | 75 kDa | 13 | 33 | 0 | 5 |
| Calpain small subunit 1 OS = *Homo sapiens* OX = 9606 GN = CAPNS1 PE = 1 SV = 1 | 28 kDa | 13 | 0 | 0 | 22 |
| Glycine--tRNA ligase OS = *Homo sapiens* OX = 9606 GN = GARS PE = 1 SV = 3 | 83 kDa | 13 | 0 | 1 | 6 |
| Isoform 2 of Extended synaptotagmin-1 OS = *Homo sapiens* OX = 9606 GN = ESYT1 | 124 kDa | 13 | 21 | 1 | 17 |
| Isoform 2 of Nuclear mitotic apparatus protein 1 OS = *Homo sapiens* OX = 9606 GN = NUMA1 | 237 kDa | 13 | 18 | 0 | 2 |
| Isoform 2 of Tropomyosin beta chain OS = *Homo sapiens* OX = 9606 GN = TPM2 | 33 kDa | 13 | 122 | 33 | 24 |
| Isoform 7 of Interleukin enhancer-binding factor 3 OS = *Homo sapiens* GN = ILF3 | 96 kDa | 13 | 31 | 0 | 13 |
| Isoform Beta-1 of DNA topoisomerase 2-beta OS = *Homo sapiens* OX = 9606 GN = TOP2B | 183 kDa | 13 | 97 | 3 | 3 |
| Lamin-B2 OS = *Homo sapiens* OX = 9606 GN = LMNB2 PE = 1 SV = 4 | 70 kDa | 13 | 53 | 8 | 19 |
| L-lactate dehydrogenase B chain OS = *Homo sapiens* OX = 9606 GN = LDHB PE = 1 SV = 2 | 37 kDa | 13 | 0 | 0 | 6 |
| Nucleoprotein TPR OS = *Homo sapiens* OX = 9606 GN = TPR PE = 1 SV = 3 | 267 kDa | 13 | 15 | 1 | 3 |
| Receptor of activated protein C kinase 1 OS = *Homo sapiens* OX = 9606 GN = RACK1 PE = 1 SV = 3 | 35 kDa | 13 | 0 | 1 | 12 |
| Serine protease HTRA1 OS = *Homo sapiens* OX = 9606 GN = HTRA1 PE = 1 SV = 1 | 51 kDa | 13 | 0 | 15 | 1 |
| Serine/threonine-protein phosphatase 2A 65 kDa regulatory subunit A alpha isoform OS = *Homo sapiens* OX = 9606 GN = PPP2R1A PE = 1 SV = 4 | 65 kDa | 13 | 0 | 0 | 10 |
| X-ray repair cross-complementing protein 5 OS = *Homo sapiens* OX = 9606 GN = XRCC5 PE = 1 SV = 3 | 83 kDa | 13 | 0 | 2 | 15 |
| 14-3-3 protein theta OS = *Homo sapiens* OX = 9606 GN = YWHAQ PE = 1 SV = 1 | 28 kDa | 12 | 0 | 2 | 12 |
| 40S ribosomal protein S12 OS = *Homo sapiens* OX = 9606 GN = RPS12 PE = 1 SV = 3 | 15 kDa | 12 | 0 | 1 | 9 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Cytoplasmic dynein 1 light intermediate chain 2 OS = *Homo sapiens* OX = 9606 GN = DYNC1LI2 PE = 1 SV = 1 | 54 kDa | 12 | 12 | 3 | 19 |
| Glutathione S-transferase P OS = *Homo sapiens* OX = 9606 GN = GSTP1 PE = 1 SV = 2 | 23 kDa | 12 | 0 | 2 | 13 |
| Isoform 2 of Septin-7 OS = *Homo sapiens* OX = 9606 GN = SEPT7 | 51 kDa | 12 | 31 | 0 | 12 |
| Isoform 3 of Unconventional myosin-Ic OS = *Homo sapiens* OX = 9606 GN = MYO1C | 120 kDa | 12 | 64 | 9 | 8 |
| Peptidyl-prolyl cis-trans isomerase A OS = *Homo sapiens* OX = 9606 GN = PPIA PE = 1 SV = 2 | 18 kDa | 12 | 36 | 3 | 11 |
| Polyadenylate-binding protein 1 OS = *Homo sapiens* OX = 9606 GN = PABPC1 PE = 1 SV = 2 | 71 kDa | 12 | 22 | 0 | 15 |
| Rho-related GTP-binding protein RhoC OS = *Homo sapiens* OX = 9606 GN = RHOC PE = 1 SV = 1 | 22 kDa | 12 | 0 | 5 | 12 |
| Ribosomal L1 domain-containing protein 1 OS = *Homo sapiens* OX = 9606 GN = RSL1D1 PE = 1 SV = 3 | 55 kDa | 12 | 18 | 8 | 12 |
| Transgelin OS = *Homo sapiens* OX = 9606 GN = TAGLN PE = 1 SV = 4 | 23 kDa | 12 | 41 | 10 | 23 |
| 14-3-3 protein gamma OS = *Homo sapiens* OX = 9606 GN = YWHAG PE = 1 SV = 2 | 28 kDa | 11 | 0 | 1 | 14 |
| 26S proteasome regulatory subunit 6A OS = *Homo sapiens* OX = 9606 GN = PSMC3 PE = 1 SV = 1 | 47 kDa | 11 | 0 | 0 | 17 |
| 40S ribosomal protein S17 OS = *Homo sapiens* OX = 9606 GN = RPS17 PE = 1 SV = 2 | 16 kDa | 11 | 67 | 20 | 16 |
| 60S ribosomal protein L10a OS = *Homo sapiens* OX = 9606 GN = RPL10A PE = 1 SV = 2 | 25 kDa | 11 | 0 | 11 | 17 |
| 60S ribosomal protein L12 OS = *Homo sapiens* OX = 9606 GN = RPL12 PE = 1 SV = 1 | 18 kDa | 11 | 36 | 10 | 9 |
| ADP-ribosylation factor 4 OS = *Homo sapiens* OX = 9606 GN = ARF4 PE = 1 SV = 3 | 21 kDa | 11 | 0 | 8 | 14 |
| Annexin A6 OS = *Homo sapiens* OX = 9606 GN = ANXA6 PE = 1 SV = 3 | 76 kDa | 11 | 15 | 0 | 9 |
| ATP synthase subunit O, mitochondrial OS = *Homo sapiens* OX = 9606 GN = ATP5PO PE = 1 SV = 1 | 23 kDa | 11 | 0 | 5 | 10 |
| Core histone macro-H2A.2 OS = *Homo sapiens* OX = 9606 GN = H2AFY2 PE = 1 SV = 3 | 40 kDa | 11 | 226 | 28 | 21 |
| Dolichyl-diphosphooligosaccharide--protein glycosyltransferase subunit 1 OS = *Homo sapiens* OX = 9606 GN = RPN1 PE = 1 SV = 1 | 69 kDa | 11 | 43 | 7 | 18 |
| Elongation factor 1-gamma OS = *Homo sapiens* OX = 9606 GN = EEF1G PE = 1 SV = 3 | 50 kDa | 11 | 29 | 0 | 8 |
| Guanine nucleotide-binding protein G(i) subunit alpha-2 OS = *Homo sapiens* OX = 9606 GN = GNAI2 PE = 1 SV = 3 | 40 kDa | 11 | 45 | 6 | 8 |
| Heterogeneous nuclear ribonucleoprotein R OS = *Homo sapiens* OX = 9606 GN = HNRNPR PE = 1 SV = 1 | 71 kDa | 11 | 17 | 4 | 12 |
| Isoform 2 of Probable ATP-dependent RNA helicase DDX17 OS = *Homo sapiens* OX = 9606 GN = DDX17 | 72 kDa | 11 | 17 | 0 | 9 |
| Isoform 3 of Tropomyosin alpha-1 chain OS = *Homo sapiens* OX = 9606 GN = TPM1 | 33 kDa | 11 | 181 | 46 | 37 |
| Isoform 4 of Caldesmon OS = *Homo sapiens* OX = 9606 GN = CALD1 | 63 kDa | 11 | 51 | 10 | 32 |
| Leucine--tRNA ligase, cytoplasmic OS = *Homo sapiens* GN = LARS PE = 1 SV = 2 | 134 kDa | 11 | 3 | 0 | 0 |
| Phosphoglycerate kinase 1 OS = *Homo sapiens* OX = 9606 GN = PGK1 PE = 1 SV = 3 | 45 kDa | 11 | 10 | 0 | 7 |
| Polypyrimidine tract-binding protein 1 OS = *Homo sapiens* OX = 9606 GN = PTBP1 PE = 1 SV = 1 | 57 kDa | 11 | 33 | 1 | 20 |
| Rab GDP dissociation inhibitor beta OS = *Homo sapiens* OX = 9606 GN = GDI2 PE = 1 SV = 2 | 51 kDa | 11 | 17 | 0 | 10 |
| Reticulon-4 OS = *Homo sapiens* GN = RTN4 PE = 1 SV = 2 | 130 kDa | 11 | 15 | 0 | 9 |
| Serine hydroxymethyltransferase, mitochondrial OS = *Homo sapiens* GN = SHMT2 PE = 1 SV = 3 | 56 kDa | 11 | 6 | 0 | 3 |
| Serine/threonine-protein phosphatase PP1-alpha catalytic subunit OS = *Homo sapiens* OX = 9606 GN = PPP1CA PE = 1 SV = 1 | 38 kDa | 11 | 23 | 3 | 10 |
| Splicing factor, proline- and glutamine-rich OS = *Homo sapiens* OX = 9606 GN = SFPQ PE = 1 SV = 2 | 76 kDa | 11 | 43 | 5 | 18 |
| SWISS-PROT: Q3MHN5 (Bos taurus) Vitamin D-binding protein precursor | 53 kDa | 11 | 15 | 2 | 4 |
| Tenascin OS = *Homo sapiens* GN = TNC PE = 1 SV = 3 | 241 kDa | 11 | 409 | 60 | 72 |
| Threonine--tRNA ligase, cytoplasmic OS = *Homo sapiens* OX = 9606 GN = TARS PE = 1 SV = 3 | 83 kDa | 11 | 10 | 0 | 3 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Tropomyosin alpha-4 chain OS = *Homo sapiens* OX = 9606 GN = TPM4 PE = 1 SV = 3 | 29 kDa | 11 | 89 | 21 | 20 |
| 14-3-3 protein eta OS = *Homo sapiens* OX = 9606 GN = YWHAH PE = 1 SV = 4 | 28 kDa | 10 | 0 | 1 | 10 |
| 26S proteasome regulatory subunit 6B OS = *Homo sapiens* OX = 9606 GN = PSMC4 PE = 1 SV = 2 | 47 kDa | 10 | 13 | 3 | 10 |
| 60S ribosomal protein L18 OS = *Homo sapiens* GN = RPL18 PE = 1 SV = 1 | 19 kDa | 10 | 26 | 7 | 9 |
| Actin-related protein 2/3 complex subunit 2 OS = *Homo sapiens* OX = 9606 GN = ARPC2 PE = 1 SV = 1 | 34 kDa | 10 | 53 | 14 | 11 |
| A-kinase anchor protein 12 OS = *Homo sapiens* OX = 9606 GN = AKAP12 PE = 1 SV = 4 | 191 kDa | 10 | 46 | 0 | 5 |
| Asparagine--tRNA ligase, cytoplasmic OS = *Homo sapiens* OX = 9606 GN = NARS PE = 1 SV = 1 | 63 kDa | 10 | 10 | 0 | 1 |
| Aspartate--tRNA ligase, cytoplasmic OS = *Homo sapiens* OX = 9606 GN = DARS PE = 1 SV = 2 | 57 kDa | 10 | 22 | 3 | 9 |
| Dolichyl-diphosphooligosaccharide--protein glycosyltransferase 48 kDa subunit OS = *Homo sapiens* OX = 9606 GN = DDOST PE = 1 SV = 4 | 51 kDa | 10 | 13 | 6 | 17 |
| Erlin-2 OS = *Homo sapiens* OX = 9606 GN = ERLIN2 PE = 1 SV = 1 | 38 kDa | 10 | 39 | 4 | 11 |
| Fatty acid synthase OS = *Homo sapiens* OX = 9606 GN = FASN PE = 1 SV = 3 | 273 kDa | 10 | 0 | 0 | 2 |
| Heterogeneous nuclear ribonucleoprotein A3 OS = *Homo sapiens* OX = 9606 GN = HNRNPA3 PE = 1 SV = 2 | 40 kDa | 10 | 25 | 7 | 8 |
| Isoform 3 of Exportin-2 OS = *Homo sapiens* OX = 9606 GN = CSE1L | 108 kDa | 10 | 2 | 2 | 3 |
| Isoform B of AP-1 complex subunit beta-1 OS = *Homo sapiens* OX = 9606 GN = AP1B1 | 104 kDa | 10 | 0 | 0 | 11 |
| Leucine-rich PPR motif-containing protein, mitochondrial OS = *Homo sapiens* OX = 9606 GN = LRPPRC PE = 1 SV = 3 | 158 kDa | 10 | 5 | 0 | 0 |
| Non-POU domain-containing octamer-binding protein OS = *Homo sapiens* OX = 9606 GN = NONO PE = 1 SV = 4 | 54 kDa | 10 | 44 | 3 | 20 |
| Nucleolar protein 56 OS = *Homo sapiens* OX = 9606 GN = NOP56 PE = 1 SV = 4 | 66 kDa | 10 | 18 | 1 | 2 |
| Peroxidasin homolog OS = *Homo sapiens* OX = 9606 GN = PXDN PE = 1 SV = 2 | 165 kDa | 10 | 146 | 36 | 28 |
| Stomatin-like protein 2, mitochondrial OS = *Homo sapiens* OX = 9606 GN = STOML2 PE = 1 SV = 1 | 39 kDa | 10 | 18 | 3 | 10 |
| SWISS-PROT: P01966 (Bos taurus) Hemoglobin subunit alpha | 15 kDa | 10 | 34 | 12 | 10 |
| SWISS-PROT: Q3SZ57 (Bos taurus) Alpha-fetoprotein precursor | 69 kDa | 10 | 11 | 6 | 7 |
| Transforming protein RhoA OS = *Homo sapiens* OX = 9606 GN = RHOA PE = 1 SV = 1 | 22 kDa | 10 | 0 | 4 | 10 |
| 40S ribosomal protein SA OS = *Homo sapiens* OX = 9606 GN = RPSA PE = 1 SV = 1 | 33 kDa | 9 | 0 | 1 | 10 |
| 60S ribosomal protein L13 OS = *Homo sapiens* OX = 9606 GN = RPL13 PE = 1 SV = 4 | 24 kDa | 9 | 32 | 12 | 12 |
| 60S ribosomal protein L8 OS = *Homo sapiens* OX = 9606 GN = RPL8 PE = 1 SV = 2 | 28 kDa | 9 | 0 | 7 | 9 |
| Aldehyde dehydrogenase X, mitochondrial OS = *Homo sapiens* OX = 9606 GN = ALDH1B1 PE = 1 SV = 3 | 57 kDa | 9 | 14 | 4 | 11 |
| ATP-dependent RNA helicase DDX3X OS = *Homo sapiens* OX = 9606 GN = DDX3X PE = 1 SV = 3 | 73 kDa | 9 | 18 | 5 | 11 |
| Calreticulin OS = *Homo sapiens* OX = 9606 GN = CALR PE = 1 SV = 1 | 48 kDa | 9 | 44 | 4 | 11 |
| D-3-phosphoglycerate dehydrogenase OS = *Homo sapiens* OX = 9606 GN = PHGDH PE = 1 SV = 4 | 57 kDa | 9 | 0 | 0 | 2 |
| F-actin-capping protein subunit alpha-1 OS = *Homo sapiens* OX = 9606 GN = CAPZA1 PE = 1 SV = 3 | 33 kDa | 9 | 0 | 18 | 15 |
| Galectin-1 OS = *Homo sapiens* OX = 9606 GN = LGALS1 PE = 1 SV = 2 | 15 kDa | 9 | 0 | 3 | 6 |
| GTP-binding nuclear protein Ran OS = *Homo sapiens* OX = 9606 GN = RAN PE = 1 SV = 3 | 24 kDa | 9 | 0 | 6 | 11 |
| Heterochromatin protein 1-binding protein 3 OS = *Homo sapiens* OX = 9606 GN = HP1BP3 PE = 1 SV = 1 | 61 kDa | 9 | 24 | 4 | 7 |
| Isoform 1 of Voltage-dependent anion-selective channel protein 2 OS = *Homo sapiens* OX = 9606 GN = VDAC2 | 33 kDa | 9 | 19 | 1 | 5 |
| Isoform 2 of Eukaryotic translation initiation factor 3 subunit A OS = *Homo sapiens* OX = 9606 GN = EIF3A | 163 kDa | 9 | 10 | 0 | 11 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Isoform 2 of Glutamine--tRNA ligase OS = *Homo sapiens* OX = 9606 GN = QARS | 87 kDa | 9 | 16 | 0 | 4 |
| Isoform 2 of Tropomyosin alpha-3 chain OS = *Homo sapiens* OX = 9606 GN = TPM3 | 29 kDa | 9 | 99 | 16 | 17 |
| Isoform 3 of Protein AHNAK2 OS = *Homo sapiens* OX = 9606 GN = AHNAK2 | 606 kDa | 9 | 0 | 0 | 1 |
| Isoform D of Eukaryotic translation initiation factor 4 gamma 1 OS = *Homo sapiens* OX = 9606 GN = EIF4G1 | 159 kDa | 9 | 7 | 0 | 0 |
| KH domain-containing, RNA-binding, signal transduction-associated protein 1 OS = *Homo sapiens* OX = 9606 GN = KHDRBS1 PE = 1 SV = 1 | 48 kDa | 9 | 24 | 5 | 9 |
| Methionine--tRNA ligase, cytoplasmic OS = *Homo sapiens* OX = 9606 GN = MARS PE = 1 SV = 2 | 101 kDa | 9 | 1 | 0 | 0 |
| Myeloid-associated differentiation marker OS = *Homo sapiens* OX = 9606 GN = MYADM PE = 1 SV = 2 | 35 kDa | 9 | 0 | 16 | 12 |
| Neutral alpha-glucosidase AB OS = *Homo sapiens* OX = 9606 GN = GANAB PE = 1 SV = 3 | 107 kDa | 9 | 21 | 0 | 13 |
| Peroxiredoxin-5, mitochondrial OS = *Homo sapiens* OX = 9606 GN = PRDX5 PE = 1 SV = 4 | 22 kDa | 9 | 6 | 0 | 5 |
| Serine--tRNA ligase, cytoplasmic OS = *Homo sapiens* OX = 9606 GN = SARS PE = 1 SV = 3 | 59 kDa | 9 | 0 | 0 | 9 |
| Tryptophan--tRNA ligase, cytoplasmic OS = *Homo sapiens* OX = 9606 GN = WARS PE = 1 SV = 2 | 53 kDa | 9 | 6 | 1 | 7 |
| Vacuolar protein sorting-associated protein 35 OS = *Homo sapiens* OX = 9606 GN = VPS35 PE = 1 SV = 2 | 92 kDa | 9 | 5 | 0 | 4 |
| 26S proteasome non-ATPase regulatory subunit 3 OS = *Homo sapiens* OX = 9606 GN = PSMD3 PE = 1 SV = 2 | 61 kDa | 8 | 21 | 0 | 6 |
| 40S ribosomal protein S16 OS = *Homo sapiens* OX = 9606 GN = RPS16 PE = 1 SV = 2 | 16 kDa | 8 | 0 | 9 | 7 |
| 40S ribosomal protein S6 OS = *Homo sapiens* OX = 9606 GN = RPS6 PE = 1 SV = 1 | 29 kDa | 8 | 0 | 5 | 11 |
| 40S ribosomal protein S9 OS = *Homo sapiens* OX = 9606 GN = RPS9 PE = 1 SV = 3 | 23 kDa | 8 | 54 | 11 | 10 |
| ADP/ATP translocase 1 OS = *Homo sapiens* OX = 9606 GN = SLC25A4 PE = 1 SV = 4 | 33 kDa | 8 | 0 | 0 | 12 |
| Annexin A1 OS = *Homo sapiens* OX = 9606 GN = ANXA1 PE = 1 SV = 2 | 39 kDa | 8 | 0 | 0 | 8 |
| ATP-dependent RNA helicase DDX1 OS = *Homo sapiens* OX = 9606 GN = DDX1 PE = 1 SV = 2 | 82 kDa | 8 | 15 | 2 | 10 |
| Coatomer subunit gamma-1 OS = *Homo sapiens* OX = 9606 GN = COPG1 PE = 1 SV = 1 | 98 kDa | 8 | 9 | 1 | 6 |
| Elongation factor Tu, mitochondrial OS = *Homo sapiens* OX = 9606 GN = TUFM PE = 1 SV = 2 | 50 kDa | 8 | 0 | 0 | 0 |
| Erythrocyte band 7 integral membrane protein OS = *Homo sapiens* OX = 9606 GN = STOM PE = 1 SV = 3 | 32 kDa | 8 | 6 | 2 | 3 |
| Eukaryotic translation initiation factor 2 subunit 3 OS = *Homo sapiens* OX = 9606 GN = EIF2S3 PE = 1 SV = 3 | 51 kDa | 8 | 0 | 3 | 12 |
| Flotillin-1 OS = *Homo sapiens* OX = 9606 GN = FLOT1 PE = 1 SV = 3 | 47 kDa | 8 | 25 | 1 | 4 |
| Heterogeneous nuclear ribonucleoprotein L OS = *Homo sapiens* OX = 9606 GN = HNRNPL PE = 1 SV = 2 | 64 kDa | 8 | 11 | 0 | 5 |
| Isoform 2 of Ankycorbin OS = *Homo sapiens* OX = 9606 GN = RAI14 | 110 kDa | 8 | 38 | 2 | 5 |
| Isoform 2 of Bifunctional purine biosynthesis protein PURH OS = *Homo sapiens* OX = 9606 GN = ATIC | 65 kDa | 8 | 5 | 0 | 4 |
| Isoform 2 of Eukaryotic translation initiation factor 5A-1 OS = *Homo sapiens* OX = 9606 GN = EIF5A | 20 kDa | 8 | 14 | 1 | 7 |
| Isoform 2 of Golgi apparatus protein 1 OS = *Homo sapiens* OX = 9606 GN = GLG1 | 137 kDa | 8 | 4 | 9 | 1 |
| Isoform 2 of Poly(rC)-binding protein 2 OS = *Homo sapiens* OX = 9606 GN = PCBP2 | 39 kDa | 8 | 4 | 0 | 4 |
| Isoform 3 of Heterogeneous nuclear ribonucleoprotein D0 OS = *Homo sapiens* OX = 9606 GN = HNRNPD | 33 kDa | 8 | 20 | 6 | 11 |
| Isoform B of Phosphate carrier protein, mitochondrial OS = *Homo sapiens* OX = 9606 GN = SLC25A3 | 40 kDa | 8 | 7 | 5 | 8 |
| Kinesin-1 heavy chain OS = *Homo sapiens* OX = 9606 GN = KIF5B PE = 1 SV = 1 | 110 kDa | 8 | 5 | 0 | 3 |
| Malate dehydrogenase, mitochondrial OS = *Homo sapiens* OX = 9606 GN = MDH2 PE = 1 SV = 3 | 36 kDa | 8 | 17 | 0 | 13 |
| Mitochondrial carrier homolog 2 OS = *Homo sapiens* OX = 9606 GN = MTCH2 PE = 1 SV = 1 | 33 kDa | 8 | 0 | 2 | 4 |
| Pre-mRNA-processing factor 19 OS = *Homo sapiens* OX = 9606 GN = PRPF19 PE = 1 SV = 1 | 55 kDa | 8 | 0 | 0 | 14 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Prohibitin OS = *Homo sapiens* OX = 9606 GN = PHB PE = 1 SV = 1 | 30 kDa | 8 | 14 | 2 | 15 |
| Protein transport protein Sec23A OS = *Homo sapiens* OX = 9606 GN = SEC23A PE = 1 SV = 2 | 86 kDa | 8 | 9 | 1 | 10 |
| Protein transport protein Sec61 subunit alpha isoform 1 OS = *Homo sapiens* OX = 9606 GN = SEC61A1 PE = 1 SV = 2 | 52 kDa | 8 | 2 | 1 | 5 |
| Septin-11 OS = *Homo sapiens* OX = 9606 GN = SEPT11 PE = 1 SV = 3 | 49 kDa | 8 | 27 | 0 | 9 |
| Small nuclear ribonucleoprotein Sm D1 OS = *Homo sapiens* OX = 9606 GN = SNRPD1 PE = 1 SV = 1 | 13 kDa | 8 | 0 | 6 | 7 |
| SWISS-PROT: P15497 (Bos taurus) Apolipoprotein A-I precursor | 30 kDa | 8 | 21 | 6 | 4 |
| THO complex subunit 4 OS = *Homo sapiens* OX = 9606 GN = ALYREF PE = 1 SV = 3 | 27 kDa | 8 | 37 | 7 | 11 |
| TREMBL: Q3ZBS7 (Bos taurus) Vitronectin | 54 kDa | 8 | 26 | 12 | 11 |
| Ubiquitin-40S ribosomal protein S27a OS = *Homo sapiens* OX = 9606 GN = RPS27A PE = 1 SV = 2 | 18 kDa | 8 | 0 | 13 | 10 |
| 26S proteasome non-ATPase regulatory subunit 12 OS = *Homo sapiens* OX = 9606 GN = PSMD12 PE = 1 SV = 3 | 53 kDa | 7 | 6 | 0 | 2 |
| 26S proteasome regulatory subunit 8 OS = *Homo sapiens* OX = 9606 GN = PSMC5 PE = 1 SV = 1 | 46 kDa | 7 | 6 | 0 | 12 |
| 40S ribosomal protein S14 OS = *Homo sapiens* OX = 9606 GN = RPS14 PE = 1 SV = 3 | 16 kDa | 7 | 40 | 13 | 9 |
| 40S ribosomal protein S19 OS = *Homo sapiens* OX = 9606 GN = RPS19 PE = 1 SV = 2 | 16 kDa | 7 | 0 | 12 | 15 |
| 40S ribosomal protein S23 OS = *Homo sapiens* OX = 9606 GN = RPS23 PE = 1 SV = 3 | 16 kDa | 7 | 0 | 4 | 12 |
| 60S ribosomal protein L30 OS = *Homo sapiens* OX = 9606 GN = RPL30 PE = 1 SV = 2 | 13 kDa | 7 | 0 | 8 | 8 |
| ADP-ribosylation factor 3 OS = *Homo sapiens* OX = 9606 GN = ARF3 PE = 1 SV = 2 | 21 kDa | 7 | 11 | 7 | 7 |
| Aminoacyl tRNA synthase complex-interacting multifunctional protein 2 OS = *Homo sapiens* OX = 9606 GN = AIMP2 PE = 1 SV = 2 | 35 kDa | 7 | 0 | 0 | 6 |
| CAD protein OS = *Homo sapiens* OX = 9606 GN = CAD PE = 1 SV = 3 | 243 kDa | 7 | 0 | 0 | 0 |
| Catenin beta-1 OS = *Homo sapiens* OX = 9606 GN = CTNNB1 PE = 1 SV = 1 | 85 kDa | 7 | 3 | 0 | 6 |
| Cell division control protein 42 homolog OS = *Homo sapiens* OX = 9606 GN = CDC42 PE = 1 SV = 2 | 21 kDa | 7 | 0 | 2 | 11 |
| Chloride intracellular channel protein 1 OS = *Homo sapiens* OX = 9606 GN = CLIC1 PE = 1 SV = 4 | 27 kDa | 7 | 0 | 0 | 5 |
| Coatomer subunit beta OS = *Homo sapiens* OX = 9606 GN = COPB1 PE = 1 SV = 3 | 107 kDa | 7 | 5 | 0 | 1 |
| Eukaryotic initiation factor 4A-III OS = *Homo sapiens* OX = 9606 GN = EIF4A3 PE = 1 SV = 4 | 47 kDa | 7 | 20 | 4 | 8 |
| Heterogeneous nuclear ribonucleoprotein H OS = *Homo sapiens* OX = 9606 GN = HNRNPH1 PE = 1 SV = 1 | 51 kDa | 7 | 23 | 1 | 9 |
| Importin-5 OS = *Homo sapiens* OX = 9606 GN = IPO5 PE = 1 SV = 4 | 124 kDa | 7 | 5 | 0 | 3 |
| Inhibitor of nuclear factor kappa-B kinase-interacting protein OS = *Homo sapiens* OX = 9606 GN = IKBIP PE = 1 SV = 1 | 39 kDa | 7 | 7 | 6 | 7 |
| Isoform 2 of 26S proteasome non-ATPase regulatory subunit 11 OS = *Homo sapiens* OX = 9606 GN = PSMD11 | 48 kDa | 7 | 12 | 0 | 5 |
| Isoform 2 of F-actin-capping protein subunit beta OS = *Homo sapiens* OX = 9606 GN = CAPZB | 31 kDa | 7 | 46 | 10 | 5 |
| Isoform 2 of Heterogeneous nuclear ribonucleoprotein D-like OS = *Homo sapiens* OX = 9606 GN = HNRNPDL | 34 kDa | 7 | 8 | 0 | 7 |
| Isoform 2 of Integrin alpha-3 OS = *Homo sapiens* OX = 9606 GN = ITGA3 | 119 kDa | 7 | 2 | 0 | 5 |
| Isoform 2 of Nucleolar RNA helicase 2 OS = *Homo sapiens* OX = 9606 GN = DDX21 | 80 kDa | 7 | 16 | 2 | 7 |
| Isoform 2 of PDZ and LIM domain protein 7 OS = *Homo sapiens* OX = 9606 GN = PDLIM7 | 47 kDa | 7 | 13 | 0 | 5 |
| Isoform 2 of Spermine synthase OS = *Homo sapiens* OX = 9606 GN = SMS | 35 kDa | 7 | 2 | 0 | 6 |
| Isoform 2 of Transketolase OS = *Homo sapiens* OX = 9606 GN = TKT | 69 kDa | 7 | 29 | 0 | 9 |
| Isoform 3 of 116 kDa U5 small nuclear ribonucleoprotein component OS = *Homo sapiens* OX = 9606 GN = EFTUD2 | 108 kDa | 7 | 6 | 0 | 9 |
| Isoform 3 of 60S ribosomal protein L17 OS = *Homo sapiens* OX = 9606 GN = RPL17 | 26 kDa | 7 | 54 | 5 | 8 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 3 of Integrin alpha-V OS = *Homo sapiens* OX = 9606 GN = ITGAV | 111 kDa | 7 | 22 | 2 | 12 |
| Isoform SV3 of Supervillin OS = *Homo sapiens* OX = 9606 GN = SVIL | 245 kDa | 7 | 46 | 0 | 1 |
| NADH dehydrogenase [ubiquinone] 1 alpha subcomplex subunit 9, mitochondrial OS = *Homo sapiens* OX = 9606 GN = NDUFA9 PE = 1 SV = 2 | 43 kDa | 7 | 12 | 1 | 7 |
| Peroxiredoxin-1 OS = *Homo sapiens* OX = 9606 GN = PRDX1 PE = 1 SV = 1 | 22 kDa | 7 | 0 | 0 | 7 |
| Poly(rC)-binding protein 1 OS = *Homo sapiens* OX = 9606 GN = PCBP1 PE = 1 SV = 2 | 37 kDa | 7 | 0 | 0 | 2 |
| Pre-mRNA-processing-splicing factor 8 OS = *Homo sapiens* OX = 9606 GN = PRPF8 PE = 1 SV = 2 | 274 kDa | 7 | 6 | 1 | 3 |
| Probable ATP-dependent RNA helicase DDX5 OS = *Homo sapiens* OX = 9606 GN = DDX5 PE = 1 SV = 1 | 69 kDa | 7 | 25 | 7 | 19 |
| Prohibitin-2 OS = *Homo sapiens* OX = 9606 GN = PHB2 PE = 1 SV = 2 | 33 kDa | 7 | 25 | 5 | 12 |
| Protein disulfide-isomerase A4 OS = *Homo sapiens* OX = 9606 GN = PDIA4 PE = 1 SV = 2 | 73 kDa | 7 | 4 | 0 | 4 |
| Ras GTPase-activating protein-binding protein 1 OS = *Homo sapiens* OX = 9606 GN = G3BP1 PE = 1 SV = 1 | 52 kDa | 7 | 19 | 2 | 8 |
| Ras-related protein Rab-1B OS = *Homo sapiens* OX = 9606 GN = RAB1B PE = 1 SV = 1 | 22 kDa | 7 | 0 | 0 | 8 |
| RNA-binding motif protein, X chromosome OS = *Homo sapiens* OX = 9606 GN = RBMX PE = 1 SV = 3 | 42 kDa | 7 | 22 | 5 | 13 |
| Splicing factor 3B subunit 1 OS = *Homo sapiens* OX = 9606 GN = SF3B1 PE = 1 SV = 3 | 146 kDa | 7 | 16 | 1 | 3 |
| SWISS-PROT: P02535-1 Tax_Id = 10090 Gene_Symbol = Krt10 Isoform 1 of Keratin, type I cytoskeletal 10 | 58 kDa | 7 | 39 | 7 | 0 |
| SWISS-PROT: P08730-1 Tax_Id = 10090 Gene_Symbol = Krt13 Isoform 1 of Keratin, type I cytoskeletal 13 | 48 kDa | 7 | 451 | 17 | 31 |
| SWISS-PROT: Q6IFZ6 Tax_Id = 10090 Gene_Symbol = Krt77 Keratin, type II cytoskeletal 1b | 61 kDa | 7 | 32 | 10 | 5 |
| Talin-2 OS = *Homo sapiens* OX = 9606 GN = TLN2 PE = 1 SV = 4 | 272 kDa | 7 | 0 | 0 | 1 |
| Transcription intermediary factor 1-beta OS = *Homo sapiens* OX = 9606 GN = TRIM28 PE = 1 SV = 5 | 89 kDa | 7 | 5 | 0 | 0 |
| TREMBL: Q9TRI1 (Bos taurus) similar to inter-alpha-trypsin inhibitor heavy chain2 | 106 kDa | 7 | 57 | 7 | 8 |
| U5 small nuclear ribonucleoprotein 200 kDa helicase OS = *Homo sapiens* OX = 9606 GN = SNRNP200 PE = 1 SV = 2 | 245 kDa | 7 | 1 | 0 | 0 |
| Valine--tRNA ligase OS = *Homo sapiens* OX = 9606 GN = VARS PE = 1 SV = 4 | 140 kDa | 7 | 8 | 0 | 4 |
| 26S proteasome regulatory subunit 4 OS = *Homo sapiens* OX = 9606 GN = PSMC1 PE = 1 SV = 1 | 49 kDa | 6 | 25 | 1 | 6 |
| 40S ribosomal protein S26 OS = *Homo sapiens* OX = 9606 GN = RPS26 PE = 1 SV = 3 | 13 kDa | 6 | 0 | 6 | 6 |
| 60S ribosomal protein L24 OS = *Homo sapiens* OX = 9606 GN = RPL24 PE = 1 SV = 1 | 18 kDa | 6 | 0 | 5 | 6 |
| 60S ribosomal protein L27a OS = *Homo sapiens* OX = 9606 GN = RPL27A PE = 1 SV = 2 | 17 kDa | 6 | 0 | 6 | 4 |
| Alpha-centractin OS = *Homo sapiens* OX = 9606 GN = ACTR1A PE = 1 SV = 1 | 43 kDa | 6 | 26 | 3 | 11 |
| ATP-dependent RNA helicase DDX18 OS = *Homo sapiens* OX = 9606 GN = DDX18 PE = 1 SV = 2 | 75 kDa | 6 | 5 | 3 | 8 |
| Collagen alpha-1(IV) chain OS = *Homo sapiens* OX = 9606 GN = COL4A1 PE = 1 SV = 4 | 161 kDa | 6 | 69 | 21 | 7 |
| Collagen alpha-1(VIII) chain OS = *Homo sapiens* OX = 9606 GN = COL8A1 PE = 1 SV = 2 | 73 kDa | 6 | 0 | 29 | 22 |
| Cullin-associated NEDD8-dissociated protein 1 OS = *Homo sapiens* GN = CAND1 PE = 1 SV = 2 | 136 kDa | 6 | 0 | 0 | 3 |
| Dihydrolipoyllysine-residue succinyltransferase component of 2-oxoglutarate dehydrogenase complex, mitochondrial OS = *Homo sapiens* OX = 9606 GN = DLST PE = 1 SV = 4 | 49 kDa | 6 | 17 | 0 | 8 |
| Dihydropyrimidinase-related protein 2 OS = *Homo sapiens* OX = 9606 GN = DPYSL2 PE = 1 SV = 1 | 62 kDa | 6 | 3 | 0 | 5 |
| Eukaryotic translation initiation factor 3 subunit M OS = *Homo sapiens* OX = 9606 GN = EIF3M PE = 1 SV = 1 | 43 kDa | 6 | 11 | 0 | 5 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Exportin-1 OS = *Homo sapiens* OX = 9606 GN = XPO1 PE = 1 SV = 1 | 123 kDa | 6 | 0 | 0 | 0 |
| F-actin-capping protein subunit alpha-2 OS = *Homo sapiens* OX = 9606 GN = CAPZA2 PE = 1 SV = 3 | 33 kDa | 6 | 33 | 8 | 9 |
| Glycogen phosphorylase, brain form OS = *Homo sapiens* OX = 9606 GN = PYGB PE = 1 SV = 5 | 97 kDa | 6 | 0 | 0 | 1 |
| Importin-7 OS = *Homo sapiens* OX = 9606 GN = IPO7 PE = 1 SV = 1 | 120 kDa | 6 | 0 | 0 | 0 |
| Isoform 2 of 6-phosphogluconate dehydrogenase, decarboxylating OS = *Homo sapiens* OX = 9606 GN = PGD | 52 kDa | 6 | 4 | 0 | 3 |
| Isoform 2 of Coatomer subunit beta' OS = *Homo sapiens* OX = 9606 GN = COPB2 | 99 kDa | 6 | 10 | 0 | 4 |
| Isoform 2 of Coronin-1C OS = *Homo sapiens* OX = 9606 GN = CORO1C | 54 kDa | 6 | 36 | 5 | 7 |
| Isoform 2 of Elongation factor 1-delta OS = *Homo sapiens* OX = 9606 GN = EEF1D | 71 kDa | 6 | 32 | 3 | 4 |
| Isoform 2 of Inverted formin-2 OS = *Homo sapiens* OX = 9606 GN = INF2 | 135 kDa | 6 | 4 | 0 | 1 |
| Isoform 2 of Programmed cell death 6-interacting protein OS = *Homo sapiens* OX = 9606 GN = PDCD6IP | 97 kDa | 6 | 3 | 0 | 4 |
| Isoform 2 of Surfeit locus protein 4 OS = *Homo sapiens* OX = 9606 GN = SURF4 | 18 kDa | 6 | 10 | 3 | 7 |
| Isoform 3 of Plasminogen activator inhibitor 1 RNA-binding protein OS = *Homo sapiens* OX = 9606 GN = SERBP1 | 43 kDa | 6 | 11 | 6 | 7 |
| Isoform 5 of Phosphatidylinositol-binding clathrin assembly protein OS = *Homo sapiens* GN = PICALM | 70 kDa | 6 | 5 | 0 | 7 |
| Junction plakoglobin OS = *Homo sapiens* OX = 9606 GN = JUP PE = 1 SV = 3 | 82 kDa | 6 | 38 | 0 | 6 |
| Lamina-associated polypeptide 2, isoforms beta/gamma OS = *Homo sapiens* OX = 9606 GN = TMPO PE = 1 SV = 2 | 51 kDa | 6 | 26 | 7 | 7 |
| Leucine-rich repeat-containing protein 59 OS = *Homo sapiens* OX = 9606 GN = LRRC59 PE = 1 SV = 1 | 35 kDa | 6 | 0 | 7 | 10 |
| Multifunctional protein ADE2 OS = *Homo sapiens* OX = 9606 GN = PAICS PE = 1 SV = 3 | 47 kDa | 6 | 3 | 0 | 2 |
| Nicotinamide N-methyltransferase OS = *Homo sapiens* OX = 9606 GN = NNMT PE = 1 SV = 1 | 30 kDa | 6 | 0 | 0 | 1 |
| Poly [ADP-ribose] polymerase 4 OS = *Homo sapiens* OX = 9606 GN = PARP4 PE = 1 SV = 3 | 193 kDa | 6 | 19 | 0 | 5 |
| Protein S100-A6 OS = *Homo sapiens* OX = 9606 GN = S100A6 PE = 1 SV = 1 | 10 kDa | 6 | 0 | 1 | 4 |
| RuvB-like 2 OS = *Homo sapiens* OX = 9606 GN = RUVBL2 PE = 1 SV = 3 | 51 kDa | 6 | 19 | 0 | 5 |
| Sarcoplasmic/endoplasmic reticulum calcium ATPase 2 OS = *Homo sapiens* GN = ATP2A2 PE = 1 SV = 1 | 115 kDa | 6 | 6 | 0 | 0 |
| Signal transducer and activator of transcription 1-alpha/beta OS = *Homo sapiens* OX = 9606 GN = STAT1 PE = 1 SV = 2 | 87 kDa | 6 | 15 | 1 | 5 |
| Synaptic vesicle membrane protein VAT-1 homolog OS = *Homo sapiens* OX = 9606 GN = VAT1 PE = 1 SV = 2 | 42 kDa | 6 | 6 | 0 | 7 |
| Ubiquitin carboxyl-terminal hydrolase OS = *Homo sapiens* OX = 9606 GN = UCHL1 PE = 1 SV = 1 | 27 kDa | 6 | 0 | 0 | 4 |
| Very-long-chain 3-oxoacyl-CoA reductase OS = *Homo sapiens* OX = 9606 GN = HSD17B12 PE = 1 SV = 2 | 34 kDa | 6 | 0 | 2 | 6 |
| 26S proteasome non-ATPase regulatory subunit 13 OS = *Homo sapiens* OX = 9606 GN = PSMD13 PE = 1 SV = 2 | 43 kDa | 5 | 9 | 0 | 4 |
| 26S proteasome regulatory subunit 10B OS = *Homo sapiens* OX = 9606 GN = PSMC6 PE = 1 SV = 1 | 44 kDa | 5 | 0 | 0 | 5 |
| 40S ribosomal protein S10 OS = *Homo sapiens* OX = 9606 GN = RPS10 PE = 1 SV = 1 | 19 kDa | 5 | 38 | 13 | 12 |
| 40S ribosomal protein S11 OS = *Homo sapiens* OX = 9606 GN = RPS11 PE = 1 SV = 3 | 18 kDa | 5 | 26 | 3 | 7 |
| 60S ribosomal protein L21 OS = *Homo sapiens* OX = 9606 GN = RPL21 PE = 1 SV = 2 | 19 kDa | 5 | 34 | 8 | 7 |
| 60S ribosomal protein L22 OS = *Homo sapiens* OX = 9606 GN = RPL22 PE = 1 SV = 2 | 15 kDa | 5 | 0 | 6 | 8 |
| 60S ribosomal protein L23a (Fragment) OS = *Homo sapiens* OX = 9606 GN = RPL23A PE = 1 SV = 1 | 19 kDa | 5 | 0 | 9 | 9 |
| 60S ribosomal protein L27 OS = *Homo sapiens* OX = 9606 GN = RPL27 PE = 1 SV = 2 | 16 kDa | 5 | 0 | 6 | 11 |
| 60S ribosomal protein L28 OS = *Homo sapiens* OX = 9606 GN = RPL28 PE = 1 SV = 3 | 16 kDa | 5 | 13 | 4 | 4 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| 60S ribosomal protein L31 OS = *Homo sapiens* OX = 9606 GN = RPL31 PE = 1 SV = 1 | 14 kDa | 5 | 33 | 8 | 6 |
| 60S ribosomal protein L36 OS = *Homo sapiens* OX = 9606 GN = RPL36 PE = 1 SV = 3 | 12 kDa | 5 | 0 | 7 | 7 |
| Actin-related protein 2/3 complex subunit 3 OS = *Homo sapiens* OX = 9606 GN = ARPC3 PE = 1 SV = 3 | 21 kDa | 5 | 0 | 4 | 7 |
| Actin-related protein 2/3 complex subunit 4 OS = *Homo sapiens* OX = 9606 GN = ARPC4 PE = 1 SV = 3 | 20 kDa | 5 | 19 | 2 | 6 |
| Calpain-1 catalytic subunit OS = *Homo sapiens* OX = 9606 GN = CAPN1 PE = 1 SV = 1 | 82 kDa | 5 | 27 | 0 | 6 |
| Calponin-2 OS = *Homo sapiens* OX = 9606 GN = CNN2 PE = 1 SV = 4 | 34 kDa | 5 | 5 | 1 | 6 |
| Cathepsin D OS = *Homo sapiens* OX = 9606 GN = CTSD PE = 1 SV = 1 | 45 kDa | 5 | 0 | 0 | 3 |
| Cleavage and polyadenylation specificity factor subunit 5 OS = *Homo sapiens* OX = 9606 GN = NUDT21 PE = 1 SV = 1 | 26 kDa | 5 | 0 | 0 | 6 |
| Coatomer subunit epsilon OS = *Homo sapiens* GN = COPE PE = 1 SV = 3 | 34 kDa | 5 | 14 | 2 | 8 |
| Copine-3 OS = *Homo sapiens* OX = 9606 GN = CPNE3 PE = 1 SV = 1 | 60 kDa | 5 | 0 | 0 | 1 |
| Cytochrome c oxidase subunit 2 OS = *Homo sapiens* OX = 9606 GN = MT-CO2 PE = 1 SV = 1 | 26 kDa | 5 | 0 | 0 | 6 |
| DNA-(apurinic or apyrimidinic site) lyase OS = *Homo sapiens* OX = 9606 GN = APEX1 PE = 1 SV = 2 | 36 kDa | 5 | 8 | 0 | 3 |
| Erlin-1 OS = *Homo sapiens* OX = 9606 GN = ERLIN1 PE = 1 SV = 1 | 39 kDa | 5 | 0 | 0 | 4 |
| Eukaryotic translation elongation factor 1 epsilon-1 OS = *Homo sapiens* GN = EEF1E1 PE = 1 SV = 1 | 20 kDa | 5 | 7 | 2 | 7 |
| Eukaryotic translation initiation factor 2 subunit 1 OS = *Homo sapiens* OX = 9606 GN = EIF2S1 PE = 1 SV = 3 | 36 kDa | 5 | 9 | 1 | 7 |
| Eukaryotic translation initiation factor 3 subunit H OS = *Homo sapiens* OX = 9606 GN = EIF3H PE = 1 SV = 1 | 42 kDa | 5 | 0 | 0 | 3 |
| Heat shock 70 kDa protein 4 OS = *Homo sapiens* OX = 9606 GN = HSPA4 PE = 1 SV = 4 | 94 kDa | 5 | 4 | 0 | 1 |
| High mobility group protein B1 OS = *Homo sapiens* OX = 9606 GN = HMGB1 PE = 1 SV = 3 | 25 kDa | 5 | 0 | 0 | 3 |
| Importin-9 OS = *Homo sapiens* OX = 9606 GN = IPO9 PE = 1 SV = 3 | 116 kDa | 5 | 0 | 0 | 4 |
| Isoform 2 of 26S proteasome non-ATPase regulatory subunit 1 OS = *Homo sapiens* OX = 9606 GN = PSMD1 | 102 kDa | 5 | 10 | 0 | 3 |
| Isoform 2 of Calcium-binding mitochondrial carrier protein Aralar2 OS = *Homo sapiens* OX = 9606 GN = SLC25A13 | 74 kDa | 5 | 10 | 0 | 9 |
| Isoform 2 of Collagen alpha-3(VI) chain OS = *Homo sapiens* OX = 9606 GN = COL6A3 | 321 kDa | 5 | 0 | 1 | 1 |
| Isoform 2 of Eukaryotic translation initiation factor 3 subunit B OS = *Homo sapiens* OX = 9606 GN = EIF3B | 99 kDa | 5 | 5 | 0 | 6 |
| Isoform 2 of Glucose-6-phosphate isomerase OS = *Homo sapiens* OX = 9606 GN = GPI | 64 kDa | 5 | 4 | 0 | 2 |
| Isoform 2 of HLA class I histocompatibility antigen, A-11 alpha chain OS = *Homo sapiens* OX = 9606 GN = HLA-A | 41 kDa | 5 | 3 | 0 | 3 |
| Isoform 2 of Myb-binding protein 1A OS = *Homo sapiens* OX = 9606 GN = MYBBP1A | 149 kDa | 5 | 1 | 0 | 0 |
| Isoform 2 of Serine/arginine-rich splicing factor 2 OS = *Homo sapiens* OX = 9606 GN = SRSF2 | 24 kDa | 5 | 2 | 0 | 2 |
| Isoform 2 of U1 small nuclear ribonucleoprotein 70 kDa OS = *Homo sapiens* OX = 9606 GN = SNRNP70 | 51 kDa | 5 | 0 | 0 | 5 |
| Isoform 3 of Glutaminase kidney isoform, mitochondrial OS = *Homo sapiens* OX = 9606 GN = GLS | 65 kDa | 5 | 7 | 0 | 3 |
| Isoform 4 of AP-3 complex subunit delta-1 OS = *Homo sapiens* GN = AP3D1 | 115 kDa | 5 | 5 | 0 | 2 |
| Isoform 4 of Protein phosphatase 1 regulatory subunit 12A OS = *Homo sapiens* OX = 9606 GN = PPP1R12A | 109 kDa | 5 | 10 | 3 | 7 |
| Isoform Short of Eukaryotic translation initiation factor 4H OS = *Homo sapiens* OX = 9606 GN = EIF4H | 25 kDa | 5 | 5 | 1 | 4 |
| Lon protease homolog, mitochondrial OS = *Homo sapiens* GN = LONP1 PE = 1 SV = 2 | 106 kDa | 5 | 0 | 0 | 6 |
| Mannosyl-oligosaccharide glucosidase OS = *Homo sapiens* GN = MOGS PE = 1 SV = 5 | 92 kDa | 5 | 22 | 4 | 11 |
| Prolyl 3-hydroxylase 1 OS = *Homo sapiens* OX = 9606 GN = P3H1 PE = 1 SV = 2 | 83 kDa | 5 | 6 | 0 | 3 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Proteasome subunit alpha type-4 OS = *Homo sapiens* OX = 9606 GN = PSMA4 PE = 1 SV = 1 | 29 kDa | 5 | 0 | 0 | 7 |
| Protein LYRIC OS = *Homo sapiens* OX = 9606 GN = MTDH PE = 1 SV = 2 | 64 kDa | 5 | 10 | 6 | 9 |
| Protein/nucleic acid deglycase DJ-1 OS = *Homo sapiens* OX = 9606 GN = PARK7 PE = 1 SV = 2 | 20 kDa | 5 | 0 | 0 | 3 |
| Ras-related protein Rab-1A OS = *Homo sapiens* OX = 9606 GN = RAB1A PE = 1 SV = 3 | 23 kDa | 5 | 13 | 2 | 8 |
| Ras-related protein Rab-3B OS = *Homo sapiens* OX = 9606 GN = RAB3B PE = 1 SV = 2 | 25 kDa | 5 | 0 | 2 | 7 |
| Rho GDP-dissociation inhibitor 1 OS = *Homo sapiens* OX = 9606 GN = ARHGDIA PE = 1 SV = 3 | 23 kDa | 5 | 0 | 0 | 4 |
| Signal recognition particle subunit SRP72 OS = *Homo sapiens* OX = 9606 GN = SRP72 PE = 1 SV = 3 | 75 kDa | 5 | 8 | 1 | 8 |
| Small nuclear ribonucleoprotein Sm D2 OS = *Homo sapiens* OX = 9606 GN = SNRPD2 PE = 1 SV = 1 | 14 kDa | 5 | 11 | 0 | 5 |
| Sorting and assembly machinery component 50 homolog OS = *Homo sapiens* OX = 9606 GN = SAMM50 PE = 1 SV = 3 | 52 kDa | 5 | 19 | 4 | 12 |
| Src substrate cortactin OS = *Homo sapiens* OX = 9606 GN = CTTN PE = 1 SV = 2 | 62 kDa | 5 | 38 | 12 | 8 |
| SWI/SNF complex subunit SMARCC1 OS = *Homo sapiens* OX = 9606 GN = SMARCC1 PE = 1 SV = 3 | 123 kDa | 5 | 0 | 0 | 2 |
| Transcription factor BTF3 OS = *Homo sapiens* OX = 9606 GN = BTF3 PE = 1 SV = 1 | 22 kDa | 5 | 8 | 0 | 7 |
| Translocon-associated protein subunit delta OS = *Homo sapiens* OX = 9606 GN = SSR4 PE = 1 SV = 1 | 19 kDa | 5 | 0 | 2 | 4 |
| TREMBL: Q1RMK2 (Bos taurus) IGHM protein | 65 kDa | 5 | 0 | 0 | 0 |
| WD repeat-containing protein 1 OS = *Homo sapiens* OX = 9606 GN = WDR1 PE = 1 SV = 4 | 66 kDa | 5 | 11 | 0 | 5 |
| Zyxin OS = *Homo sapiens* OX = 9606 GN = ZYX PE = 1 SV = 1 | 61 kDa | 5 | 13 | 0 | 4 |
| 2-oxoglutarate dehydrogenase, mitochondrial OS = *Homo sapiens* OX = 9606 GN = OGDH PE = 1 SV = 3 | 116 kDa | 4 | 2 | 0 | 6 |
| 40S ribosomal protein S27-like OS = *Homo sapiens* OX = 9606 GN = RPS27L PE = 1 SV = 3 | 9 kDa | 4 | 0 | 1 | 1 |
| Adenosylhomocysteinase OS = *Homo sapiens* OX = 9606 GN = AHCY PE = 1 SV = 4 | 48 kDa | 4 | 4 | 0 | 2 |
| ADP-ribosylation factor 6 OS = *Homo sapiens* OX = 9606 GN = ARF6 PE = 1 SV = 2 | 20 kDa | 4 | 0 | 0 | 2 |
| Alanine--tRNA ligase, cytoplasmic OS = *Homo sapiens* OX = 9606 GN = AARS PE = 1 SV = 2 | 107 kDa | 4 | 0 | 0 | 2 |
| ATPase family AAA domain-containing protein 3A OS = *Homo sapiens* OX = 9606 GN = ATAD3A PE = 1 SV = 2 | 71 kDa | 4 | 22 | 5 | 9 |
| Coatomer subunit delta OS = *Homo sapiens* OX = 9606 GN = ARCN1 PE = 1 SV = 1 | 57 kDa | 4 | 10 | 0 | 5 |
| Cold-inducible RNA-binding protein OS = *Homo sapiens* GN = CIRBP PE = 1 SV = 1 | 19 kDa | 4 | 3 | 0 | 4 |
| Copine-1 OS = *Homo sapiens* OX = 9606 GN = CPNE1 PE = 1 SV = 1 | 59 kDa | 4 | 0 | 0 | 2 |
| Cytochrome b-c1 complex subunit 2, mitochondrial OS = *Homo sapiens* OX = 9606 GN = UQCRC2 PE = 1 SV = 3 | 48 kDa | 4 | 0 | 0 | 8 |
| DBH-like monooxygenase protein 1 OS = *Homo sapiens* OX = 9606 GN = MOXD1 PE = 1 SV = 1 | 70 kDa | 4 | 17 | 5 | 4 |
| EH domain-containing protein 1 OS = *Homo sapiens* OX = 9606 GN = EHD1 PE = 1 SV = 2 | 61 kDa | 4 | 11 | 0 | 9 |
| Eukaryotic translation initiation factor 3 subunit C OS = *Homo sapiens* OX = 9606 GN = EIF3C PE = 1 SV = 1 | 105 kDa | 4 | 4 | 0 | 5 |
| Eukaryotic translation initiation factor 4 gamma 2 OS = *Homo sapiens* GN = EIF4G2 PE = 1 SV = 1 | 102 kDa | 4 | 8 | 1 | 3 |
| Eukaryotic translation initiation factor 6 OS = *Homo sapiens* OX = 9606 GN = EIF6 PE = 1 SV = 1 | 27 kDa | 4 | 10 | 2 | 5 |
| Guanine nucleotide-binding protein G(I)/G(S)/G(T) subunit beta-1 OS = *Homo sapiens* OX = 9606 GN = GNB1 PE = 1 SV = 3 | 37 kDa | 4 | 12 | 3 | 4 |
| Isoform 10 of Calpastatin OS = *Homo sapiens* OX = 9606 GN = CAST | 82 kDa | 4 | 4 | 0 | 1 |
| Isoform 2 of 40S ribosomal protein S24 OS = *Homo sapiens* OX = 9606 GN = RPS24 | 15 kDa | 4 | 46 | 10 | 8 |
| Isoform 2 of Chromodomain-helicase-DNA-binding protein 4 OS = *Homo sapiens* GN = CHD4 | 221 kDa | 4 | 5 | 0 | 1 |
| Isoform 2 of Eukaryotic translation initiation factor 3 subunit L OS = *Homo sapiens* OX = 9606 GN = EIF3L | 61 kDa | 4 | 5 | 0 | 6 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 2 of Glucosidase 2 subunit beta OS = *Homo sapiens* OX = 9606 GN = PRKCSH | 59 kDa | 4 | 5 | 0 | 4 |
| Isoform 2 of Hexokinase-1 OS = *Homo sapiens* OX = 9606 GN = HK1 | 102 kDa | 4 | 3 | 0 | 1 |
| Isoform 2 of Isocitrate dehydrogenase [NADP], mitochondrial OS = *Homo sapiens* OX = 9606 GN = IDH2 | 45 kDa | 4 | 19 | 1 | 4 |
| Isoform 2 of Nodal modulator 2 OS = *Homo sapiens* OX = 9606 GN = NOMO2 | 134 kDa | 4 | 4 | 0 | 3 |
| Isoform 2 of Plastin-3 OS = *Homo sapiens* OX = 9606 GN = PLS3 | 69 kDa | 4 | 0 | 0 | 1 |
| Isoform 2 of Proteasome subunit alpha type-3 OS = *Homo sapiens* OX = 9606 GN = PSMA3 | 28 kDa | 4 | 6 | 0 | 4 |
| Isoform 2 of Protein SET OS = *Homo sapiens* GN = SET | 32 kDa | 4 | 7 | 0 | 4 |
| Isoform 2 of Splicing factor U2AF 65 kDa subunit OS = *Homo sapiens* OX = 9606 GN = U2AF2 | 53 kDa | 4 | 1 | 0 | 5 |
| Isoform 2 of SWI/SNF complex subunit SMARCC2 OS = *Homo sapiens* OX = 9606 GN = SMARCC2 | 125 kDa | 4 | 9 | 0 | 3 |
| Isoform 2 of Unconventional myosin-Ib OS = *Homo sapiens* OX = 9606 GN = MYO1B | 125 kDa | 4 | 16 | 0 | 0 |
| Isoform 3 of Dynactin subunit 1 OS = *Homo sapiens* OX = 9606 GN = DCTN1 | 137 kDa | 4 | 8 | 0 | 2 |
| Isoform 3 of Heterogeneous nuclear ribonucleoprotein A/B OS = *Homo sapiens* GN = HNRNPAB | 31 kDa | 4 | 10 | 2 | 6 |
| Isoform 3 of Myoferlin OS = *Homo sapiens* OX = 9606 GN = MYOF | 233 kDa | 4 | 6 | 0 | 1 |
| Isoform 3 of Nucleolar and coiled-body phosphoprotein 1 OS = *Homo sapiens* OX = 9606 GN = NOLC1 | 74 kDa | 4 | 7 | 1 | 3 |
| Isoform 4 of Inhibitor of nuclear factor kappa-B kinase-interacting protein OS = *Homo sapiens* OX = 9606 GN = IKBIP | 43 kDa | 4 | 11 | 2 | 5 |
| Isoform 6 of MMS19 nucleotide excision repair protein homolog OS = *Homo sapiens* GN = MMS19 | 108 kDa | 4 | 0 | 0 | 1 |
| Isoform Short of RNA-binding protein FUS OS = *Homo sapiens* OX = 9606 GN = FUS | 53 kDa | 4 | 9 | 0 | 4 |
| Microtubule-actin cross-linking factor 1, isoforms 1/2/3/5 OS = *Homo sapiens* OX = 9606 GN = MACF1 PE = 1 SV = 4 | 838 kDa | 4 | 2 | 0 | 0 |
| Mitochondrial carrier homolog 1 (Fragment) OS = *Homo sapiens* OX = 9606 GN = MTCH1 PE = 1 SV = 1 | 43 kDa | 4 | 0 | 0 | 5 |
| Nuclease-sensitive element-binding protein 1 OS = *Homo sapiens* OX = 9606 GN = YBX1 PE = 1 SV = 3 | 36 kDa | 4 | 0 | 7 | 9 |
| Nucleolar GTP-binding protein 1 OS = *Homo sapiens* OX = 9606 GN = GTPBP4 PE = 1 SV = 3 | 74 kDa | 4 | 5 | 0 | 1 |
| OCIA domain-containing protein 2 OS = *Homo sapiens* OX = 9606 GN = OCIAD2 PE = 1 SV = 1 | 17 kDa | 4 | 0 | 0 | 0 |
| Peroxisomal multifunctional enzyme type 2 OS = *Homo sapiens* GN = HSD17B4 PE = 1 SV = 3 | 80 kDa | 4 | 10 | 0 | 9 |
| Probable ATP-dependent RNA helicase DDX6 OS = *Homo sapiens* OX = 9606 GN = DDX6 PE = 1 SV = 2 | 54 kDa | 4 | 4 | 0 | 2 |
| Proteasome subunit alpha type-2 OS = *Homo sapiens* OX = 9606 GN = PSMA2 PE = 1 SV = 2 | 26 kDa | 4 | 0 | 0 | 8 |
| Proteasome subunit beta type-1 OS = *Homo sapiens* OX = 9606 GN = PSMB1 PE = 1 SV = 2 | 26 kDa | 4 | 0 | 0 | 6 |
| Proteasome subunit beta type-3 OS = *Homo sapiens* OX = 9606 GN = PSMB3 PE = 1 SV = 2 | 23 kDa | 4 | 0 | 0 | 6 |
| Proteasome subunit beta type-7 OS = *Homo sapiens* OX = 9606 GN = PSMB7 PE = 1 SV = 1 | 30 kDa | 4 | 0 | 0 | 6 |
| Protein arginine N-methyltransferase 1 OS = *Homo sapiens* GN = PRMT1 PE = 1 SV = 2 | 42 kDa | 4 | 3 | 0 | 1 |
| Ras GTPase-activating protein-binding protein 2 OS = *Homo sapiens* OX = 9606 GN = G3BP2 PE = 1 SV = 2 | 54 kDa | 4 | 14 | 2 | 5 |
| Ras suppressor protein 1 OS = *Homo sapiens* OX = 9606 GN = RSU1 PE = 1 SV = 3 | 32 kDa | 4 | 16 | 1 | 8 |
| RNA-binding protein Raly OS = *Homo sapiens* OX = 9606 GN = RALY PE = 1 SV = 1 | 32 kDa | 4 | 14 | 2 | 7 |
| Sideroflexin-1 OS = *Homo sapiens* OX = 9606GN = SFXN1 PE = 1 SV = 4 | 36 kDa | 4 | 3 | 1 | 4 |
| Sideroflexin-3 OS = *Homo sapiens* OX = 9606GN = SFXN3 PE = 1 SV = 3 | 36 kDa | 4 | 0 | 0 | 4 |
| Signal recognition particle 9 kDa protein OS = *Homo sapiens* OX = 9606 GN = SRP9 PE = 1 SV = 2 | 10 kDa | 4 | 7 | 1 | 3 |
| Splicing factor 3A subunit 1 OS = *Homo sapiens* OX = 9606 GN = SF3A1 PE = 1 SV = 1 | 89 kDa | 4 | 6 | 0 | 5 |

TABLE 2-continued

| Amniotic Fluid Cell-Derived ECM Components | | | | | | |
|---|---|---|---|---|---|---|
| | | Total Spectra Count | | | |
| Protein | MW | Matrix A | Matrix B | Matrix C | Matrix D |
| SWISS-PROT: Q9TTE1 (Bos taurus) Endopin-1 precursor | 46 kDa | 4 | 4 | 2 | 1 |
| Thy-l membrane glycoprotein OS = *Homo sapiens* OX = 9606 GN = THY1 PE = 1 SV = 2 | 18 kDa | 4 | 0 | 6 | 3 |
| Transmembrane protein 43 OS = *Homo sapiens* OX = 9606 GN = TMEM43 PE = 1 SV = 1 | 45 kDa | 4 | 0 | 5 | 6 |
| TREMBL: Q1A7A4 (Bos taurus) similar to complement component C5 | 189 kDa | 4 | 0 | 0 | 0 |
| Tricarboxylate transport protein, mitochondrial OS = *Homo sapiens* OX = 9606 GN = SLC25A1 PE = 1 SV = 2 | 34 kDa | 4 | 2 | 0 | 3 |
| U2 small nuclear ribonucleoprotein A' OS = *Homo sapiens* OX = 9606 GN = SNRPA1 PE = 1 SV = 2 | 28 kDa | 4 | 0 | 0 | 4 |
| Vasodilator-stimulated phosphoprotein OS = *Homo sapiens* OX = 9606 GN = VASP PE = 1 SV = 3 | 40 kDa | 4 | 10 | 0 | 10 |
| (Bos taurus) 47 kDa protein | 47 kDa | 3 | 0 | 0 | 0 |
| (Bos taurus) similar to Complement C4-A precursor | 193 kDa | 3 | 7 | 4 | 4 |
| 26S proteasome non-ATPase regulatory subunit 5 OS = *Homo sapiens* OX = 9606 GN = PSMD5 PE = 1 SV = 3 | 56 kDa | 3 | 4 | 0 | 1 |
| 26S proteasome non-ATPase regulatory subunit 7 OS = *Homo sapiens* OX = 9606 GN = PSMD7 PE = 1 SV = 2 | 37 kDa | 3 | 10 | 0 | 6 |
| 26S proteasome regulatory subunit 7 OS = *Homo sapiens* OX = 9606 GN = PSMC2 PE = 1 SV = 3 | 49 kDa | 3 | 4 | 0 | 4 |
| 39S ribosomal protein L28, mitochondrial OS = *Homo sapiens* OX = 9606 GN = MRPL28 PE = 1 SV = 4 | 30 kDa | 3 | 0 | 0 | 1 |
| 40S ribosomal protein S15a OS = *Homo sapiens* OX = 9606 GN = RPS15A PE = 1 SV = 2 | 15 kDa | 3 | 0 | 2 | 3 |
| 60S ribosomal protein L15 OS = *Homo sapiens* OX = 9606 GN = RPL15 PE = 1 SV = 2 | 24 kDa | 3 | 27 | 3 | 11 |
| Acetyl-CoA acetyltransferase, mitochondrial OS = *Homo sapiens* OX = 9606 GN = ACAT1 PE = 1 SV = 1 | 45 kDa | 3 | 11 | 0 | 5 |
| ATP synthase F(0) complex subunit B1, mitochondrial OS = *Homo sapiens* OX = 9606 GN = ATP5PB PE = 1 SV = 2 | 29 kDa | 3 | 0 | 0 | 2 |
| ATP-binding cassette sub-family D member 3 OS = *Homo sapiens* OX = 9606 GN = ABCD3 PE = 1 SV = 1 | 75 kDa | 3 | 8 | 2 | 2 |
| Calponin-3 OS = *Homo sapiens* OX = 9606 GN = CNN3 PE = 1 SV = 1 | 36 kDa | 3 | 4 | 1 | 6 |
| Cell surface glycoprotein MUC18 OS = *Homo sapiens* OX = 9606 GN = MCAM PE = 1 SV = 2 | 72 kDa | 3 | 3 | 0 | 6 |
| CTP synthase 1 OS = *Homo sapiens* OX = 9606 GN = CTPS1 PE = 1 SV = 2 | 67 kDa | 3 | 0 | 0 | 0 |
| Cytoplasmic dynein 1 light intermediate chain 1 OS = *Homo sapiens* OX = 9606 GN = DYNC1LI1 PE = 1 SV = 3 | 57 kDa | 3 | 11 | 0 | 4 |
| Cytoplasmic FMR1-interacting protein 1 OS = *Homo sapiens* OX = 9606 GN = CYFIP1 PE = 1 SV = 1 | 145 kDa | 3 | 2 | 0 | 0 |
| Desmoglein-2 OS = *Homo sapiens* OX = 9606 GN = DSG2 PE = 1 SV = 2 | 122 kDa | 3 | 17 | 5 | 7 |
| Desmoplakin OS = *Homo sapiens* OX = 9606 GN = DSP PE = 1 SV = 3 | 332 kDa | 3 | 35 | 0 | 0 |
| Dihydrolipoyllysine-residue acetyltransferase component of pyruvate dehydrogenase complex, mitochondrial OS = *Homo sapiens* OX = 9606 GN = DLAT PE = 1 SV = 3 | 69 kDa | 3 | 0 | 2 | 10 |
| DnaJ homolog subfamily A member 2 OS = *Homo sapiens* OX = 9606 GN = DNAJA2 PE = 1 SV = 1 | 46 kDa | 3 | 0 | 1 | 6 |
| Dynein light chain Tctex-type 1 OS = *Homo sapiens* OX = 9606 GN = DYNLT1 PE = 1 SV = 1 | 12 kDa | 3 | 13 | 3 | 5 |
| E3 ubiquitin/ISG15 ligase TRIM25 OS = *Homo sapiens* OX = 9606 GN = TRIM25 PE = 1 SV = 2 | 71 kDa | 3 | 0 | 0 | 1 |
| EGF-like repeat and discoidin I-like domain-containing protein 3 OS = *Homo sapiens* OX = 9606 GN = EDIL3 PE = 1 SV = 1 | 54 kDa | 3 | 26 | 1 | 7 |
| Enoyl-CoA hydratase, mitochondrial OS = *Homo sapiens* OX = 9606 GN = ECHS1 PE = 1 SV = 4 | 31 kDa | 3 | 0 | 0 | 2 |
| Epidermal growth factor receptor kinase substrate 8-like protein 2 OS = *Homo sapiens* OX = 9606 GN = EPS8L2 PE = 1 SV = 2 | 81 kDa | 3 | 4 | 0 | 5 |
| ER lumen protein-retaining receptor 1 OS = *Homo sapiens* OX = 9606 GN = KDELR1 PE = 1 SV = 1 | 25 kDa | 3 | 0 | 2 | 1 |
| Eukaryotic translation initiation factor 2 subunit 2 OS = *Homo sapiens* OX = 9606 GN = EIF2S2 PE = 1 SV = 2 | 38 kDa | 3 | 0 | 7 | 10 |
| General transcription factor II-I OS = *Homo sapiens* OX = 9606 GN = GTF2I PE = 1 SV = 2 | 112 kDa | 3 | 27 | 3 | 3 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| High mobility group protein HMGI-C OS = *Homo sapiens* GN = HMGA2 PE = 1 SV = 1 | 12 kDa | 3 | 48 | 3 | 0 |
| Inosine-5'-monophosphate dehydrogenase 2 OS = *Homo sapiens* OX = 9606 GN = IMPDH2 PE = 1 SV = 2 | 56 kDa | 3 | 0 | 0 | 2 |
| Isoform 1 of Apoptosis inhibitor 5 OS = *Homo sapiens* OX = 9606 GN = API5 | 49 kDa | 3 | 5 | 0 | 3 |
| Isoform 12 of Titin OS = *Homo sapiens* OX = 9606 GN = TTN | 3994 kDa | 3 | 1 | 3 | 3 |
| Isoform 2 of 3-hydroxyacyl-CoA dehydrogenase type-2 OS = *Homo sapiens* OX = 9606 GN = HSD17B10 | 26 kDa | 3 | 2 | 0 | 1 |
| Isoform 2 of ATP-dependent RNA helicase DDX54 OS = *Homo sapiens* OX = 9606 GN = DDX54 | 99 kDa | 3 | 1 | 0 | 3 |
| Isoform 2 of B-cell receptor-associated protein 31 OS = *Homo sapiens* OX = 9606 GN = BCAP31 | 35 kDa | 3 | 1 | 4 | 7 |
| Isoform 2 of Calcium-binding mitochondrial carrier protein SCaMC-1 OS = *Homo sapiens* OX = 9606 GN = SLC25A24 | 51 kDa | 3 | 1 | 0 | 5 |
| Isoform 2 of Collagen alpha-1(V) chain OS = *Homo sapiens* OX = 9606 GN = COL5A1 | 184 kDa | 3 | 0 | 13 | 6 |
| Isoform 2 of E3 ubiquitin-protein ligase UBR4 OS = *Homo sapiens* OX = 9606 GN = UBR4 | 576 kDa | 3 | 0 | 0 | 1 |
| Isoform 2 of Importin-4 OS = *Homo sapiens* GN = IPO4 | 119 kDa | 3 | 0 | 0 | 0 |
| Isoform 2 of Insulin-like growth factor 2 mRNA-binding protein 2 OS = *Homo sapiens* GN = IGF2BP2 | 62 kDa | 3 | 19 | 2 | 5 |
| Isoform 2 of NADH dehydrogenase [ubiquinone] 1 alpha subcomplex subunit 10, mitochondrial OS = *Homo sapiens* OX = 9606 GN = NDUFA10 | 49 kDa | 3 | 0 | 0 | 2 |
| Isoform 2 of NADH-cytochrome b5 reductase 3 OS = *Homo sapiens* OX = 9606 GN = CYB5R3 | 32 kDa | 3 | 6 | 0 | 3 |
| Isoform 2 of Nuclear pore complex protein Nup107 OS = *Homo sapiens* OX = 9606 GN = NUP107 | 103 kDa | 3 | 1 | 0 | 0 |
| Isoform 2 of Protein Dok-7 OS = *Homo sapiens* OX = 9606 GN = DOK7 | 37 kDa | 3 | 0 | 2 | 5 |
| Isoform 2 of Protein FAM98B OS = *Homo sapiens* OX = 9606 GN = FAM98B | 46 kDa | 3 | 9 | 0 | 4 |
| Isoform 2 of Sacsin OS = *Homo sapiens* OX = 9606 GN = SACS | 437 kDa | 3 | 0 | 0 | 0 |
| Isoform 2 of Serine/arginine-rich splicing factor 3 OS = *Homo sapiens* OX = 9606 GN = SRSF3 | 14 kDa | 3 | 8 | 0 | 4 |
| Isoform 2 of Small nuclear ribonucleoprotein Sm D3 OS = *Homo sapiens* OX = 9606 GN = SNRPD3 | 13 kDa | 3 | 10 | 2 | 3 |
| Isoform 2 of Stathmin OS = *Homo sapiens* OX = 9606 GN = STMN1 | 20 kDa | 3 | 0 | 0 | 3 |
| Isoform 2 of TP53-binding protein 1 OS = *Homo sapiens* OX = 9606 GN = TP53BP1 | 214 kDa | 3 | 4 | 0 | 0 |
| Isoform 2 of Very long-chain specific acyl-CoA dehydrogenase, mitochondrial OS = *Homo sapiens* OX = 9606 GN = ACADVL | 68 kDa | 3 | 10 | 0 | 5 |
| Isoform 2 of Voltage-dependent anion-selective channel protein 3 OS = *Homo sapiens* OX = 9606 GN = VDAC3 | 31 kDa | 3 | 15 | 0 | 5 |
| Isoform 2 of V-type proton ATPase catalytic subunit A OS = *Homo sapiens* OX = 9606 GN = ATP6V1A | 65 kDa | 3 | 15 | 1 | 2 |
| Isoform 3 of 4F2 cell-surface antigen heavy chain OS = *Homo sapiens* GN = SLC3A2 | 62 kDa | 3 | 1 | 1 | 1 |
| Isoform 3 of Aldehyde dehydrogenase family 16 member A1 OS = *Homo sapiens* OX = 9606 GN = ALDH16A1 | 80 kDa | 3 | 0 | 0 | 1 |
| Isoform 3 of Drebrin OS = *Homo sapiens* GN = DBN1 | 76 kDa | 3 | 31 | 4 | 3 |
| Isoform 3 of Erbin OS = *Homo sapiens* OX = 9606 GN = ERBIN | 153 kDa | 3 | 0 | 0 | 0 |
| Isoform 3 of Nucleoside diphosphate kinase B OS = *Homo sapiens* GN = NME2 | 30 kDa | 3 | 12 | 0 | 7 |
| Isoform 3 of Perilipin-3 OS = *Homo sapiens* OX = 9606 GN = PLIN3 | 47 kDa | 3 | 1 | 0 | 3 |
| Isoform 3 of SUN domain-containing protein 2 OS = *Homo sapiens* OX = 9606 GN = SUN2 | 80 kDa | 3 | 15 | 4 | 12 |
| Isoform 3 of Transportin-3 OS = *Homo sapiens* OX = 9606 GN = TNPO3 | 103 kDa | 3 | 0 | 0 | 0 |
| Isoform 4 of 26S proteasome non-ATPase regulatory subunit 6 OS = *Homo sapiens* OX = 9606 GN = PSMD6 | 52 kDa | 3 | 17 | 0 | 2 |
| Isoform 9 of Protein transport protein Sec31A OS = *Homo sapiens* GN = SEC31A | 131 kDa | 3 | 3 | 0 | 1 |
| Isoform K of Kinesin light chain 1 OS = *Homo sapiens* OX = 9606 GN = KLC1 | 70 kDa | 3 | 2 | 0 | 2 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| MICOS complex subunit MIC19 OS = *Homo sapiens* OX = 9606 GN = CHCHD3 PE = 1 SV = 1 | 26 kDa | 3 | 0 | 3 | 6 |
| Nuclear pore complex protein Nup205 OS = *Homo sapiens* OX = 9606 GN = NUP205 PE = 1 SV = 3 | 228 kDa | 3 | 0 | 0 | 0 |
| Nuclear pore complex protein Nup93 OS = *Homo sapiens* OX = 9606 GN = NUP93 PE = 1 SV = 2 | 93 kDa | 3 | 6 | 0 | 3 |
| PC4 and SFRS1 -interacting protein OS = *Homo sapiens* OX = 9606 GN = PSIP1 PE = 1 SV = 1 | 60 kDa | 3 | 16 | 1 | 5 |
| Peroxiredoxin-6 OS = *Homo sapiens* OX = 9606 GN = PRDX6 PE = 1 SV = 3 | 25 kDa | 3 | 0 | 0 | 0 |
| PRA1 family protein 3 OS = *Homo sapiens* OX = 9606 GN = ARL6IP5 PE = 1 SV = 1 | 22 kDa | 3 | 7 | 1 | 4 |
| Proliferating cell nuclear antigen OS = *Homo sapiens* OX = 9606 GN = PCNA PE = 1 SV = 1 | 29 kDa | 3 | 0 | 0 | 0 |
| Proliferation-associated protein 2G4 OS = *Homo sapiens* OX = 9606 GN = PA2G4 PE = 1 SV = 3 | 44 kDa | 3 | 16 | 0 | 6 |
| Proteasome adapter and scaffold protein ECM29 OS = *Homo sapiens* OX = 9606 GN = ECPAS PE = 1 SV = 2 | 204 kDa | 3 | 0 | 0 | 2 |
| Proteasome subunit beta type-4 OS = *Homo sapiens* OX = 9606 GN = PSMB4 PE = 1 SV = 4 | 29 kDa | 3 | 0 | 0 | 4 |
| Proteasome subunit beta type-6 OS = *Homo sapiens* OX = 9606 GN = PSMB6 PE = 1 SV = 4 | 25 kDa | 3 | 0 | 0 | 3 |
| Protein DEK OS = *Homo sapiens* OX = 9606 GN = DEK PE = 1 SV = 1 | 43 kDa | 3 | 2 | 0 | 2 |
| Protein S 100-A11 OS = *Homo sapiens* OX = 9606 GN = S100A11 PE = 1 SV = 2 | 12 kDa | 3 | 0 | 0 | 2 |
| Protein transport protein Sec61 subunit beta OS = *Homo sapiens* OX = 9606 GN = SEC61B PE = 1 SV = 2 | 10 kDa | 3 | 1 | 2 | 2 |
| Puromycin-sensitive aminopeptidase OS = *Homo sapiens* GN = NPEPPS PE = 1 SV = 2 | 103 kDa | 3 | 0 | 0 | 2 |
| Ras-related protein Rab-11B OS = *Homo sapiens* OX = 9606 GN = RAB11B PE = 1 SV = 4 | 24 kDa | 3 | 9 | 1 | 6 |
| Ras-related protein Rab-14 OS = *Homo sapiens* OX = 9606 GN = RAB14 PE = 1 SV = 4 | 24 kDa | 3 | 0 | 0 | 6 |
| Ras-related protein Rap-1b OS = *Homo sapiens* OX = 9606 GN = RAP1B PE = 1 SV = 1 | 21 kDa | 3 | 7 | 2 | 3 |
| Ras-related protein R-Ras OS = *Homo sapiens* OX = 9606 GN = RRAS PE = 1 SV = 1 | 23 kDa | 3 | 0 | 0 | 2 |
| RNA transcription, translation and transport factor protein OS = *Homo sapiens* OX = 9606 GN = RTRAF PE = 1 SV = 1 | 28 kDa | 3 | 0 | 4 | 6 |
| SAP domain-containing ribonucleoprotein OS = *Homo sapiens* OX = 9606 GN = SARNP PE = 1 SV = 3 | 24 kDa | 3 | 0 | 0 | 2 |
| SWISS-PROT: P06868 (Bos taurus) Plasminogen precursor | 91 kDa | 3 | 1 | 5 | 0 |
| SWISS-PROT: P41361 (Bos taurus) Antithrombin-III precursor | 52 kDa | 3 | 3 | 0 | 0 |
| TAR DNA-binding protein 43 OS = *Homo sapiens* OX = 9606 GN = TARDBP PE = 1 SV = 1 | 45 kDa | 3 | 2 | 0 | 3 |
| Thioredoxin reductase 1, cytoplasmic OS = *Homo sapiens* GN = TXNRD1 PE = 1 SV = 3 | 71 kDa | 3 | 0 | 0 | 1 |
| Thrombospondin type-1 domain-containing protein 4 OS = *Homo sapiens* OX = 9606 GN = THSD4 PE = 2 SV = 2 | 112 kDa | 3 | 22 | 10 | 1 |
| TREMBL: Q2KJF1 (Bos taurus) Alpha-1-Bglycoprotein | 54 kDa | 3 | 11 | 1 | 3 |
| tRNA-splicing ligase RtcB homolog OS = *Homo sapiens* OX = 9606 GN = RTCB PE = 1 SV = 1 | 55 kDa | 3 | 19 | 3 | 9 |
| Tyrosine--tRNA ligase, cytoplasmic OS = *Homo sapiens* OX = 9606 GN = YARS PE = 1 SV = 4 | 59 kDa | 3 | 0 | 0 | 2 |
| Ubiquitin thioesterase OTUB1 OS = *Homo sapiens* OX = 9606 GN = OTUB1 PE = 1 SV = 2 | 31 kDa | 3 | 0 | 0 | 1 |
| Vigilin OS = *Homo sapiens* OX = 9606 GN = HDLBP PE = 1 SV = 2 | 141 kDa | 3 | 9 | 0 | 2 |
| V-type proton ATPase 116 kDa subunit a isoform 3 OS = *Homo sapiens* OX = 9606 GN = TCIRG1 PE = 1 SV = 3 | 93 kDa | 3 | 16 | 1 | 2 |
| WD repeat-containing protein 61 OS = *Homo sapiens* OX = 9606 GN = WDR61 PE = 1 SV = 1 | 34 kDa | 3 | 0 | 1 | 4 |
| 39S ribosomal protein L41, mitochondrial OS = *Homo sapiens* OX = 9606 GN = MRPL41 PE = 1 SV = 1 | 15 kDa | 2 | 0 | 0 | 5 |
| 40S ribosomal protein S25 OS = *Homo sapiens* OX = 9606 GN = RPS25 PE = 1 SV = 1 | 14 kDa | 2 | 0 | 8 | 7 |
| 60S acidic ribosomal protein P1 OS = *Homo sapiens* OX = 9606 GN = RPLP1 PE = 1 SV = 1 | 12 kDa | 2 | 13 | 3 | 5 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Actin-like protein 6A OS = *Homo sapiens* OX = 9606 GN = ACTL6A PE = 1 SV = 1 | 47 kDa | 2 | 12 | 0 | 2 |
| Actin-related protein 2/3 complex subunit 5 OS = *Homo sapiens* OX = 9606 GN = ARPC5 PE = 1 SV = 3 | 16 kDa | 2 | 15 | 5 | 7 |
| Actin-related protein 2/3 complex subunit 5-like protein OS = *Homo sapiens* OX = 9606 GN = ARPC5L PE = 1 SV = 1 | 17 kDa | 2 | 0 | 6 | 5 |
| Activated RNA polymerase II transcriptional coactivator p15 OS = *Homo sapiens* OX = 9606 GN = SUB1 PE = 1 SV = 3 | 14 kDa | 2 | 1 | 0 | 2 |
| Alcohol dehydrogenase [NADP(+)] OS = *Homo sapiens* OX = 9606 GN = AKR1A1 PE = 1 SV = 3 | 37 kDa | 2 | 0 | 0 | 1 |
| Aspartyl/asparaginyl beta-hydroxylase OS = *Homo sapiens* OX = 9606 GN = ASPH PE = 1 SV = 3 | 86 kDa | 2 | 4 | 1 | 3 |
| ATP synthase subunit f, mitochondrial OS = *Homo sapiens* OX = 9606 GN = ATP5MF PE = 1 SV = 1 | 11 kDa | 2 | 0 | 2 | 2 |
| ATP-binding cassette sub-family B member 6, mitochondrial (Fragment) OS = *Homo sapiens* OX = 9606 GN = ABCB6 PE = 1 SV = 1 | 78 kDa | 2 | 0 | 0 | 0 |
| Catenin delta-1 OS = *Homo sapiens* OX = 9606 GN = CTNND1 PE = 1 SV = 1 | 108 kDa | 2 | 13 | 0 | 1 |
| Cathepsin B OS = *Homo sapiens* OX = 9606 GN = CTSB PE = 1 SV = 3 | 38 kDa | 2 | 0 | 0 | 0 |
| Caveolin-1 OS = *Homo sapiens* OX = 9606 GN = CAV1 PE = 1 SV = 4 | 20 kDa | 2 | 11 | 2 | 4 |
| Cell cycle and apoptosis regulator protein 2 OS = *Homo sapiens* GN = CCAR2 PE = 1 SV = 2 | 103 kDa | 2 | 1 | 0 | 4 |
| Centromere protein V OS = *Homo sapiens* OX = 9606 GN = CENPV PE = 1 SV = 1 | 30 kDa | 2 | 3 | 0 | 1 |
| Citrate synthase OS = *Homo sapiens* OX = 9606 GN = CS PE = 1 SV = 1 | 50 kDa | 2 | 0 | 0 | 3 |
| Cytochrome b-c1 complex subunit 1, mitochondrial OS = *Homo sapiens* OX = 9606 GN = UQCRC1 PE = 1 SV = 3 | 53 kDa | 2 | 0 | 0 | 1 |
| Cytochrome c oxidase subunit 7A2, mitochondrial OS = *Homo sapiens* OX = 9606 GN = COX7A2 PE = 1 SV = 1 | 9 kDa | 2 | 0 | 0 | 1 |
| Dystonin OS = *Homo sapiens* OX = 9606 GN = DST PE = 1 SV = 4 | 861 kDa | 2 | 0 | 0 | 0 |
| EH domain-containing protein 2 OS = *Homo sapiens* OX = 9606 GN = EHD2 PE = 1 SV = 2 | 61 kDa | 2 | 2 | 0 | 3 |
| Enhancer of mRNA-decapping protein 4 OS = *Homo sapiens* GN = EDC4 PE = 1 SV = 1 | 152 kDa | 2 | 0 | 0 | 0 |
| Eukaryotic translation initiation factor 5B OS = *Homo sapiens* OX = 9606 GN = EIF5B PE = 1 SV = 4 | 139 kDa | 2 | 0 | 0 | 2 |
| Exosome RNA helicase MTR4 OS = *Homo sapiens* OX = 9606 GN = MTREX PE = 1 SV = 3 | 118 kDa | 2 | 0 | 0 | 1 |
| Far upstream element-binding protein 2 OS = *Homo sapiens* OX = 9606 GN = KHSRP PE = 1 SV = 4 | 73 kDa | 2 | 0 | 0 | 0 |
| Ferritin heavy chain OS = *Homo sapiens* OX = 9606 GN = FTH1 PE = 1 SV = 2 | 21 kDa | 2 | 0 | 0 | 1 |
| FH2 domain-containing protein 1 OS = *Homo sapiens* OX = 9606 GN = FHDC1 PE = 1 SV = 2 | 125 kDa | 2 | 0 | 0 | 0 |
| Glutaredoxin-3 OS = *Homo sapiens* OX = 9606 GN = GLRX3 PE = 1 SV = 2 | 37 kDa | 2 | 0 | 0 | 0 |
| GTP-binding protein SAR1a OS = *Homo sapiens* OX = 9606 GN = SAR1A PE = 1 SV = 1 | 22 kDa | 2 | 0 | 0 | 3 |
| Guanine nucleotide-binding protein G(I)/G(S)/G(T) subunit beta-2 OS = *Homo sapiens* OX = 9606 GN = GNB2 PE = 1 SV = 3 | 37 kDa | 2 | 14 | 0 | 0 |
| Heterogeneous nuclear ribonucleoprotein U-like protein 2 OS = *Homo sapiens* OX = 9606 GN = HNRNPUL2 PE = 1 SV = 1 | 85 kDa | 2 | 8 | 0 | 2 |
| High mobility group protein B3 OS = *Homo sapiens* OX = 9606 GN = HMGB3 PE = 1 SV = 4 | 23 kDa | 2 | 0 | 0 | 3 |
| Inversin OS = *Homo sapiens* OX = 9606 GN = INVS PE = 1 SV = 2 | 118 kDa | 2 | 0 | 0 | 0 |
| Isoform 10 of CD44 antigen OS = *Homo sapiens* OX = 9606 GN = CD44 | 53 kDa | 2 | 27 | 5 | 2 |
| Isoform 2 of 40S ribosomal protein S20 OS = *Homo sapiens* OX = 9606 GN = RPS20 | 16 kDa | 2 | 7 | 1 | 3 |
| Isoform 2 of AP-2 complex subunit alpha-2 OS = *Homo sapiens* OX = 9606 GN = AP2A2 | 104 kDa | 2 | 8 | 0 | 3 |
| Isoform 2 of ATP-binding cassette sub-family F member 1 OS = *Homo sapiens* OX = 9606 GN = ABCF1 | 92 kDa | 2 | 6 | 2 | 2 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 2 of cAMP-dependent protein kinase type II-alpha regulatory subunit OS = *Homo sapiens* OX = 9606 GN = PRKAR2A | 43 kDa | 2 | 11 | 0 | 3 |
| Isoform 2 of Chromatin target of PRMT1 protein OS = *Homo sapiens* OX = 9606 GN = CHTOP | 27 kDa | 2 | 4 | 2 | 2 |
| Isoform 2 of Collagen alpha-1(XXII) chain OS = *Homo sapiens* OX = 9606 GN = COL22A1 | 159 kDa | 2 | 0 | 0 | 1 |
| Isoform 2 of DNA repair protein RAD50 OS = *Homo sapiens* OX = 9606 GN = RAD50 | 155 kDa | 2 | 0 | 0 | 1 |
| Isoform 2 of E3 ubiquitin-protein ligase RNF213 OS = *Homo sapiens* OX = 9606 GN = RNF213 | 596 kDa | 2 | 0 | 0 | 1 |
| Isoform 2 of Electron transfer flavoprotein subunit alpha, mitochondrial OS = *Homo sapiens* OX = 9606 GN = ETFA | 30 kDa | 2 | 1 | 0 | 5 |
| Isoform 2 of Enoyl-CoA delta isomerase 2, mitochondrial OS = *Homo sapiens* OX = 9606 GN = ECI2 | 40 kDa | 2 | 0 | 0 | 0 |
| Isoform 2 of Eukaryotic peptide chain release factor subunit 1 OS = *Homo sapiens* OX = 9606 GN = ETF1 | 45 kDa | 2 | 2 | 0 | 2 |
| Isoform 2 of Eukaryotic translation initiation factor 3 subunit D OS = *Homo sapiens* OX = 9606 GN = EIF3D | 58 kDa | 2 | 2 | 0 | 0 |
| Isoform 2 of Fermitin family homolog 2 OS = *Homo sapiens* OX = 9606 GN = FERMT2 | 72 kDa | 2 | 0 | 0 | 6 |
| Isoform 2 of Glutamine--fructose-6-phosphate aminotransferase [isomerizing] 1 OS = *Homo sapiens* OX = 9606 GN = GFPT1 | 77 kDa | 2 | 5 | 0 | 1 |
| Isoform 2 of Guanine nucleotide-binding protein-like 3 OS = *Homo sapiens* OX = 9606 GN = GNL3 | 61 kDa | 2 | 3 | 0 | 0 |
| Isoform 2 of Histidine--tRNA ligase, cytoplasmic OS = *Homo sapiens* OX = 9606 GN = HARS | 53 kDa | 2 | 3 | 0 | 4 |
| Isoform 2 of Histone H1.0 OS = *Homo sapiens* OX = 9606 GN = H1F0 | 19 kDa | 2 | 1 | 3 | 3 |
| Isoform 2 of Interferon-induced, double-stranded RNA-activated protein kinase OS = *Homo sapiens* OX = 9606 GN = EIF2AK2 | 57 kDa | 2 | 1 | 0 | 1 |
| Isoform 2 of Neurotrimin OS = *Homo sapiens* OX = 9606 GN = NTM | 38 kDa | 2 | 0 | 0 | 0 |
| Isoform 2 of Neutral cholesterol ester hydrolase 1 OS = *Homo sapiens* OX = 9606 GN = NCEH1 | 47 kDa | 2 | 1 | 0 | 3 |
| Isoform 2 of Nucleosome assembly protein 1-like 1 OS = *Homo sapiens* OX = 9606 GN = NAP1L1 | 43 kDa | 2 | 10 | 1 | 3 |
| Isoform 2 of Nucleosome assembly protein 1-like 4 OS = *Homo sapiens* OX = 9606 GN = NAP1L4 | 44 kDa | 2 | 0 | 0 | 3 |
| Isoform 2 of Polyadenylate-binding protein 2 OS = *Homo sapiens* OX = 9606 GN = PABPN1 | 31 kDa | 2 | 7 | 0 | 2 |
| Isoform 2 of Pre-mRNA-splicing factor SYF2 OS = *Homo sapiens* OX = 9606 GN = SYF2 | 24 kDa | 2 | 0 | 0 | 3 |
| Isoform 2 of Procollagen-lysine,2-oxoglutarate 5-dioxygenase 1 OS = *Homo sapiens* OX = 9606 GN = PLOD1 | 88 kDa | 2 | 12 | 0 | 1 |
| Isoform 2 of Procollagen-lysine,2-oxoglutarate 5-dioxygenase 2 OS = *Homo sapiens* OX = 9606 GN = PLOD2 | 87 kDa | 2 | 2 | 0 | 0 |
| Isoform 2 of Protein enabled homolog OS = *Homo sapiens* OX = 9606 GN = ENAH | 64 kDa | 2 | 26 | 1 | 18 |
| Isoform 2 of Protein SGT1 homolog OS = *Homo sapiens* OX = 9606 GN = SUGT1 | 38 kDa | 2 | 0 | 0 | 0 |
| Isoform 2 of Protein transport protein Sec16A OS = *Homo sapiens* OX = 9606 GN = SEC16A | 229 kDa | 2 | 0 | 0 | 1 |
| Isoform 2 of RNA-binding protein with serine-rich domain 1 OS = *Homo sapiens* OX = 9606 GN = RNPS1 | 32 kDa | 2 | 3 | 1 | 2 |
| Isoform 2 of Signal recognition particle subunit SRP68 OS = *Homo sapiens* OX = 9606 GN = SRP68 | 67 kDa | 2 | 9 | 0 | 0 |
| Isoform 2 of Syntenin-1 OS = *Homo sapiens* OX = 9606 GN = SDCBP | 32 kDa | 2 | 6 | 0 | 0 |
| Isoform 2 of Translocating chain-associated membrane protein 1 OS = *Homo sapiens* OX = 9606 GN = TRAM1 | 40 kDa | 2 | 6 | 4 | 5 |
| Isoform 2 of Trifunctional enzyme subunit beta, mitochondrial OS = *Homo sapiens* OX = 9606 GN = HADHB | 49 kDa | 2 | 51 | 9 | 10 |
| Isoform 2 of UDP-glucose: glycoprotein glucosyltransferase 1 OS = *Homo sapiens* OX = 9606 GN = UGGT1 | 175 kDa | 2 | 2 | 0 | 1 |
| Isoform 3 of 28S ribosomal protein S29, mitochondrial OS = *Homo sapiens* GN = DAP3 | 42 kDa | 2 | 5 | 2 | 1 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 3 of Basic leucine zipper and W2 domain-containing protein 1 OS = *Homo sapiens* OX = 9606 GN = BZW1 | 51 kDa | 2 | 1 | 0 | 4 |
| Isoform 3 of E3 ubiquitin-protein ligase HUWE1 OS = *Homo sapiens* GN = HUWE1 | 481 kDa | 2 | 4 | 0 | 0 |
| Isoform 3 of Heterogeneous nuclear ribonucleoprotein H3 OS = *Homo sapiens* GN = HNRNPH3 | 32 kDa | 2 | 8 | 0 | 3 |
| Isoform 3 of Integrin-linked protein kinase OS = *Homo sapiens* OX = 9606 GN = ILK | 36 kDa | 2 | 0 | 0 | 2 |
| Isoform 3 of Protein virilizer homolog OS = *Homo sapiens* OX = 9606 GN = VIRMA | 201 kDa | 2 | 0 | 0 | 0 |
| Isoform 3 of Ubiquitin-associated protein 2-like OS = *Homo sapiens* OX = 9606 GN = UBAP2L | 113 kDa | 2 | 7 | 0 | 7 |
| Isoform 4 of LIM domain and actin-binding protein 1 OS = *Homo sapiens* OX = 9606 GN = LIMA1 | 85 kDa | 2 | 49 | 6 | 4 |
| Isoform 4 of WASH complex subunit 2C OS = *Homo sapiens* OX = 9606 GN = WASHC2C | 145 kDa | 2 | 0 | 0 | 0 |
| Isoform Delta 10 of Calcium/calmodulin-dependent protein kinase type II subunit delta OS = *Homo sapiens* OX = 9606 GN = CAMK2D | 56 kDa | 2 | 5 | 0 | 0 |
| Isoform LAMP-2B of Lysosome-associated membrane glycoprotein 2 OS = *Homo sapiens* OX = 9606 GN = LAMP2 | 45 kDa | 2 | 0 | 0 | 2 |
| Leucine-rich repeat flightless-interacting protein 1 OS = *Homo sapiens* OX = 9606 GN = LRRFIP1 PE = 1 SV = 2 | 89 kDa | 2 | 0 | 0 | 1 |
| Lysophospholipid acyltransferase 7 OS = *Homo sapiens* GN = MBOAT7 PE = 1 SV = 2 | 53 kDa | 2 | 2 | 0 | 0 |
| Microsomal glutathione S-transferase 3 OS = *Homo sapiens* OX = 9606 GN = MGST3 PE = 1 SV = 1 | 17 kDa | 2 | 1 | 1 | 2 |
| Mitochondrial import receptor subunit TOM40 homolog OS = *Homo sapiens* OX = 9606 GN = TOMM40 PE = 1 SV = 1 | 38 kDa | 2 | 0 | 0 | 0 |
| Mucin-19 OS = *Homo sapiens* OX = 9606 GN = MUC19 PE = 1 SV = 3 | 805 kDa | 2 | 0 | 0 | 0 |
| NADH dehydrogenase [ubiquinone] iron-sulfur protein 3, mitochondrial OS = *Homo sapiens* OX = 9606 GN = NDUFS3 PE = 1 SV = 1 | 30 kDa | 2 | 4 | 0 | 4 |
| Nascent polypeptide-associated complex subunit alpha, muscle-specific form OS = *Homo sapiens* OX = 9606 GN = NACA PE = 1 SV = 1 | 205 kDa | 2 | 6 | 0 | 4 |
| Nicotinamide phosphoribosyltransferase OS = *Homo sapiens* OX = 9606 GN = NAMPT PE = 1 SV = 1 | 56 kDa | 2 | 2 | 0 | 3 |
| Non-histone chromosomal protein HMG-14 OS = *Homo sapiens* OX = 9606 GN = HMGN1 PE = 1 SV = 1 | 12 kDa | 2 | 11 | 3 | 6 |
| Nucleolar protein 11 OS = *Homo sapiens* OX = 9606 GN = NOL11 PE = 1 SV = 1 | 81 kDa | 2 | 0 | 0 | 0 |
| Obg-like ATPase 1 OS = *Homo sapiens* OX = 9606 GN = OLA1 PE = 1 SV = 2 | 45 kDa | 2 | 4 | 0 | 3 |
| PDZ and LIM domain protein 5 OS = *Homo sapiens* GN = PDLIM5 PE = 1 SV = 5 | 64 kDa | 2 | 3 | 0 | 2 |
| Peroxiredoxin-2 OS = *Homo sapiens* OX = 9606 GN = PRDX2 PE = 1 SV = 5 | 22 kDa | 2 | 7 | 0 | 1 |
| Phospholipid-transporting ATPase IB OS = *Homo sapiens* OX = 9606 GN = ATP8A2 PE = 1 SV = 3 | 129 kDa | 2 | 0 | 2 | 0 |
| Phosphoserine aminotransferase OS = *Homo sapiens* OX = 9606 GN = PSAT1 PE = 1 SV = 2 | 40 kDa | 2 | 0 | 0 | 0 |
| Plasminogen activator inhibitor 1 OS = *Homo sapiens* OX = 9606 GN = SERPINE1 PE = 1 SV = 1 | 45 kDa | 2 | 90 | 41 | 29 |
| pre-rRNA processing protein FTSJ3 OS = *Homo sapiens* OX = 9606 GN = FTSJ3 PE = 1 SV = 2 | 97 kDa | 2 | 3 | 0 | 1 |
| PRKC apoptosis WT1 regulator protein OS = *Homo sapiens* OX = 9606 GN = PAWR PE = 1 SV = 1 | 37 kDa | 2 | 0 | 1 | 6 |
| Proteasome activator complex subunit 2 OS = *Homo sapiens* OX = 9606 GN = PSME2 PE = 1 SV = 4 | 27 kDa | 2 | 0 | 0 | 2 |
| Proteasome subunit alpha type-5 OS = *Homo sapiens* OX = 9606 GN = PSMA5 PE = 1 SV = 3 | 26 kDa | 2 | 2 | 0 | 2 |
| Proteasome subunit alpha type-7 OS = *Homo sapiens* OX = 9606 GN = PSMA7 PE = 1 SV = 1 | 28 kDa | 2 | 7 | 0 | 2 |
| Proteasome subunit beta type-2 OS = *Homo sapiens* OX = 9606 GN = PSMB2 PE = 1 SV = 1 | 23 kDa | 2 | 0 | 0 | 4 |
| Protein flightless-1 homolog OS = *Homo sapiens* OX = 9606 GN = FLII PE = 1 SV = 2 | 145 kDa | 2 | 0 | 0 | 1 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Protein SEC13 homolog OS = *Homo sapiens* OX = 9606 GN = SEC13 PE = 1 SV = 3 | 36 kDa | 2 | 4 | 0 | 4 |
| Ras-related protein Rab-5C OS = *Homo sapiens* OX = 9606 GN = RAB5C PE = 1 SV = 2 | 23 kDa | 2 | 7 | 0 | 3 |
| Ras-related protein Rab-7a OS = *Homo sapiens* OX = 9606 GN = RAB7A PE = 1 SV = 1 | 23 kDa | 2 | 0 | 0 | 2 |
| Remodeling and spacing factor 1 OS = *Homo sapiens* GN = RSF1 PE = 1 SV = 2 | 164 kDa | 2 | 9 | 0 | 0 |
| Serine beta-lactamase-like protein LACTB, mitochondrial OS = *Homo sapiens* OX = 9606 GN = LACTB PE = 1 SV = 2 | 61 kDa | 2 | 13 | 5 | 3 |
| Serine/arginine-rich splicing factor 1 OS = *Homo sapiens* GN = SRSF1 PE = 1 SV = 2 | 28 kDa | 2 | 7 | 0 | 2 |
| Structural maintenance of chromosomes protein 1A OS = *Homo sapiens* OX = 9606 GN = SMC1A PE = 1 SV = 2 | 143 kDa | 2 | 7 | 0 | 0 |
| SWISS-PROT: P02777 (Bos taurus) similar to Platelet factor 4 | 24 kDa | 2 | 3 | 3 | 3 |
| SWISS-PROT: Q2UVX4 (Bos taurus) Complement C3 precursor | 187 kDa | 2 | 7 | 6 | 4 |
| SWISS-PROT: Q95121 (Bos taurus) Pigment epithelium-derived factor precursor | 46 kDa | 2 | 0 | 3 | 3 |
| Transaldolase OS = *Homo sapiens* OX = 9606 GN = TALDO1 PE = 1 SV = 2 | 38 kDa | 2 | 0 | 0 | 3 |
| Translationally-controlled tumor protein OS = *Homo sapiens* OX = 9606 GN = TPT1 PE = 1 SV = 1 | 20 kDa | 2 | 0 | 0 | 2 |
| Translocon-associated protein subunit alpha OS = *Homo sapiens* OX = 9606 GN = SSR1 PE = 1 SV = 3 | 32 kDa | 2 | 5 | 3 | 5 |
| Transmembrane emp24 domain-containing protein 10 OS = *Homo sapiens* OX = 9606 GN = TMED10 PE = 1 SV = 2 | 25 kDa | 2 | 0 | 6 | 8 |
| Transmembrane emp24 domain-containing protein 9 OS = *Homo sapiens* OX = 9606 GN = TMED9 PE = 1 SV = 2 | 27 kDa | 2 | 0 | 1 | 2 |
| TREMBL: Q1RMN8 (Bos taurus) Similar to Immunoglobulin lambda-like polypeptide 1 | 25 kDa | 2 | 0 | 0 | 0 |
| Tripeptidyl-peptidase 1 OS = *Homo sapiens* GN = TPP1 PE = 1 SV = 2 | 61 kDa | 2 | 0 | 2 | 3 |
| 1,4-alpha-glucan-branching enzyme OS = *Homo sapiens* OX = 9606 GN = GBE1 PE = 1 SV = 3 | 80 kDa | 1 | 0 | 0 | 3 |
| 1-phosphatidylinositol 4,5-bisphosphate phosphodiesterase beta-3 OS = *Homo sapiens* GN = PLCB3 PE = 1 SV = 2 | 139 kDa | 1 | 0 | 0 | 2 |
| 28S ribosomal protein S35, mitochondrial OS = *Homo sapiens* GN = MRPS35 PE = 1 SV = 1 | 37 kDa | 1 | 2 | 0 | 2 |
| 40S ribosomal protein S30 OS = *Homo sapiens* OX = 9606 GN = FAU PE = 1 SV = 1 | 7 kDa | 1 | 0 | 3 | 2 |
| 60S ribosomal protein L11 OS = *Homo sapiens* OX = 9606 GN = RPL11 PE = 1 SV = 2 | 20 kDa | 1 | 18 | 1 | 3 |
| 60S ribosomal protein L35a OS = *Homo sapiens* OX = 9606 GN = RPL35A PE = 1 SV = 2 | 13 kDa | 1 | 0 | 2 | 2 |
| 60S ribosomal protein L37a OS = *Homo sapiens* OX = 9606 GN = RPL37A PE = 1 SV = 2 | 10 kDa | 1 | 0 | 5 | 5 |
| Alpha-parvin OS = *Homo sapiens* OX = 9606 GN = PARVA PE = 1 SV = 1 | 42 kDa | 1 | 3 | 0 | 4 |
| AT-rich interactive domain-containing protein 1A OS = *Homo sapiens* OX = 9606 GN = ARID1 A PE = 1 SV = 3 | 242 kDa | 1 | 3 | 0 | 0 |
| Basigin OS = *Homo sapiens* OX = 9606 GN = BSG PE = 1 SV = 2 | 42 kDa | 1 | 3 | 0 | 1 |
| Biorientation of chromosomes in cell division protein 1-like 1 OS = *Homo sapiens* OX = 9606 GN = BOD1L1 PE = 1 SV = 2 | 330 kDa | 1 | 0 | 0 | 3 |
| Cell division cycle 5-like protein OS = *Homo sapiens* OX = 9606 GN = CDC5L PE = 1 SV = 2 | 92 kDa | 1 | 3 | 0 | 4 |
| Coactosin-like protein OS = *Homo sapiens* OX = 9606 GN = COTL1 PE = 1 SV = 3 | 16 kDa | 1 | 0 | 0 | 2 |
| Collagen alpha-1(III) chain OS = *Homo sapiens* OX = 9606 GN = COL3A1 PE = 1 SV = 4 | 139 kDa | 1 | 2 | 0 | 1 |
| Collagen alpha-2(I) chain OS = *Homo sapiens* OX = 9606 GN = COL1A2 PE = 1 SV = 7 | 129 kDa | 1 | 12 | 7 | 3 |
| Collagen alpha-2(V) chain OS = *Homo sapiens* OX = 9606 GN = COL5A2 PE = 1 SV = 3 | 145 kDa | 1 | 0 | 15 | 6 |
| Collagen alpha-6(VI) chain OS = *Homo sapiens* OX = 9606 GN = COL6A6 PE = 1 SV = 2 | 247 kDa | 1 | 0 | 3 | 2 |
| Complement component 1 Q subcomponent-binding protein, mitochondrial OS = *Homo sapiens* OX = 9606 | 31 kDa | 1 | 0 | 0 | 4 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| GN = C1QBP PE = 1 SV = 1 | | | | | |
| Cysteine and glycine-rich protein 1 OS = *Homo sapiens* OX = 9606 GN = CSRP1 PE = 1 SV = 3 | 21 kDa | 1 | 0 | 0 | 2 |
| Cytochrome b-c1 complex subunit 9 OS = *Homo sapiens* OX = 9606 GN = UQCR10 PE = 1 SV = 3 | 7 kDa | 1 | 2 | 0 | 2 |
| Cytochrome c1, heme protein, mitochondrial OS = *Homo sapiens* OX = 9606 GN = CYC1 PE = 1 SV = 3 | 35 kDa | 1 | 0 | 0 | 3 |
| DDRGK domain-containing protein 1 OS = *Homo sapiens* OX = 9606 GN = DDRGK1 PE = 1 SV = 2 | 36 kDa | 1 | 0 | 1 | 2 |
| Destrin OS = *Homo sapiens* OX = 9606 GN = DSTN PE = 1 SV = 3 | 19 kDa | 1 | 3 | 0 | 6 |
| Dihydrolipoyl dehydrogenase, mitochondrial OS = *Homo sapiens* OX = 9606 GN = DLD PE = 1 SV = 2 | 54 kDa | 1 | 8 | 0 | 2 |
| DNA-directed RNA polymerases I, II, and III subunit RPABC1 OS = *Homo sapiens* OX = 9606 GN = POLR2E PE = 1 SV = 4 | 25 kDa | 1 | 0 | 5 | 1 |
| ELAV-like protein 1 OS = *Homo sapiens* OX = 9606 GN = ELAVL1 PE = 1 SV = 2 | 36 kDa | 1 | 3 | 0 | 1 |
| Eukaryotic translation initiation factor 3 subunit G OS = *Homo sapiens* OX = 9606 GN = EIF3G PE = 1 SV = 2 | 36 kDa | 1 | 0 | 0 | 3 |
| Farnesyl pyrophosphate synthase OS = *Homo sapiens* OX = 9606 GN = FDPS PE = 1 SV = 4 | 48 kDa | 1 | 3 | 0 | 1 |
| Fibrillin-1 OS = *Homo sapiens* OX = 9606 GN = FBN1 PE = 1 SV = 3 | 312 kDa | 1 | 0 | 2 | 0 |
| Fumarate hydratase, mitochondrial OS = *Homo sapiens* GN = FH PE = 1 SV = 3 | 55 kDa | 1 | 0 | 0 | 2 |
| Growth/differentiation factor 15 OS = *Homo sapiens* OX = 9606 GN = GDF15 PE = 1 SV = 3 | 34 kDa | 1 | 0 | 7 | 6 |
| Histone deacetylase complex subunit SAP18 OS = *Homo sapiens* OX = 9606 GN = SAP18 PE = 1 SV = 1 | 20 kDa | 1 | 0 | 0 | 2 |
| Histone H1x OS = *Homo sapiens* OX = 9606 GN = H1FX PE = 1 SV = 1 | 22 kDa | 1 | 0 | 0 | 2 |
| Hydrocephalus-inducing protein homolog OS = *Homo sapiens* OX = 9606 GN = HYDIN PE = 1 SV = 3 | 576 kDa | 1 | 0 | 1 | 0 |
| Insulin-like growth factor 2 mRNA-binding protein 3 OS = *Homo sapiens* GN = IGF2BP3 PE = 1 SV = 2 | 64 kDa | 1 | 18 | 2 | 0 |
| Isoform 2 of Adipocyte plasma membrane-associated protein OS = *Homo sapiens* OX = 9606 GN = APMAP | 32 kDa | 1 | 0 | 0 | 3 |
| Isoform 2 of Aspartate aminotransferase, mitochondrial OS = *Homo sapiens* OX = 9606 GN = GOT2 | 43 kDa | 1 | 0 | 0 | 3 |
| Isoform 2 of BH3-interacting domain death agonist OS = *Homo sapiens* OX = 9606 GN = BID | 27 kDa | 1 | 4 | 0 | 0 |
| Isoform 2 of DnaJ homolog subfamily A member 3, mitochondrial OS = *Homo sapiens* OX = 9606 GN = DNAJA3 | 50 kDa | 1 | 0 | 0 | 3 |
| Isoform 2 of Glia-derived nexin OS = *Homo sapiens* OX = 9606 GN = SERPINE2 | 44 kDa | 1 | 8 | 0 | 0 |
| Isoform 2 of Histone deacetylase 2 OS = *Homo sapiens* OX = 9606 GN = HDAC2 | 52 kDa | 1 | 4 | 0 | 1 |
| Isoform 2 of Lysosomal protective protein OS = *Homo sapiens* OX = 9606 GN = CTSA | 52 kDa | 1 | 1 | 0 | 2 |
| Isoform 2 of Lysosome membrane protein 2 OS = *Homo sapiens* OX = 9606 GN = SCARB2 | 38 kDa | 1 | 4 | 0 | 0 |
| Isoform 2 of Myosin phosphatase Rho-interacting protein OS = *Homo sapiens* OX = 9606 GN = MPRIP | 118 kDa | 1 | 13 | 0 | 0 |
| Isoform 2 of NADH dehydrogenase [ubiquinone] 1 alpha subcomplex subunit 13 OS = *Homo sapiens* OX = 9606 GN = NDUFA13 | 25 kDa | 1 | 13 | 1 | 3 |
| Isoform 2 of NADH dehydrogenase [ubiquinone] iron-sulfur protein 2, mitochondrial OS = *Homo sapiens* OX = 9606 GN = NDUFS2 | 52 kDa | 1 | 5 | 0 | 1 |
| Isoform 2 of Nesprin-2 OS = *Homo sapiens* OX = 9606 GN = SYNE2 | 799 kDa | 1 | 12 | 1 | 0 |
| Isoform 2 of Nuclear pore complex protein Nup214 OS = *Homo sapiens* OX = 9606 GN = NUP214 | 213 kDa | 1 | 0 | 0 | 3 |
| Isoform 2 of Phenylalanine--tRNA ligase alpha subunit OS = *Homo sapiens* OX = 9606 GN = FARSA | 54 kDa | 1 | 7 | 1 | 4 |
| Isoform 2 of Probable 28S rRNA (cytosine(4447)-C(5))-methyltransferase OS = *Homo sapiens* OX = 9606 GN = NOP2 | 89 kDa | 1 | 6 | 0 | 6 |
| Isoform 2 of Protein FAM98A OS = *Homo sapiens* OX = 9606 GN = FAM98A | 55 kDa | 1 | 2 | 0 | 3 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Isoform 2 of Protein TFG OS = *Homo sapiens* OX = 9606 GN = TFG | 43 kDa | 1 | 4 | 0 | 4 |
| Isoform 2 of Pyruvate dehydrogenase E1 component subunit beta, mitochondrial OS = *Homo sapiens* OX = 9606 GN = PDHB | 37 kDa | 1 | 7 | 0 | 3 |
| Isoform 2 of UTP--glucose-1-phosphate uridylyltransferase OS = *Homo sapiens* OX = 9606 GN = UGP2 | 56 kDa | 1 | 3 | 0 | 7 |
| Isoform 2 of V-type proton ATPase 116 kDa subunit a isoform 1 OS = *Homo sapiens* OX = 9606 GN = ATP6V0A1 | 96 kDa | 1 | 11 | 0 | 3 |
| Isoform 2B of Cytoplasmic dynein 1 intermediate chain 2 OS = *Homo sapiens* OX = 9606 GN = DYNC1I2 | 71 kDa | 1 | 16 | 1 | 3 |
| Isoform 3 of Activating signal cointegrator 1 complex subunit 2 OS = *Homo sapiens* OX = 9606 GN = ASCC2 | 77 kDa | 1 | 6 | 0 | 1 |
| Isoform 3 of Apoptosis-inducing factor 1, mitochondrial OS = *Homo sapiens* OX = 9606 GN = AIFM1 | 66 kDa | 1 | 3 | 0 | 4 |
| Isoform 3 of Calumenin OS = *Homo sapiens* OX = 9606 GN = CALU | 38 kDa | 1 | 1 | 0 | 2 |
| Isoform 3 of Fragile X mental retardation syndrome-related protein 1 OS = *Homo sapiens* OX = 9606 GN = FXR1 | 60 kDa | 1 | 4 | 0 | 1 |
| Isoform 3 of GRB10-interacting GYF protein 2 OS = *Homo sapiens* OX = 9606 GN = GIGYF2 | 149 kDa | 1 | 0 | 0 | 0 |
| Isoform 3 of Pyrroline-5-carboxylate reductase 1, mitochondrial OS = *Homo sapiens* OX = 9606 GN = PYCR1 | 36 kDa | 1 | 8 | 0 | 0 |
| Isoform 3 of Ras-related protein R-Ras2 OS = *Homo sapiens* GN = RRAS2 | 20 kDa | 1 | 5 | 0 | 1 |
| Isoform 3 of Signal peptidase complex catalytic subunit SEC11A OS = *Homo sapiens* OX = 9606 GN = SEC11A | 21 kDa | 1 | 2 | 1 | 3 |
| Isoform 4 of Cadherin-13 OS = *Homo sapiens* OX = 9606 GN = CDH13 | 83 kDa | 1 | 23 | 6 | 2 |
| Isoform 4 of Dipeptidyl peptidase 3 OS = *Homo sapiens* OX = 9606 GN = DPP3 | 79 kDa | 1 | 0 | 0 | 2 |
| Isoform 4 of Dynamin-1-like protein OS = *Homo sapiens* OX = 9606 GN = DNM1L | 81 kDa | 1 | 2 | 0 | 2 |
| Isoform 4 of Dynamin-2 OS = *Homo sapiens* OX = 9606 GN = DNM2 | 98 kDa | 1 | 13 | 0 | 6 |
| Isoform 4 of Nexilin OS = *Homo sapiens* OX = 9606 GN = NEXN | 73 kDa | 1 | 28 | 12 | 7 |
| Isoform 5 of Obscurin OS = *Homo sapiens* OX = 9606 GN = OBSCN | 925 kDa | 1 | 0 | 0 | 1 |
| Isoform 6 of RNA-binding protein EWS OS = *Homo sapiens* OX = 9606 GN = EWSR1 | 63 kDa | 1 | 6 | 0 | 6 |
| Isoform Heart of ATP synthase subunit gamma, mitochondrial OS = *Homo sapiens* OX = 9606 GN = ATP5F1C | 33 kDa | 1 | 6 | 0 | 4 |
| Isoform Mitochondrial of Lysine--tRNA ligase OS = *Homo sapiens* OX = 9606 GN = KARS | 71 kDa | 1 | 4 | 0 | 1 |
| Leucine-rich repeat-containing protein 17 OS = *Homo sapiens* OX = 9606 GN = LRRC17 PE = 2 SV = 1 | 52 kDa | 1 | 11 | 9 | 4 |
| Leucyl-cystinyl aminopeptidase OS = *Homo sapiens* OX = 9606 GN = LNPEP PE = 1 SV = 3 | 117 kDa | 1 | 4 | 3 | 2 |
| LIM and SH3 domain protein 1 OS = *Homo sapiens* OX = 9606 GN = LASP1 PE = 1 SV = 2 | 30 kDa | 1 | 1 | 0 | 3 |
| Matrix metalloproteinase-14 OS = *Homo sapiens* OX = 9606 GN = MMP14 PE = 1 SV = 3 | 66 kDa | 1 | 0 | 0 | 2 |
| Microtubule-associated protein RP/EB family member 1 OS = *Homo sapiens* OX = 9606 GN = MAPRE1 PE = 1 SV = 3 | 30 kDa | 1 | 4 | 0 | 4 |
| Mitochondrial 2-oxoglutarate/malate carrier protein OS = *Homo sapiens* OX = 9606 GN = SLC25A11 PE = 1 SV = 3 | 34 kDa | 1 | 7 | 0 | 1 |
| Mitochondrial fission 1 protein OS = *Homo sapiens* OX = 9606 GN = FIS1 PE = 1 SV = 2 | 17 kDa | 1 | 0 | 0 | 3 |
| NADH dehydrogenase [ubiquinone] 1 alpha subcomplex subunit 12 OS = *Homo sapiens* OX = 9606 GN = NDUFA12 PE = 1 SV = 1 | 17 kDa | 1 | 6 | 1 | 2 |
| PDZ domain-containing protein 4 OS = *Homo sapiens* OX = 9606 GN = PDZD4 PE = 1 SV = 1 | 86 kDa | 1 | 0 | 0 | 0 |
| Peroxisomal membrane protein PEX14 OS = *Homo sapiens* OX = 9606 GN = PEX14 PE = 1 SV = 1 | 41 kDa | 1 | 3 | 0 | 2 |
| Platelet-activating factor acetylhydrolase IB subunit beta OS = *Homo sapiens* GN = PAFAH1B2 PE = 1 SV = 1 | 26 kDa | 1 | 6 | 0 | 1 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Podocalyxin OS = *Homo sapiens* GN = PODXL PE = 1 SV = 2 | 59 kDa | 1 | 0 | 0 | 2 |
| Prolyl 3-hydroxylase 3 OS = *Homo sapiens* OX = 9606 GN = P3H3 PE = 1 SV = 1 | 82 kDa | 1 | 0 | 0 | 2 |
| Prolyl 4-hydroxylase subunit alpha-2 OS = *Homo sapiens* OX = 9606 GN = P4HA2 PE = 1 SV = 1 | 61 kDa | 1 | 2 | 0 | 0 |
| Proteasome subunit alpha type-6 OS = *Homo sapiens* OX = 9606 GN = PSMA6 PE = 1 SV = 1 | 27 kDa | 1 | 8 | 0 | 1 |
| Proteasome subunit beta type-5 OS = *Homo sapiens* GN = PSMB5 PE = 1 SV = 3 | 28 kDa | 1 | 2 | 0 | 0 |
| Protein CYR61 OS = *Homo sapiens* OX = 9606 GN = CYR61 PE = 1 SV = 1 | 42 kDa | 1 | 0 | 27 | 24 |
| Protein mago nashi homolog OS = *Homo sapiens* OX = 9606 GN = MAGOH PE = 1 SV = 1 | 17 kDa | 1 | 7 | 0 | 0 |
| RNA-binding protein 14 OS = *Homo sapiens* OX = 9606 GN = RBM14 PE = 1 SV = 2 | 69 kDa | 1 | 18 | 2 | 5 |
| RuvB-like 1 OS = *Homo sapiens* OX = 9606 GN = RUVBL1 PE = 1 SV = 1 | 50 kDa | 1 | 18 | 0 | 2 |
| Splicing factor 3B subunit 4 OS = *Homo sapiens* OX = 9606 GN = SF3B4 PE = 1 SV = 1 | 44 kDa | 1 | 0 | 0 | 2 |
| Splicing factor U2AF 26 kDa subunit OS = *Homo sapiens* OX = 9606 GN = U2AF1L4 PE = 4 SV = 1 | 4 kDa | 1 | 0 | 2 | 1 |
| SWISS-PROT: P04258 (Bos taurus) Similar to Collagen alpha 1(III) chain | 138 kDa | 1 | 9 | 0 | 0 |
| TREMBL: A2I7N3; Q27984 (Bos taurus) SERPINA3-7 | 47 kDa | 1 | 5 | 1 | 1 |
| Unconventional myosin-Ie OS = *Homo sapiens* OX = 9606 GN = MYO1E PE = 1 SV = 2 | 127 kDa | 1 | 20 | 5 | 4 |
| Vacuolar protein sorting-associated protein VTA1 homolog OS = *Homo sapiens* OX = 9606 GN = VTA1 PE = 1 SV = 1 | 34 kDa | 1 | 0 | 0 | 2 |
| Very-long-chain (3R)-3-hydroxyacyl-CoA dehydratase 3 OS = *Homo sapiens* GN = HACD3 PE = 1 SV = 2 | 43 kDa | 1 | 8 | 1 | 2 |
| von Willebrand factor A domain-containing protein 1 OS = *Homo sapiens* OX = 9606 GN = VWA1 PE = 1 SV = 1 | 47 kDa | 1 | 7 | 0 | 0 |
| (Bos taurus) 63 kDa protein | 63 kDa | 0 | 55 | 0 | 0 |
| 10 kDa heat shock protein, mitochondrial OS = *Homo sapiens* GN = HSPE1 PE = 1 SV = 2 | 11 kDa | 0 | 6 | 0 | 0 |
| 1-phosphatidylinositol 3-phosphate 5-kinase OS = *Homo sapiens* OX = 9606 GN = PIKFYVE PE = 1 SV = 3 | 237 kDa | 0 | 0 | 0 | 2 |
| 26S protease regulatory subunit 10B OS = *Homo sapiens* GN = PSMC6 PE = 1 SV = 1 | 46 kDa | 0 | 9 | 0 | 0 |
| 26S protease regulatory subunit 6A OS = *Homo sapiens* GN = PSMC3 PE = 1 SV = 3 | 49 kDa | 0 | 30 | 0 | 0 |
| 26S proteasome non-ATPase regulatory subunit 14 OS = *Homo sapiens* GN = PSMD14 PE = 1 SV = 1 | 35 kDa | 0 | 17 | 0 | 0 |
| 26S proteasome non-ATPase regulatory subunit 8 OS = *Homo sapiens* GN = PSMD8 PE = 1 SV = 1 | 33 kDa | 0 | 3 | 0 | 0 |
| 28S ribosomal protein S34, mitochondrial OS = *Homo sapiens* GN = MRPS34 PE = 1 SV = 2 | 26 kDa | 0 | 2 | 0 | 0 |
| 39S ribosomal protein L11, mitochondrial OS = *Homo sapiens* GN = MRPL11 PE = 1 SV = 1 | 21 kDa | 0 | 7 | 0 | 1 |
| 39S ribosomal protein L34, mitochondrial OS = *Homo sapiens* GN = MRPL34 PE = 1 SV = 1 | 20 kDa | 0 | 8 | 0 | 0 |
| 3-ketoacyl-CoA thiolase, mitochondrial OS = *Homo sapiens* OX = 9606 GN = ACAA2 PE = 1 SV = 2 | 42 kDa | 0 | 0 | 0 | 2 |
| 40S ribosomal protein S13 OS = *Homo sapiens* OX = 9606 GN = RPS13 PE = 1 SV = 2 | 17 kDa | 0 | 85 | 19 | 19 |
| 40S ribosomal protein S15a OS = *Homo sapiens* GN = RPS15A PE = 1 SV = 1 | 11 kDa | 0 | 25 | 0 | 0 |
| 40S ribosomal protein S18 OS = *Homo sapiens* GN = RPS18 PE = 1 SV = 3 | 18 kDa | 0 | 51 | 0 | 0 |
| 40S ribosomal protein S28 OS = *Homo sapiens* GN = RPS28 PE = 1 SV = 1 | 8 kDa | 0 | 6 | 0 | 0 |
| 40S ribosomal protein S29 OS = *Homo sapiens* OX = 9606 GN = RPS29 PE = 1 SV = 2 | 7 kDa | 0 | 16 | 1 | 1 |
| 40S ribosomal protein S3a OS = *Homo sapiens* GN = RPS3A PE = 1 SV = 2 | 30 kDa | 0 | 53 | 0 | 0 |
| 40S ribosomal protein S4, Y isoform 1 OS = *Homo sapiens* OX = 9606 GN = RPS4Y1 PE = 1 SV = 2 | 29 kDa | 0 | 0 | 0 | 9 |
| 40S ribosomal protein SA (Fragment) OS = *Homo sapiens* GN = RPSA PE = 1 SV = 8 | 29 kDa | 0 | 8 | 0 | 0 |
| 60S acidic ribosomal protein P2 OS = *Homo sapiens* GN = RPLP2 PE = 1 SV = 1 | 12 kDa | 0 | 50 | 0 | 0 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| 60S ribosomal protein L13a OS = *Homo sapiens* GN = RPL13A PE = 1 SV = 2 | 24 kDa | 0 | 33 | 0 | 0 |
| 60S ribosomal protein L14 OS = *Homo sapiens* GN = RPL14 PE = 1 SV = 4 | 23 kDa | 0 | 34 | 0 | 0 |
| 60S ribosomal protein L18a OS = *Homo sapiens* GN = RPL18A PE = 1 SV = 2 | 21 kDa | 0 | 31 | 0 | 0 |
| 60S ribosomal protein L23a (Fragment) OS = *Homo sapiens* GN = RPL23A PE = 1 SV = 1 | 18 kDa | 0 | 32 | 0 | 0 |
| 60S ribosomal protein L29 OS = *Homo sapiens* GN = RPL29 PE = 1 SV = 2 | 18 kDa | 0 | 6 | 0 | 0 |
| 60S ribosomal protein L32 (Fragment) OS = *Homo sapiens* GN = RPL32 PE = 1 SV = 1 | 16 kDa | 0 | 20 | 0 | 0 |
| 60S ribosomal protein L34 OS = *Homo sapiens* OX = 9606 GN = RPL34 PE = 1 SV = 3 | 13 kDa | 0 | 0 | 3 | 3 |
| 60S ribosomal protein L35 OS = *Homo sapiens* GN = RPL35 PE = 1 SV = 2 | 15 kDa | 0 | 24 | 0 | 0 |
| 60S ribosomal protein L38 OS = *Homo sapiens* OX = 9606 GN = RPL38 PE = 1 SV = 2 | 8 kDa | 0 | 0 | 5 | 4 |
| 78 kDa glucose-regulated protein OS = *Homo sapiens* GN = HSPA5 PE = 1 SV = 2 | 72 kDa | 0 | 188 | 0 | 0 |
| A disintegrin and metalloproteinase with thrombospondin motifs 1 OS = *Homo sapiens* OX = 9606 GN = ADAMTS1 PE = 1 SV = 4 | 105 kDa | 0 | 12 | 3 | 0 |
| Actin-related protein 10 OS = *Homo sapiens* GN = ACTR10 PE = 1 SV = 1 | 46 kDa | 0 | 3 | 0 | 0 |
| Actin-related protein 2/3 complex subunit 1B OS = *Homo sapiens* GN = ARPC1B PE = 1 SV = 3 | 41 kDa | 0 | 28 | 0 | 0 |
| ADP-ribosyl cyclase/cyclic ADP-ribose hydrolase 2 OS = *Homo sapiens* OX = 9606 GN = BST1 PE = 1 SV = 2 | 36 kDa | 0 | 3 | 5 | 2 |
| Aminopeptidase N OS = *Homo sapiens* GN = ANPEP PE = 1 SV = 4 | 110 kDa | 0 | 194 | 0 | 0 |
| Angiopoietin-related protein 4 OS = *Homo sapiens* OX = 9606 GN = ANGPTL4 PE = 1 SV = 2 | 45 kDa | 0 | 1 | 3 | 0 |
| Annexin A3 OS = *Homo sapiens* OX = 9606 GN = ANXA3 PE = 1 SV = 3 | 36 kDa | 0 | 0 | 0 | 3 |
| Annexin A4 OS = *Homo sapiens* OX = 9606 GN = ANXA4 PE = 1 SV = 4 | 36 kDa | 0 | 0 | 0 | 2 |
| AP-2 complex subunit sigma OS = *Homo sapiens* GN = AP2S1 PE = 1 SV = 1 | 19 kDa | 0 | 3 | 0 | 0 |
| Arf-GAP with Rho-GAP domain, ANK repeat and PH domain-containing protein 3 OS = *Homo sapiens* OX = 9606 GN = ARAP3 PE = 1 SV = 1 | 170 kDa | 0 | 0 | 0 | 2 |
| ATP synthase subunit epsilon-like protein, mitochondrial OS = *Homo sapiens* GN = ATP5EP2 PE = 3 SV = 1 | 6 kDa | 0 | 3 | 0 | 0 |
| ATP synthase subunit g, mitochondrial OS = *Homo sapiens* GN = ATP5L PE = 1 SV = 3 | 11 kDa | 0 | 6 | 0 | 0 |
| ATPase ASNA1 OS = *Homo sapiens* GN = ASNA1PE = 1 SV = 2 | 39 kDa | 0 | 2 | 0 | 0 |
| ATPase, H+ transporting, lysosomal accessory protein 1, isoform CRA_c OS = *Homo sapiens* GN = ATP6AP1 PE = 1 SV = 1 | 32 kDa | 0 | 7 | 0 | 0 |
| ATP-dependent DNA helicase Q1 OS = *Homo sapiens* GN = RECQL PE = 1 SV = 3 | 73 kDa | 0 | 2 | 0 | 0 |
| Barrier-to-autointegration factor OS = *Homo sapiens* GN = BANF1 PE = 1 SV = 1 | 10 kDa | 0 | 24 | 0 | 0 |
| Basement membrane-specific heparan sulfate proteoglycan core protein OS = *Homo sapiens* GN = HSPG2 PE = 1 SV = 4 | 469 kDa | 0 | 4914 | 0 | 0 |
| Beta-catenin-like protein 1 OS = *Homo sapiens* GN = CTNNBL1 PE = 1 SV = 1 | 65 kDa | 0 | 2 | 0 | 0 |
| Beta-galactosidase OS = *Homo sapiens* GN = GLB1 PE = 1 SV = 2 | 76 kDa | 0 | 3 | 0 | 0 |
| Biglycan OS = *Homo sapiens* OX = 9606 GN = BGN PE = 1 SV = 2 | 42 kDa | 0 | 0 | 23 | 0 |
| Bone morphogenetic protein 1 OS = *Homo sapiens* OX = 9606 GN = BMP1 PE = 1 SV = 2 | 111 kDa | 0 | 14 | 3 | 0 |
| Brain acid soluble protein 1 OS = *Homo sapiens* GN = BASP1 PE = 1 SV = 2 | 23 kDa | 0 | 10 | 0 | 0 |
| C-1-tetrahydrofolate synthase, cytoplasmic OS = *Homo sapiens* GN = MTHFD1 PE = 1 SV = 3 | 102 kDa | 0 | 2 | 0 | 0 |
| Calmodulin OS = *Homo sapiens* GN = CALM1 PE = 1 SV = 2 | 17 kDa | 0 | 24 | 0 | 0 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Calpain small subunit 1 OS = *Homo sapiens* GN = CAPNS1 PE = 1 SV = 1 | 34 kDa | 0 | 34 | 0 | 0 |
| Carboxypeptidase M OS = *Homo sapiens* GN = CPM PE = 1 SV = 2 | 51 kDa | 0 | 5 | 0 | 0 |
| Cardiomyopathy-associated protein 5 OS = *Homo sapiens* GN = CMYA5 PE = 1 SV = 3 | 449 kDa | 0 | 2 | 0 | 0 |
| Casein kinase II subunit alpha OS = *Homo sapiens* OX = 9606 GN = CSNK2A1 PE = 1 SV = 1 | 45 kDa | 0 | 10 | 1 | 1 |
| CD2-associated protein OS = *Homo sapiens* GN = CD2AP PE = 1 SV = 1 | 71 kDa | 0 | 9 | 0 | 0 |
| CD59 glycoprotein OS = *Homo sapiens* OX = 9606 GN = CD59 PE = 1 SV = 1 | 14 kDa | 0 | 0 | 3 | 0 |
| Chloride intracellular channel protein 4 OS = *Homo sapiens* GN = CLIC4 PE = 1 SV = 4 | 29 kDa | 0 | 2 | 0 | 0 |
| Chloride intracellular channel protein 6 OS = *Homo sapiens* GN = CLIC6 PE = 2 SV = 3 | 73 kDa | 0 | 2 | 0 | 0 |
| Chromobox protein homolog 1 (Fragment) OS = *Homo sapiens* GN = CBX1 PE = 1 SV = 1 | 19 kDa | 0 | 5 | 0 | 0 |
| Coiled-coil domain-containing protein 124 OS = *Homo sapiens* GN = CCDC124 PE = 1 SV = 1 | 26 kDa | 0 | 6 | 0 | 0 |
| Coiled-coil domain-containing protein 30 OS = *Homo sapiens* GN = CCDC30 PE = 2 SV = 1 | 91 kDa | 0 | 2 | 0 | 0 |
| Coiled-coil-helix-coiled-coil-helix domain-containing protein 1 OS = *Homo sapiens* GN = CHCHD1 PE = 1 SV = 1 | 13 kDa | 0 | 2 | 0 | 0 |
| Collagen alpha-1(II) chain OS = *Homo sapiens* OX = 9606 GN = COL2A1 PE = 1 SV = 3 | 142 kDa | 0 | 2 | 1 | 1 |
| Collagen alpha-1(VI) chain OS = *Homo sapiens* GN = COL6A1 PE = 1 SV = 1 | 108 kDa | 0 | 3 | 0 | 0 |
| Collagen alpha-1(X) chain OS = *Homo sapiens* GN = COL10A1 PE = 1 SV = 2 | 66 kDa | 0 | 3 | 0 | 0 |
| Collagen alpha-1(XXIII) chain OS = *Homo sapiens* GN = COL23A1 PE = 1 SV = 1 | 52 kDa | 0 | 2 | 0 | 0 |
| Collagen alpha-1(XXVII) chain OS = *Homo sapiens* OX = 9606 GN = COL27A1 PE = 1 SV = 1 | 187 kDa | 0 | 1 | 0 | 2 |
| Collagen alpha-2(IX) chain OS = *Homo sapiens* OX = 9606 GN = COL9A2 PE = 1 SV = 2 | 65 kDa | 0 | 0 | 0 | 0 |
| Collagen triple helix repeat-containing protein 1 OS = *Homo sapiens* OX = 9606 GN = CTHRC1 PE = 1 SV = 1 | 26 kDa | 0 | 3 | 1 | 1 |
| Connective tissue growth factor OS = *Homo sapiens* OX = 9606 GN = CTGF PE = 1 SV = 2 | 38 kDa | 0 | 4 | 6 | 2 |
| COP9 signalosome complex subunit 5 OS = *Homo sapiens* GN = COPS5 PE = 1 SV = 4 | 38 kDa | 0 | 2 | 0 | 0 |
| Coronin-1B OS = *Homo sapiens* GN = CORO1B PE = 1 SV = 1 | 54 kDa | 0 | 9 | 0 | 0 |
| Cullin-1 OS = *Homo sapiens* GN = CUL1 PE = 1 SV = 2 | 90 kDa | 0 | 3 | 0 | 0 |
| Cytochrome c (Fragment) OS = *Homo sapiens* GN = CYCS PE = 1 SV = 1 | 11 kDa | 0 | 3 | 0 | 0 |
| Cytochrome c oxidase subunit 4 isoform 1, mitochondrial OS = *Homo sapiens* GN = COX4I1 PE = 1 SV = 1 | 20 kDa | 0 | 5 | 0 | 0 |
| Cytoplasmic aconitate hydratase OS = *Homo sapiens* OX = 9606 GN = ACO1 PE = 1 SV = 3 | 98 kDa | 0 | 0 | 0 | 2 |
| Cytosolic non-specific dipeptidase OS = *Homo sapiens* OX = 9606 GN = CNDP2 PE = 1 SV = 2 | 53 kDa | 0 | 10 | 0 | 8 |
| Death-associated protein kinase 3 OS = *Homo sapiens* OX = 9606 GN = DAPK3 PE = 1 SV = 1 | 53 kDa | 0 | 6 | 0 | 0 |
| Deoxyribose-phosphate aldolase OS = *Homo sapiens* OX = 9606 GN = DERA PE = 1 SV = 2 | 35 kDa | 0 | 0 | 0 | 3 |
| Desmoglein-1 OS = *Homo sapiens* GN = DSG1 PE = 1 SV = 2 | 114 kDa | 0 | 6 | 0 | 0 |
| DNA damage-binding protein 1 OS = *Homo sapiens* OX = 9606 GN = DDB1 PE = 1 SV = 1 | 127 kDa | 0 | 14 | 0 | 3 |
| DNA topoisomerase 1 OS = *Homo sapiens* GN = TOP1 PE = 1 SV = 2 | 91 kDa | 0 | 10 | 0 | 0 |
| DNA-directed RNA polymerase II subunit RPB1 OS = *Homo sapiens* OX = 9606 GN = POLR2A PE = 1 SV = 2 | 217 kDa | 0 | 11 | 0 | 0 |
| DNA-directed RNA polymerase II subunit RPB2 OS = *Homo sapiens* GN = POLR2B PE = 1 SV = 1 | 134 kDa | 0 | 14 | 0 | 0 |
| DNA-directed RNA polymerase II subunit RPB3 OS = *Homo sapiens* GN = POLR2C PE = 1 SV = 2 | 31 kDa | 0 | 9 | 0 | 0 |
| DNA-directed RNA polymerase II subunit RPB4 OS = *Homo sapiens* GN = POLR2D PE = 1 SV = 1 | 13 kDa | 0 | 6 | 0 | 0 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| DNA-directed RNA polymerases I, II, and III subunit RPABC3 OS = *Homo sapiens* OX = 9606 GN = POLR2H PE = 1 SV = 4 | 17 kDa | 0 | 2 | 3 | 0 |
| DnaJ homolog subfamily B member 11 OS = *Homo sapiens* OX = 9606 GN = DNAJB11 PE = 1 SV = 1 | 41 kDa | 0 | 0 | 0 | 4 |
| Dolichol-phosphate mannosyltransferase subunit 1 OS = *Homo sapiens* GN = DPM1 PE = 1 SV = 1 | 30 kDa | 0 | 2 | 0 | 0 |
| Dolichyl-diphosphooligosaccharide--protein glycosyltransferase subunit STT3B OS = *Homo sapiens* GN = STT3B PE = 1 SV = 1 | 94 kDa | 0 | 2 | 0 | 0 |
| Doublecortin domain-containing protein 2 OS = *Homo sapiens* OX = 9606 GN = DCDC2 PE = 1 SV = 2 | 53 kDa | 0 | 17 | 0 | 2 |
| Double-stranded RNA-binding protein Staufen homolog 1 OS = *Homo sapiens* OX = 9606 GN = STAU1 PE = 1 SV = 2 | 63 kDa | 0 | 15 | 4 | 4 |
| Dynactin subunit 2 OS = *Homo sapiens* GN = DCTN2 PE = 1 SV = 4 | 44 kDa | 0 | 6 | 0 | 2 |
| Dynein heavy chain 10, axonemal OS = *Homo sapiens* OX = 9606 GN = DNAH10 PE = 1 SV = 4 | 515 kDa | 0 | 1 | 0 | 2 |
| EBNA1 binding protein 2, isoform CRA_d OS = *Homo sapiens* GN = EBNA1BP2 PE = 1 SV = 1 | 41 kDa | 0 | 5 | 0 | 0 |
| Ectonucleotide pyrophosphatase/phosphodiesterase family member 1 OS = *Homo sapiens* OX = 9606 GN = ENPP1 PE = 1 SV = 2 | 105 kDa | 0 | 0 | 0 | 2 |
| EH domain-containing protein 4 OS = *Homo sapiens* OX = 9606 GN = EHD4 PE = 1 SV = 1 | 61 kDa | 0 | 5 | 0 | 3 |
| Elongation factor Tu, mitochondrial OS = *Homo sapiens* GN = TUFM PE = 1 SV = 2 | 50 kDa | 0 | 9 | 0 | 0 |
| Emerin OS = *Homo sapiens* GN = EMD PE = 1 SV = 1 | 29 kDa | 0 | 6 | 0 | 0 |
| Epoxide hydrolase 1 OS = *Homo sapiens* OX = 9606 GN = EPHX1 PE = 1 SV = 1 | 53 kDa | 0 | 0 | 0 | 3 |
| ER lumen protein-retaining receptor 3 OS = *Homo sapiens* GN = KDELR3 PE = 2 SV = 1 | 25 kDa | 0 | 5 | 0 | 0 |
| Eukaryotic translation initiation factor 3 subunit E OS = *Homo sapiens* GN = EIF3E PE = 1 SV = 1 | 52 kDa | 0 | 8 | 0 | 0 |
| Eukaryotic translation initiation factor 3 subunit F OS = *Homo sapiens* GN = EIF3F PE = 1 SV = 1 | 38 kDa | 0 | 14 | 0 | 0 |
| Eukaryotic translation initiation factor 3 subunit H OS = *Homo sapiens* GN = EIF3H PE = 1 SV = 1 | 40 kDa | 0 | 5 | 0 | 0 |
| FACT complex subunit SPT16 OS = *Homo sapiens* GN = SUPT16H PE = 1 SV = 1 | 120 kDa | 0 | 7 | 0 | 0 |
| Far upstream element-binding protein 1 OS = *Homo sapiens* OX = 9606 GN = FUBP1 PE = 1 SV = 3 | 68 kDa | 0 | 3 | 0 | 1 |
| Fascin OS = *Homo sapiens* GN = FSCN1 PE = 1 SV = 3 | 55 kDa | 0 | 12 | 0 | 0 |
| Fibrous sheath-interacting protein 2 OS = *Homo sapiens* OX = 9606 GN = FSIP2 PE = 2 SV = 4 | 781 kDa | 0 | 0 | 2 | 1 |
| Filaggrin OS = *Homo sapiens* GN = FLG PE = 1 SV = 3 | 435 kDa | 0 | 3 | 0 | 0 |
| Filaggrin-2 OS = *Homo sapiens* GN = FLG2 PE = 1 SV = 1 | 248 kDa | 0 | 2 | 0 | 0 |
| Flotillin-2 OS = *Homo sapiens* GN = FLOT2 PE = 1 SV = 1 | 53 kDa | 0 | 13 | 0 | 0 |
| Galectin-3 OS = *Homo sapiens* GN = LGALS3 PE = 1 SV = 5 | 26 kDa | 0 | 39 | 0 | 0 |
| Galectin-3-binding protein OS = *Homo sapiens* OX = 9606 GN = LGALS3BP PE = 1 SV = 1 | 65 kDa | 0 | 4 | 0 | 3 |
| Galectin-8 OS = *Homo sapiens* OX = 9606 GN = LGALS8 PE = 1 SV = 4 | 36 kDa | 0 | 5 | 2 | 0 |
| Glutamate dehydrogenase 1, mitochondrial OS = *Homo sapiens* OX = 9606 GN = GLUD1 PE = 1 SV = 2 | 61 kDa | 0 | 4 | 0 | 0 |
| Glutathione peroxidase 1 OS = *Homo sapiens* GN = GPX1 PE = 1 SV = 4 | 22 kDa | 0 | 3 | 0 | 2 |
| Glycylpeptide N-tetradecanoyltransferase 2 OS = *Homo sapiens* GN = NMT2 PE = 1 SV = 1 | 57 kDa | 0 | 2 | 0 | 0 |
| Glypican-6 OS = *Homo sapiens* GN = GPC6 PE = 1 SV = 1 | 63 kDa | 0 | 14 | 0 | 0 |
| Golgi-associated plant pathogenesis-related protein 1 OS = *Homo sapiens* GN = GLIPR2 PE = 1 SV = 3 | 17 kDa | 0 | 20 | 0 | 0 |
| Gremlin-1 OS = *Homo sapiens* OX = 9606 GN = GREM1 PE = 1 SV = 1 | 21 kDa | 0 | 0 | 3 | 0 |
| Guanine nucleotide-binding protein G(I)/G(S)/G(O) subunit gamma-12 OS = *Homo sapiens* GN = GNG12 PE = 1 SV = 3 | 8 kDa | 0 | 6 | 0 | 0 |
| Guanine nucleotide-binding protein G(k) subunit alpha OS = *Homo sapiens* GN = GNAI3 PE = 1 SV = 3 | 41 kDa | 0 | 17 | 0 | 0 |
| Hamartin OS = *Homo sapiens* GN = TSC1 PE = 1 SV = 2 | 130 kDa | 0 | 0 | 0 | 2 |
| Heat shock-related 70 kDa protein 2 OS = *Homo sapiens* OX = 9606 GN = HSPA2 PE = 1 SV = 1 | 70 kDa | 0 | 0 | 0 | 24 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Hemicentin-2 OS = *Homo sapiens* OX = 9606 GN = HMCN2 PE = 2 SV = 3 | 542 kDa | 0 | 0 | 0 | 0 |
| Heparan sulfate glucosamine 3-O-sulfotransferase 6 OS = *Homo sapiens* GN = HS3ST6 PE = 1 SV = 2 | 37 kDa | 0 | 3 | 0 | 0 |
| Heterogeneous nuclear ribonucleoprotein A0 OS = *Homo sapiens* GN = HNRNPA0 PE = 1 SV = 1 | 31 kDa | 0 | 15 | 0 | 0 |
| Heterogeneous nuclear ribonucleoprotein H2 OS = *Homo sapiens* GN = HNRNPH2 PE = 1 SV = 1 | 49 kDa | 0 | 14 | 0 | 0 |
| Homeobox protein Hox-B3 OS = *Homo sapiens* OX = 9606 GN = HOXB3 PE = 2 SV = 2 | 44 kDa | 0 | 5 | 0 | 0 |
| Hornerin OS = *Homo sapiens* GN = HRNR PE = 1 SV = 2 | 282 kDa | 0 | 15 | 0 | 0 |
| Hsc70-interacting protein (Fragment) OS = *Homo sapiens* GN = ST13 PE = 1 SV = 1 | 16 kDa | 0 | 2 | 0 | 0 |
| Hyaluronan and proteoglycan link protein 1 OS = *Homo sapiens* OX = 9606 GN = HAPLN1 PE = 2 SV = 2 | 40 kDa | 0 | 0 | 0 | 0 |
| Hyaluronan and proteoglycan link protein 3 OS = *Homo sapiens* GN = HAPLN3 PE = 2 SV = 1 | 41 kDa | 0 | 6 | 0 | 0 |
| Intercellular adhesion molecule 1 OS = *Homo sapiens* GN = ICAM1 PE = 1 SV = 2 | 58 kDa | 0 | 16 | 0 | 0 |
| Interleukin enhancer-binding factor 2 OS = *Homo sapiens* GN = ILF2 PE = 1 SV = 1 | 39 kDa | 0 | 29 | 0 | 0 |
| Isocitrate dehydrogenase [NADP] cytoplasmic OS = *Homo sapiens* GN = IDH1 PE = 1 SV = 2 | 47 kDa | 0 | 7 | 0 | 0 |
| Isoform 1 of Gamma-adducin OS = *Homo sapiens* OX = 9606 GN = ADD3 | 76 kDa | 0 | 7 | 0 | 1 |
| Isoform 1 of Polypyrimidine tract-binding protein 3 OS = *Homo sapiens* OX = 9606 GN = PTBP3 | 57 kDa | 0 | 5 | 0 | 3 |
| Isoform 1 of Synaptic functional regulator FMR1 OS = *Homo sapiens* OX = 9606 GN = FMR1 | 67 kDa | 0 | 5 | 0 | 1 |
| Isoform 2 of 2,4-dienoyl-CoA reductase, mitochondrial OS = *Homo sapiens* OX = 9606 GN = DECR1 | 35 kDa | 0 | 8 | 0 | 1 |
| Isoform 2 of A-kinase anchor protein 13 OS = *Homo sapiens* OX = 9606 GN = AKAP13 | 308 kDa | 0 | 2 | 0 | 0 |
| Isoform 2 of Ankyrin repeat domain-containing protein 17 OS = *Homo sapiens* OX = 9606 GN = ANKRD17 | 274 kDa | 0 | 0 | 0 | 0 |
| Isoform 2 of AP-2 complex subunit mu OS = *Homo sapiens* OX = 9606 GN = AP2M1 | 49 kDa | 0 | 9 | 0 | 1 |
| Isoform 2 of Bcl-2-associated transcription factor 1 OS = *Homo sapiens* OX = 9606 GN = BCLAF1 | 106 kDa | 0 | 4 | 0 | 0 |
| Isoform 2 of Cadherin-2 OS = *Homo sapiens* OX = 9606 GN = CDH2 | 97 kDa | 0 | 7 | 0 | 2 |
| Isoform 2 of Calponin-1 OS = *Homo sapiens* OX = 9606 GN = CNN1 | 31 kDa | 0 | 1 | 5 | 8 |
| Isoform 2 of Chromodomain Y-like protein OS = *Homo sapiens* GN = CDYL | 61 kDa | 0 | 4 | 0 | 0 |
| Isoform 2 of Collagen alpha-1(VII) chain OS = *Homo sapiens* OX = 9606 GN = COE7A1 | 292 kDa | 0 | 70 | 2 | 1 |
| Isoform 2 of Cyclin-Y OS = *Homo sapiens* GN = CCNY | 37 kDa | 0 | 3 | 0 | 0 |
| Isoform 2 of Cysteine-rich protein 2 OS = *Homo sapiens* OX = 9606 GN = CRIP2 | 30 kDa | 0 | 5 | 0 | 0 |
| Isoform 2 of DnaJ homolog subfamily C member 10 OS = *Homo sapiens* GN = DNAJC10 | 86 kDa | 0 | 4 | 0 | 0 |
| Isoform 2 of Fibroblast growth factor 2 OS = *Homo sapiens* OX = 9606 GN = FGF2 | 23 kDa | 0 | 13 | 3 | 1 |
| Isoform 2 of Fibulin-2 OS = *Homo sapiens* OX = 9606 GN = FBLN2 | 132 kDa | 0 | 6 | 0 | 0 |
| Isoform 2 of GDNF family receptor alpha-1 OS = *Homo sapiens* GN = GFRA1 | 51 kDa | 0 | 8 | 0 | 0 |
| Isoform 2 of Glycogen phosphorylase, liver form OS = *Homo sapiens* OX = 9606 GN = PYGL | 93 kDa | 0 | 2 | 0 | 1 |
| Isoform 2 of Golgin subfamily A member 5 OS = *Homo sapiens* OX = 9606 GN = GOLGA5 | 78 kDa | 0 | 0 | 0 | 0 |
| Isoform 2 of H/ACA ribonucleoprotein complex subunit 1 OS = *Homo sapiens* OX = 9606 GN = GAR1 | 21 kDa | 0 | 1 | 1 | 2 |
| Isoform 2 of Helicase SRCAP OS = *Homo sapiens* OX = 9606 GN = SRCAP | 337 kDa | 0 | 2 | 0 | 0 |
| Isoform 2 of Histone-binding protein RBBP4 OS = *Homo sapiens* OX = 9606 GN = RBBP4 | 48 kDa | 0 | 6 | 0 | 0 |
| Isoform 2 of Histone-lysine N-methyltransferase, H3 lysine-36 and H4 lysine-20 specific OS = *Homo sapiens* OX = 9606 GN = NSD1 | 267 kDa | 0 | 6 | 0 | 1 |
| Isoform 2 of Insulin-like growth factor-binding protein 7 OS = *Homo sapiens* OX = 9606 GN = IGFBP7 | 29 kDa | 0 | 54 | 13 | 7 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 2 of Interferon-inducible double-stranded RNA-dependent protein kinase activator A OS = *Homo sapiens* OX = 9606 GN = PRKRA | 33 kDa | 0 | 4 | 1 | 1 |
| Isoform 2 of KH domain-containing, RNA-binding, signal transduction-associated protein 3 OS = *Homo sapiens* GN = KHDRBS3 | 30 kDa | 0 | 8 | 0 | 0 |
| Isoform 2 of Lactadherin OS = *Homo sapiens* GN = MFGE8 | 35 kDa | 0 | 25 | 2 | 1 |
| Isoform 2 of L-amino-acid oxidase OS = *Homo sapiens* OX = 9606 GN = IL4I1 | 65 kDa | 0 | 2 | 0 | 1 |
| Isoform 2 of Macrophage-capping protein OS = *Homo sapiens* GN = CAPG | 37 kDa | 0 | 3 | 0 | 0 |
| Isoform 2 of Matrilin-2 OS = *Homo sapiens* OX = 9606 GN = MATN2 | 105 kDa | 0 | 37 | 8 | 5 |
| Isoform 2 of Mesoderm-specific transcript homolog protein OS = *Homo sapiens* OX = 9606 GN = MEST | 38 kDa | 0 | 0 | 0 | 4 |
| Isoform 2 of Microtubule-associated protein 1A OS = *Homo sapiens* OX = 9606 GN = MAP1A | 306 kDa | 0 | 4 | 2 | 3 |
| Isoform 2 of Midkine OS = *Homo sapiens* OX = 9606 GN = MDK | 10 kDa | 0 | 4 | 2 | 2 |
| Isoform 2 of Monoacylglycerol lipase ABHD12 OS = *Homo sapiens* GN = ABHD12 | 46 kDa | 0 | 2 | 0 | 0 |
| Isoform 2 of Multidrug resistance protein 1 OS = *Homo sapiens* OX = 9606 GN = ABCB1 | 134 kDa | 0 | 1 | 0 | 2 |
| Isoform 2 of Myosin-11 OS = *Homo sapiens* GN = MYH11 | 228 kDa | 0 | 161 | 37 | 0 |
| Isoform 2 of Myosin-14 OS = *Homo sapiens* OX = 9606 GN = MYH14 | 232 kDa | 0 | 141 | 26 | 26 |
| Isoform 2 of NADH dehydrogenase [ubiquinone] 1 beta subcomplex subunit 4 OS = *Homo sapiens* OX = 9606 GN = NDUFB4 | 14 kDa | 0 | 1 | 0 | 2 |
| Isoform 2 of Nuclear receptor corepressor 1 OS = *Homo sapiens* OX = 9606 GN = NCOR1 | 259 kDa | 0 | 0 | 2 | 0 |
| Isoform 2 of Periostin OS = *Homo sapiens* OX = 9606 GN = POSTN | 87 kDa | 0 | 0 | 5 | 5 |
| Isoform 2 of Pescadillo homolog OS = *Homo sapiens* OX = 9606 GN = PES1 | 67 kDa | 0 | 5 | 1 | 0 |
| Isoform 2 of Platelet-derived growth factor subunit B OS = *Homo sapiens* OX = 9606 GN = PDGFB | 26 kDa | 0 | 1 | 3 | 1 |
| Isoform 2 of Protein ELYS OS = *Homo sapiens* OX = 9606 GN = AHCTF1 | 256 kDa | 0 | 0 | 2 | 0 |
| Isoform 2 of Ran-binding protein 3 OS = *Homo sapiens* OX = 9606 GN = RANBP3 | 60 kDa | 0 | 5 | 0 | 0 |
| Isoform 2 of Regulator of chromosome condensation OS = *Homo sapiens* OX = 9606 GN = RCC1 | 48 kDa | 0 | 16 | 0 | 0 |
| Isoform 2 of Retinol-binding protein 1 OS = *Homo sapiens* OX = 9606 GN = RBP1 | 17 kDa | 0 | 0 | 0 | 2 |
| Isoform 2 of RNA-binding protein 39 OS = *Homo sapiens* GN = RBM39 | 59 kDa | 0 | 0 | 0 | 2 |
| Isoform 2 of RNA-binding protein 8A OS = *Homo sapiens* OX = 9606 GN = RBM8A | 20 kDa | 0 | 5 | 0 | 1 |
| Isoform 2 of Ryanodine receptor 1 OS = *Homo sapiens* OX = 9606 GN = RYR1 | 565 kDa | 0 | 1 | 0 | 2 |
| Isoform 2 of SCO-spondin OS = *Homo sapiens* OX = 9606 GN = SSPO | 139 kDa | 0 | 3 | 0 | 0 |
| Isoform 2 of Semaphorin-7A OS = *Homo sapiens* OX = 9606 GN = SEMA7A | 73 kDa | 0 | 3 | 1 | 3 |
| Isoform 2 of Septin-8 OS = *Homo sapiens* OX = 9606 GN = SEPT8 | 50 kDa | 0 | 12 | 0 | 3 |
| Isoform 2 of Serine/threonine-protein phosphatase PGAM5, mitochondrial OS = *Homo sapiens* OX = 9606 GN = PGAM5 | 28 kDa | 0 | 5 | 0 | 1 |
| Isoform 2 of SH3 domain-containing kinase-binding protein 1 OS = *Homo sapiens* OX = 9606 GN = SH3KBP1 | 69 kDa | 0 | 2 | 0 | 2 |
| Isoform 2 of Signal recognition particle receptor subunit alpha OS = *Homo sapiens* OX = 9606 GN = SRPRA | 67 kDa | 0 | 3 | 0 | 1 |
| Isoform 2 of Signal-induced proliferation-associated 1-like protein 1 OS = *Homo sapiens* OX = 9606 GN = SIPA1L1 | 197 kDa | 0 | 0 | 0 | 0 |
| Isoform 2 of Sorting nexin-27 OS = *Homo sapiens* GN = SNX27 | 60 kDa | 0 | 4 | 0 | 0 |
| Isoform 2 of Spectrin beta chain, erythrocytic OS = *Homo sapiens* OX = 9606 GN = SPTB | 268 kDa | 0 | 8 | 0 | 2 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform 2 of Testis-expressed protein 10 OS = *Homo sapiens* OX = 9606 GN = TEX10 | 104 kDa | 0 | 2 | 0 | 0 |
| Isoform 2 of Tissue factor pathway inhibitor 2 OS = *Homo sapiens* OX = 9606 GN = TFPI2 | 26 kDa | 0 | 9 | 6 | 0 |
| Isoform 2 of Tyrosine-protein kinase BAZ1B OS = *Homo sapiens* OX = 9606 GN = BAZ1B | 170 kDa | 0 | 4 | 0 | 0 |
| Isoform 2 of UDP-glucuronosyltransferase 1-6 OS = *Homo sapiens* OX = 9606 GN = UGT1A6 | 30 kDa | 0 | 4 | 0 | 0 |
| Isoform 2 of Vesicle-associated membrane protein-associated protein A OS = *Homo sapiens* OX = 9606 GN = VAPA | 33 kDa | 0 | 3 | 0 | 1 |
| Isoform 2 of Voltage-dependent calcium channel subunit alpha-2/delta-1 OS = *Homo sapiens* OX = 9606 GN = CACNA2D1 | 123 kDa | 0 | 2 | 1 | 0 |
| Isoform 2 of Y-box-binding protein 3 OS = *Homo sapiens* OX = 9606 GN = YBX3 | 32 kDa | 0 | 15 | 0 | 1 |
| Isoform 2 of Zinc finger homeobox protein 4 OS = *Homo sapiens* OX = 9606 GN = ZFHX4 | 397 kDa | 0 | 2 | 0 | 0 |
| Isoform 3 of 1-phosphatidylinositol 4,5-bisphosphate phosphodiesterase beta-4 OS = *Homo sapiens* OX = 9606 GN = PLCB4 | 136 kDa | 0 | 3 | 0 | 0 |
| Isoform 3 of Alpha-adducin OS = *Homo sapiens* GN = ADD1 | 84 kDa | 0 | 2 | 0 | 0 |
| Isoform 3 of Cytoskeleton-associated protein 5 OS = *Homo sapiens* OX = 9606 GN = CKAP5 | 226 kDa | 0 | 3 | 0 | 0 |
| Isoform 3 of DnaJ homolog subfamily C member 11 OS = *Homo sapiens* GN = DNAJC11 | 57 kDa | 0 | 2 | 0 | 1 |
| Isoform 3 of E3 ubiquitin-protein ligase CHFR OS = *Homo sapiens* OX = 9606 GN = CHFR | 69 kDa | 0 | 0 | 0 | 0 |
| Isoform 3 of H/ACA ribonucleoprotein complex subunit DKC1 OS = *Homo sapiens* OX = 9606 GN = DKC1 | 48 kDa | 0 | 13 | 1 | 1 |
| Isoform 3 of Histone-lysine N-methyltransferase 2D OS = *Homo sapiens* OX = 9606 GN = KMT2D | 594 kDa | 0 | 1 | 0 | 1 |
| Isoform 3 of Latent-transforming growth factor beta-binding protein 4 OS = *Homo sapiens* OX = 9606 GN = LTBP4 | 169 kDa | 0 | 34 | 0 | 0 |
| Isoform 3 of Malate dehydrogenase, cytoplasmic OS = *Homo sapiens* OX = 9606 GN = MDH1 | 39 kDa | 0 | 3 | 0 | 0 |
| Isoform 3 of Putative oxidoreductase GLYR1 OS = *Homo sapiens* OX = 9606 GN = GLYR1 | 60 kDa | 0 | 4 | 0 | 0 |
| Isoform 3 of Scaffold attachment factor B1 OS = *Homo sapiens* GN = SAFB | 103 kDa | 0 | 3 | 0 | 0 |
| Isoform 3 of Torsin-1A-interacting protein 1 OS = *Homo sapiens* GN = TOR1AIP1 | 66 kDa | 0 | 5 | 0 | 0 |
| Isoform 4 of CD109 antigen OS = *Homo sapiens* GN = CD109 | 160 kDa | 0 | 18 | 0 | 0 |
| Isoform 4 of FYVE and coiled-coil domain-containing protein 1 OS = *Homo sapiens* OX = 9606 GN = FYCO1 | 169 kDa | 0 | 0 | 0 | 0 |
| Isoform 4 of IQ domain-containing protein N OS = *Homo sapiens* OX = 9606 GN = IQCN | 147 kDa | 0 | 0 | 0 | 3 |
| Isoform 4 of Kinesin-like protein KIF24 OS = *Homo sapiens* OX = 9606 GN = KIF24 | 129 kDa | 0 | 2 | 0 | 0 |
| Isoform 4 of Latent-transforming growth factor beta-binding protein 1 OS = *Homo sapiens* OX = 9606 GN = LTBP1 | 187 kDa | 0 | 1 | 4 | 1 |
| Isoform 4 of Protein diaphanous homolog 3 OS = *Homo sapiens* GN = DIAPH3 | 136 kDa | 0 | 2 | 0 | 0 |
| Isoform 5 of E1A-binding protein p400 OS = *Homo sapiens* OX = 9606 GN = EP400 | 340 kDa | 0 | 1 | 0 | 0 |
| Isoform 5 of Immunoglobulin-like and fibronectin type III domain-containing protein 1 OS = *Homo sapiens* OX = 9606 GN = IGFN1 | 384 kDa | 0 | 3 | 0 | 2 |
| Isoform 5 of LIM domain only protein 7 OS = *Homo sapiens* GN = LMO7 | 158 kDa | 0 | 8 | 0 | 0 |
| Isoform 5 of Papilin OS = *Homo sapiens* OX = 9606 GN = PAPLN | 136 kDa | 0 | 17 | 1 | 1 |
| Isoform 6 of Treacle protein OS = *Homo sapiens* OX = 9606 GN = TCOF1 | 148 kDa | 0 | 2 | 0 | 0 |
| Isoform B of Collagen alpha-1(XI) chain OS = *Homo sapiens* OX = 9606 GN = COL11Al | 182 kDa | 0 | 0 | 1 | 2 |
| Isoform B of Collagen alpha-6(IV) chain OS = *Homo sapiens* OX = 9606 GN = COL4A6 | 164 kDa | 0 | 5 | 2 | 0 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Isoform B of DnaJ homolog subfamily B member 6 OS = *Homo sapiens* OX = 9606 GN = DNAJB6 | 27 kDa | 0 | 0 | 1 | 2 |
| Isoform B of Methyl-CpG-binding protein 2 OS = *Homo sapiens* OX = 9606 GN = MECP2 | 53 kDa | 0 | 11 | 1 | 0 |
| Isoform B of Ras-related C3 botulinum toxin substrate 1 OS = *Homo sapiens* OX = 9606 GN = RAC1 | 23 kDa | 0 | 3 | 0 | 0 |
| Isoform B of Transforming growth factor beta-2 proprotein OS = *Homo sapiens* OX = 9606 GN = TGFB2 | 51 kDa | 0 | 5 | 1 | 2 |
| Isoform Beta-3B of Integrin beta-3 OS = *Homo sapiens* OX = 9606 GN = ITGB3 | 86 kDa | 0 | 4 | 0 | 2 |
| Isoform C of Fibulin-1 OS = *Homo sapiens* OX = 9606 GN = FBLN1 | 74 kDa | 0 | 13 | 0 | 8 |
| Isoform Long of Proteasome subunit alpha type-1 OS = *Homo sapiens* OX = 9606 GN = PSMA1 | 30 kDa | 0 | 2 | 0 | 2 |
| Isoform Non-brain of Clathrin light chain A OS = *Homo sapiens* OX = 9606 GN = CLTA | 24 kDa | 0 | 17 | 0 | 2 |
| Isoform Short of Laminin subunit gamma-2 OS = *Homo sapiens* OX = 9606 GN = LAMC2 | 122 kDa | 0 | 5 | 0 | 1 |
| Keratin, type I cytoskeletal 14 OS = *Homo sapiens* OX = 9606 GN = KRT14 PE = 1 SV = 4 | 52 kDa | 0 | 94 | 0 | 18 |
| Keratin, type I cytoskeletal 16 OS = *Homo sapiens* GN = KRT16 PE = 1 SV = 4 | 51 kDa | 0 | 99 | 0 | 0 |
| Keratin, type I cytoskeletal 19 OS = *Homo sapiens* GN = KRT19 PE = 1 SV = 4 | 44 kDa | 0 | 753 | 0 | 0 |
| Keratin, type II cuticular Hb5 OS = *Homo sapiens* GN = KRT85 PE = 1 SV = 1 | 56 kDa | 0 | 3 | 0 | 0 |
| Keratin, type II cytoskeletal 1 OS = *Homo sapiens* GN = KRT1 PE = 1 SV = 6 | 66 kDa | 0 | 497 | 0 | 0 |
| Keratin, type II cytoskeletal 5 OS = *Homo sapiens* GN = KRT5 PE = 1 SV = 3 | 62 kDa | 0 | 93 | 0 | 0 |
| Keratin, type II cytoskeletal 6B OS = *Homo sapiens* OX = 9606 GN = KRT6B PE = 1 SV = 5 | 60 kDa | 0 | 104 | 18 | 0 |
| Keratin, type II cytoskeletal 7 OS = *Homo sapiens* OX = 9606 GN = KRT7 PE = 1 SV = 5 | 51 kDa | 0 | 0 | 0 | 135 |
| Kinesin-like protein KIFC2 OS = *Homo sapiens* OX = 9606 GN = KIFC2 PE = 2 SV = 1 | 90 kDa | 0 | 2 | 0 | 1 |
| Ladinin-1 OS = *Homo sapiens* OX = 9606 GN = LAD1 PE = 1 SV = 2 | 57 kDa | 0 | 0 | 0 | 6 |
| Laminin subunit beta-3 OS = *Homo sapiens* GN = LAMB3 PE = 1 SV = 1 | 130 kDa | 0 | 10 | 0 | 0 |
| Latent-transforming growth factor beta-binding protein 2 OS = *Homo sapiens* GN = LTBP2 PE = 1 SV = 1 | 190 kDa | 0 | 23 | 0 | 0 |
| Leucine zipper protein 1 OS = *Homo sapiens* OX = 9606 GN = LUZP1 PE = 1 SV = 2 | 120 kDa | 0 | 5 | 0 | 0 |
| Lipoamide acyltransferase component of branched-chain alpha-keto acid dehydrogenase complex, mitochondrial OS = *Homo sapiens* OX = 9606 GN = DBT PE = 1 SV = 3 | 53 kDa | 0 | 6 | 4 | 8 |
| Low-density lipoprotein receptor-related protein 1B OS = *Homo sapiens* GN = LRP1B PE = 1 SV = 2 | 515 kDa | 0 | 2 | 0 | 0 |
| Low-density lipoprotein receptor-related protein 2 OS = *Homo sapiens* OX = 9606 GN = LRP2 PE = 1 SV = 3 | 522 kDa | 0 | 0 | 0 | 2 |
| Lysyl oxidase homolog 1 OS = *Homo sapiens* OX = 9606 GN = LOXL1 PE = 1 SV = 2 | 63 kDa | 0 | 24 | 1 | 0 |
| Magnesium transporter protein 1 OS = *Homo sapiens* GN = MAGT1 PE = 1 SV = 1 | 42 kDa | 0 | 4 | 1 | 1 |
| MARCKS-related protein OS = *Homo sapiens* GN = MARCKSL1 PE = 1 SV = 2 | 20 kDa | 0 | 4 | 0 | 0 |
| Metastasis-associated protein MTA2 OS = *Homo sapiens* GN = MTA2 PE = 1 SV = 1 | 75 kDa | 0 | 5 | 0 | 0 |
| Microsomal glutathione S-transferase 1 OS = *Homo sapiens* OX = 9606 GN = MGST1 PE = 1 SV = 1 | 18 kDa | 0 | 0 | 0 | 3 |
| Mitochondrial GTPase 1 OS = *Homo sapiens* OX = 9606 PE = 3 SV = 1 | 37 kDa | 0 | 0 | 0 | 2 |
| MKI67 FHA domain-interacting nucleolar phosphoprotein (Fragment) OS = *Homo sapiens* GN = NIFK PE = 1 SV = 1 | 20 kDa | 0 | 6 | 0 | 0 |
| Mucin-16 OS = *Homo sapiens* OX = 9606 GN = MUC16 PE = 1 SV = 3 | 1519 kDa | 0 | 0 | 2 | 4 |
| Myelin expression factor 2 OS = *Homo sapiens* OX = 9606 GN = MYEF2 PE = 1 SV = 3 | 64 kDa | 0 | 2 | 0 | 0 |
| Myosin light chain 6B OS = *Homo sapiens* OX = 9606 GN = MYL6B PE = 1 SV = 1 | 23 kDa | 0 | 0 | 6 | 0 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Myristoylated alanine-rich C-kinase substrate OS = *Homo sapiens* GN = MARCKS PE = 1 SV = 4 | 32 kDa | 0 | 11 | 0 | 0 |
| N-acylneuraminate cytidylyltransferase OS = *Homo sapiens* GN = CMAS PE = 1 SV = 2 | 48 kDa | 0 | 6 | 0 | 0 |
| NAD(P) transhydrogenase, mitochondrial OS = *Homo sapiens* GN = NNT PE = 1 SV = 1 | 100 kDa | 0 | 3 | 0 | 0 |
| Nestin OS = *Homo sapiens* GN = NES PE = 1 SV = 2 | 177 kDa | 0 | 18 | 0 | 0 |
| Neurabin-2 OS = *Homo sapiens* GN = PPP1R9BPE = 1 SV = 1 | 89 kDa | 0 | 3 | 0 | 0 |
| Neurobeachin OS = *Homo sapiens* OX = 9606GN = NBEA PE = 1 SV = 3 | 328 kDa | 0 | 0 | 0 | 3 |
| Nicotinate-nucleotide pyrophosphorylase [carboxylating] OS = *Homo sapiens* OX = 9606 GN = QPRT PE = 1 SV = 3 | 31 kDa | 0 | 0 | 0 | 4 |
| Non-syndromic hearing impairment protein 5 OS = *Homo sapiens* GN = DFNA5 PE = 1 SV = 2 | 55 kDa | 0 | 2 | 0 | 0 |
| Nuclear receptor-binding protein OS = *Homo sapiens* GN = NRBP1 PE = 1 SV = 1 | 61 kDa | 0 | 5 | 0 | 0 |
| Nucleolar complex protein 3 homolog OS = *Homo sapiens* GN = NOC3L PE = 1 SV = 1 | 93 kDa | 0 | 5 | 0 | 0 |
| Nucleolar complex protein 4 homolog OS = *Homo sapiens* GN = NOC4L PE = 1 SV = 1 | 58 kDa | 0 | 5 | 0 | 0 |
| Nucleolar protein 58 OS = *Homo sapiens* GN = NOP58 PE = 1 SV = 1 | 60 kDa | 0 | 6 | 0 | 0 |
| Nucleolar transcription factor 1 OS = *Homo sapiens* GN = UBTF PE = 1 SV = 1 | 87 kDa | 0 | 2 | 0 | 0 |
| Nucleoplasmin-3 OS = *Homo sapiens* GN = NPM3 PE = 1 SV = 3 | 19 kDa | 0 | 3 | 0 | 0 |
| Palladin OS = *Homo sapiens* OX = 9606 GN = PALLD PE = 1 SV = 3 | 151 kDa | 0 | 7 | 0 | 6 |
| PDZ and LIM domain protein 1 OS = *Homo sapiens* OX = 9606 GN = PDLIM1 PE = 1 SV = 4 | 36 kDa | 0 | 0 | 0 | 4 |
| PDZ and LIM domain protein 4 OS = *Homo sapiens* GN = PDLIM4 PE = 1 SV = 2 | 35 kDa | 0 | 3 | 0 | 0 |
| Pentraxin-related protein PTX3 OS = *Homo sapiens* GN = PTX3 PE = 1 SV = 3 | 42 kDa | 0 | 23 | 0 | 0 |
| Peptidyl-prolyl cis-trans isomerase B OS = *Homo sapiens* GN = PPIB PE = 1 SV = 2 | 24 kDa | 0 | 52 | 0 | 0 |
| Peptidyl-prolyl cis-trans isomerase FKBP10 OS = *Homo sapiens* GN = FKBP10 PE = 1 SV = 1 | 64 kDa | 0 | 3 | 0 | 0 |
| Peptidyl-prolyl cis-trans isomerase FKBP3 OS = *Homo sapiens* GN = FKBP3 PE = 1 SV = 1 | 25 kDa | 0 | 8 | 0 | 0 |
| Periaxin OS = *Homo sapiens* OX = 9606 GN = PRX PE = 1 SV = 2 | 155 kDa | 0 | 0 | 0 | 2 |
| Periodic tryptophan protein 1 homolog OS = *Homo sapiens* OX = 9606 GN = PWP1 PE = 1 SV = 1 | 56 kDa | 0 | 2 | 0 | 0 |
| Peroxiredoxin-1 (Fragment) OS = *Homo sapiens* GN = PRDX1 PE = 1 SV = 1 | 19 kDa | 0 | 13 | 0 | 0 |
| Phosphoglycerate mutase 1 OS = *Homo sapiens* GN = PGAM1 PE = 1 SV = 2 | 29 kDa | 0 | 11 | 0 | 0 |
| Pinin OS = *Homo sapiens* OX = 9606 GN = PNN PE = 1 SV = 5 | 82 kDa | 0 | 6 | 2 | 4 |
| Platelet-activating factor acetylhydrolase IB subunit alpha OS = *Homo sapiens* OX = 9606 GN = PAFAH1B1 PE = 1 SV = 2 | 47 kDa | 0 | 4 | 0 | 0 |
| Poly [ADP-ribose] polymerase 1 OS = *Homo sapiens* GN = PARP1 PE = 1 SV = 4 | 113 kDa | 0 | 30 | 0 | 0 |
| Poly(U)-binding-splicing factor PUF60 (Fragment) OS = *Homo sapiens* GN = PUF60 PE = 1 SV = 1 | 57 kDa | 0 | 3 | 0 | 0 |
| Polymerase delta-interacting protein 3 OS = *Homo sapiens* GN = POLDIP3 PE = 1 SV = 1 | 48 kDa | 0 | 6 | 0 | 0 |
| Polymerase I and transcript release factor OS = *Homo sapiens* GN = PTRF PE = 1 SV = 1 | 43 kDa | 0 | 89 | 0 | 0 |
| Polyubiquitin-B OS = *Homo sapiens* GN = UBBPE = 1 SV = 1 | 17 kDa | 0 | 111 | 0 | 0 |
| POU domain, class 3, transcription factor 3 OS = *Homo sapiens* GN = POU3F3 PE = 2 SV = 2 | 50 kDa | 0 | 20 | 0 | 0 |
| PR domain zinc finger protein 8 OS = *Homo sapiens* GN = PRDM8 PE = 1 SV = 3 | 72 kDa | 0 | 2 | 0 | 0 |
| Prefoldin subunit 6 OS = *Homo sapiens* GN = PFDN6 PE = 1 SV = 1 | 15 kDa | 0 | 3 | 0 | 0 |
| Probable ATP-dependent RNA helicase DDX27 OS = *Homo sapiens* GN = DDX27 PE = 1 SV = 1 | 87 kDa | 0 | 4 | 0 | 0 |

TABLE 2-continued

Amniotic Fluid Cell-Derived ECM Components

| Protein | MW | Total Spectra Count Matrix A | Matrix B | Matrix C | Matrix D |
|---|---|---|---|---|---|
| Probable global transcription activator SNF2L1 OS = *Homo sapiens* OX = 9606 GN = SMARCA1 PE = 1 SV = 2 | 123 kDa | 0 | 6 | 0 | 0 |
| Probable maltase-glucoamylase 2 OS = *Homo sapiens* OX = 9606 GN = MGAM2 PE = 2 SV = 3 | 278 kDa | 0 | 0 | 0 | 2 |
| Procollagen galactosyltransferase 1 OS = *Homo sapiens* GN = COLGALT1 PE = 1 SV = 1 | 72 kDa | 0 | 3 | 0 | 0 |
| Procollagen-lysine,2-oxoglutarate 5-dioxygenase 3 OS = *Homo sapiens* GN = PLOD3 PE = 1 SV = 1 | 85 kDa | 0 | 3 | 0 | 0 |
| Prolow-density lipoprotein receptor-related protein 1 OS = *Homo sapiens* GN = LRP1 PE = 1 SV = 2 | 505 kDa | 0 | 2 | 0 | 0 |
| Protein disulfide-isomerase OS = *Homo sapiens* GN = P4HB PE = 1 SV = 2 | 53 kDa | 0 | 30 | 0 | 0 |
| Protein GREB1 OS = *Homo sapiens* GN = GREB1PE = 2 SV = 1 | 216 kDa | 0 | 0 | 0 | 2 |
| Protein kinase C delta-binding protein OS = *Homo sapiens* GN = PRKCDBP PE = 1 SV = 1 | 31 kDa | 0 | 20 | 0 | 0 |
| Protein MAK16 homolog OS = *Homo sapiens* GN = MAK16 PE = 1 SV = 2 | 35 kDa | 0 | 2 | 0 | 0 |
| Protein S100-A10 OS = *Homo sapiens* GN = S100A10 PE = 1 SV = 2 | 11 kDa | 0 | 11 | 0 | 0 |
| Protein S100-A13 OS = *Homo sapiens* GN = S100A13 PE = 1 SV = 1 | 11 kDa | 0 | 5 | 0 | 0 |
| Protein S100-A9 OS = *Homo sapiens* GN = S100A9 PE = 1 SV = 1 | 13 kDa | 0 | 12 | 0 | 0 |
| Protein-glutamine gamma-glutamyltransferase E OS = *Homo sapiens* GN = TGM3 PE = 1 SV = 4 | 77 kDa | 0 | 2 | 0 | 0 |
| Pumilio homolog 3 OS = *Homo sapiens* GN = PUM3 PE = 1 SV = 3 | 74 kDa | 0 | 6 | 0 | 0 |
| Raftlin OS = *Homo sapiens* GN = RFTN1 PE = 1 SV = 4 | 63 kDa | 0 | 3 | 0 | 0 |
| Ras GTPase-activating-like protein IQGAP1 OS = *Homo sapiens* GN = IQGAP1 PE = 1 SV = 1 | 189 kDa | 0 | 135 | 0 | 0 |
| Ras-related protein Rab-10 OS = *Homo sapiens* GN = RAB10 PE = 1 SV = 1 | 23 kDa | 0 | 13 | 0 | 0 |
| Ras-related protein Rab-14 (Fragment) OS = *Homo sapiens* GN = RAB14 PE = 1 SV = 1 | 20 kDa | 0 | 8 | 0 | 0 |
| Ras-related protein Rab-2A OS = *Homo sapiens* GN = RAB2A PE = 1 SV = 1 | 24 kDa | 0 | 5 | 0 | 1 |
| Ras-related protein Ral-A OS = *Homo sapiens* GN = RALA PE = 1 SV = 1 | 24 kDa | 0 | 2 | 0 | 0 |
| Regulation of nuclear pre-mRNA domain-containing protein 1B OS = *Homo sapiens* GN = RPRD1B PE = 1 SV = 1 | 37 kDa | 0 | 2 | 0 | 0 |
| Replication protein A 32 kDa subunit OS = *Homo sapiens* GN = RPA2 PE = 1 SV = 1 | 29 kDa | 0 | 3 | 0 | 1 |
| Replication protein A 70 kDa DNA-binding subunit OS = *Homo sapiens* GN = RPA1 PE = 1 SV = 2 | 68 kDa | 0 | 4 | 0 | 0 |
| Reticulocalbin-1 OS = *Homo sapiens* GN = RCN1 PE = 1 SV = 1 | 39 kDa | 0 | 7 | 0 | 0 |
| Retinoic acid-induced protein 3 OS = *Homo sapiens* OX = 9606 GN = GPRC5A PE = 1 SV = 2 | 40 kDa | 0 | 0 | 0 | 2 |
| Rho GTPase-activating protein 1 OS = *Homo sapiens* GN = ARHGAP1 PE = 1 SV = 1 | 50 kDa | 0 | 8 | 0 | 0 |
| Ribosomal protein L19 OS = *Homo sapiens* GN = RPL19 PE = 1 SV = 1 | 23 kDa | 0 | 21 | 0 | 0 |
| Ribosome biogenesis protein BRX1 homolog OS = *Homo sapiens* OX = 9606 GN = BRIX1 PE = 1 SV = 2 | 41 kDa | 0 | 5 | 0 | 3 |
| Ribosome biogenesis protein WDR12 OS = *Homo sapiens* GN = WDR12 PE = 1 SV = 2 | 48 kDa | 0 | 3 | 0 | 0 |
| Ribosome biogenesis regulatory protein homolog OS = *Homo sapiens* GN = RRS1 PE = 1 SV = 2 | 41 kDa | 0 | 11 | 0 | 0 |
| Ribosome production factor 2 homolog OS = *Homo sapiens* GN = RPF2 PE = 1 SV = 2 | 36 kDa | 0 | 3 | 0 | 0 |
| RNA-binding protein 28 OS = *Homo sapiens* OX = 9606 GN = RBM28 PE = 1 SV = 3 | 86 kDa | 0 | 2 | 0 | 2 |
| RNA-binding protein 3 OS = *Homo sapiens* GN = RBM3 PE = 1 SV = 1 | 17 kDa | 0 | 3 | 0 | 0 |
| rRNA 2'-O-methyltransferase fibrillarin OS = *Homo sapiens* GN = FBL PE = 1 SV = 2 | 34 kDa | 0 | 23 | 0 | 0 |
| Selenoprotein H OS = *Homo sapiens* GN = C11orf31 PE = 1 SV = 1 | 13 kDa | 0 | 2 | 0 | 0 |
| Semaphorin-3C OS = *Homo sapiens* GN = SEMA3C PE = 2 SV = 2 | 85 kDa | 0 | 3 | 0 | 0 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Serine protease 23 OS = *Homo sapiens* OX = 9606 GN = PRSS23 PE = 1 SV = 1 | 43 kDa | 0 | 7 | 7 | 5 |
| Serine protease HTRA3 OS = *Homo sapiens* OX = 9606 GN = HTRA3 PE = 1 SV = 2 | 49 kDa | 0 | 3 | 3 | 0 |
| Serine/threonine-protein phosphatase 2A catalytic subunit beta isoform OS = *Homo sapiens* GN = PPP2CB PE = 1 SV = 1 | 36 kDa | 0 | 4 | 0 | 0 |
| Serine/threonine-protein phosphatase PP1-beta catalytic subunit OS = *Homo sapiens* GN = PPP1CB PE = 1 SV = 3 | 37 kDa | 0 | 22 | 0 | 0 |
| Serpin B3 OS = *Homo sapiens* GN = SERPINB3PE = 1 SV = 2 | 45 kDa | 0 | 4 | 0 | 0 |
| SH3 domain-binding protein 1 OS = *Homo sapiens* GN = SH3BP1 PE = 1 SV = 3 | 76 kDa | 0 | 2 | 0 | 0 |
| Signal peptidase complex subunit 1 OS = *Homo sapiens* GN = SPCS1 PE = 1 SV = 4 | 12 kDa | 0 | 2 | 0 | 0 |
| Signal peptidase complex subunit 3 OS = *Homo sapiens* GN = SPCS3 PE = 1 SV = 1 | 20 kDa | 0 | 5 | 0 | 0 |
| Signal recognition particle 14 kDa protein OS = *Homo sapiens* GN = SRP14 PE = 1 SV = 2 | 15 kDa | 0 | 9 | 0 | 0 |
| Signal-induced proliferation-associated 1-like protein 2 OS = *Homo sapiens* OX = 9606 GN = SIPA1L2 PE = 1 SV = 2 | 190 kDa | 0 | 0 | 0 | 2 |
| Single-stranded DNA-binding protein, mitochondrial OS = *Homo sapiens* GN = SSBP1 PE = 1 SV = 1 | 17 kDa | 0 | 24 | 0 | 0 |
| SNW domain-containing protein 1 OS = *Homo sapiens* GN = SNW1 PE = 1 SV = 1 | 61 kDa | 0 | 4 | 0 | 0 |
| Solute carrier family 2, facilitated glucose transporter member 1 OS = *Homo sapiens* GN = SLC2A1 PE = 1 SV = 2 | 54 kDa | 0 | 9 | 0 | 0 |
| SPARC (Fragment) OS = *Homo sapiens* GN = SPARC PE = 1 SV = 1 | 17 kDa | 0 | 2 | 0 | 0 |
| Spermatogenesis-associated serine-rich protein 2 OS = *Homo sapiens* GN = SPATS2 PE = 1 SV = 1 | 60 kDa | 0 | 2 | 0 | 0 |
| Sphingosine-1-phosphate lyase 1 OS = *Homo sapiens* GN = SGPL1 PE = 1 SV = 3 | 64 kDa | 0 | 2 | 0 | 0 |
| Splicing factor 3B subunit 2 OS = *Homo sapiens* GN = SF3B2 PE = 1 SV = 1 | 98 kDa | 0 | 7 | 0 | 0 |
| SRA stem-loop-interacting RNA-binding protein, mitochondrial OS = *Homo sapiens* GN = SLIRP PE = 1 SV = 1 | 14 kDa | 0 | 2 | 0 | 0 |
| Structural maintenance of chromosomes protein 3 OS = *Homo sapiens* GN = SMC3 PE = 1 SV = 2 | 142 kDa | 0 | 11 | 0 | 0 |
| SWI/SNF-related matrix-associated actin-dependent regulator of chromatin subfamily A member 5 OS = *Homo sapiens* GN = SMARCA5 PE = 1 SV = 1 | 122 kDa | 0 | 17 | 0 | 0 |
| SWI/SNF-related matrix-associated actin-dependent regulator of chromatin subfamily E member 1 OS = *Homo sapiens* OX = 9606 GN = SMARCE1 PE = 1 SV = 2 | 47 kDa | 0 | 4 | 0 | 0 |
| SWISS-PROT: P01044-1 (Bos taurus) Isoform HMW of Kininogen-1 precursor | 69 kDa | 0 | 3 | 0 | 0 |
| SWISS-PROT: P02768-1 Tax_Id = 9606 Gene_Symbol = ALB Isoform 1 of Serum albumin precursor | 69 kDa | 0 | 0 | 5 | 13 |
| SWISS-PROT: Q3SZR3 (Bos taurus) Alpha-1-acid glycoprotein precursor | 23 kDa | 0 | 2 | 0 | 0 |
| SWISS-PROT: Q3TTY5 Tax_Id = 10090 Gene_Symbol = Krt2 Keratin, type II cytoskeletal 2 epidermal | 71 kDa | 0 | 27 | 7 | 7 |
| SWISS-PROT: Q9D312 Tax_Id = 10090 Gene_Symbol = Krt20 Keratin, type I cytoskeletal 20 | 49 kDa | 0 | 6 | 0 | 4 |
| SWISS-PROT: Q9QWL7 Tax_Id = 10090 Gene_Symbol = Krt17 Keratin, type I cytoskeletal 17 | 48 kDa | 0 | 54 | 0 | 16 |
| Synaptosomal-associated protein 23 OS = *Homo sapiens* GN = SNAP23 PE = 1 SV = 1 | 23 kDa | 0 | 6 | 0 | 0 |
| Tau-tubulin kinase 2 OS = *Homo sapiens* OX = 9606 GN = TTBK2 PE = 1 SV = 1 | 182 kDa | 0 | 0 | 0 | 0 |
| TBC1 domain family member 1 (Fragment) OS = *Homo sapiens* GN = TBC1D1 PE = 1 SV = 3 | 98 kDa | 0 | 2 | 0 | 0 |
| T-complex protein 1 subunit alpha OS = *Homo sapiens* GN = TCP1 PE = 1 SV = 1 | 60 kDa | 0 | 98 | 0 | 0 |
| Thyroid hormone receptor-associated protein 3 OS = *Homo sapiens* GN = THRAP3 PE = 1 SV = 2 | 109 kDa | 0 | 11 | 0 | 0 |
| Tight junction protein ZO-1 OS = *Homo sapiens* GN = TJP1 PE = 1 SV = 1 | 188 kDa | 0 | 3 | 0 | 0 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| Tight junction protein ZO-2 OS = *Homo sapiens* GN = TJP2 PE = 4 SV = 1 | 141 kDa | 0 | 3 | 0 | 0 |
| Transcription factor A, mitochondrial OS = *Homo sapiens* OX = 9606 GN = TFAM PE = 1 SV = 1 | 29 kDa | 0 | 14 | 1 | 1 |
| Transcription factor SOX-3 OS = *Homo sapiens* GN = SOX3 PE = 1 SV = 2 | 45 kDa | 0 | 2 | 0 | 0 |
| Transforming growth factor-beta-induced protein ig-h3 OS = *Homo sapiens* OX = 9606 GN = TGFBI PE = 1 SV = 1 | 75 kDa | 0 | 670 | 73 | 58 |
| Translocator protein OS = *Homo sapiens* OX = 9606 GN = TSPO PE = 1 SV = 3 | 19 kDa | 0 | 0 | 0 | 3 |
| Transmembrane protein 165 OS = *Homo sapiens* GN = TMEM165 PE = 1 SV = 1 | 35 kDa | 0 | 5 | 0 | 1 |
| TREMBL: Q0V8M9; Q9TRI0 (Bos taurus) similar to inter-alpha (globulin) inhibitor H3 isoform 2 | 100 kDa | 0 | 7 | 0 | 0 |
| TREMBL: Q2KJC7; Q8HZM3 (Bos taurus) Periostin, osteoblast specific factor | 87 kDa | 0 | 1 | 12 | 5 |
| TREMBL: Q3SZH5 (Bos taurus) Similar to Angiotensinogen | 45 kDa | 0 | 11 | 4 | 2 |
| TREMBL: Q3T052; Q5EA67 (Bos taurus) Inter-alpha (Globulin) inhibitor H4 | 102 kDa | 0 | 10 | 5 | 1 |
| TREMBL: Q6ISB0 Keratin, hair, basic, 4 - *Homo sapiens* (Human). | 65 kDa | 0 | 16 | 8 | 8 |
| TREMBL: Q6NXH9 Tax_Id = 10090 Gene_Symbol = Krt73 Keratin 73 | 59 kDa | 0 | 114 | 7 | 10 |
| TRIO and F-actin-binding protein OS = *Homo sapiens* OX = 9606 GN = TRIOBP PE = 1 SV = 3 | 261 kDa | 0 | 2 | 0 | 0 |
| Tropomodulin-3 OS = *Homo sapiens* OX = 9606 GN = TMOD3 PE = 1 SV = 1 | 40 kDa | 0 | 47 | 21 | 13 |
| Tropomyosin 1 (Alpha), isoform CRA_f OS = *Homo sapiens* GN = TPM1 PE = 1 SV = 1 | 37 kDa | 0 | 162 | 0 | 0 |
| Tropomyosin 1 (Alpha), isoform CRA_m OS = *Homo sapiens* GN = TPM1 PE = 1 SV = 1 | 29 kDa | 0 | 118 | 0 | 0 |
| Tropomyosin alpha-3 chain OS = *Homo sapiens* GN = TPM3 PE = 1 SV = 1 | 33 kDa | 0 | 112 | 0 | 0 |
| Tubby-related protein 2 (Fragment) OS = *Homo sapiens* OX = 9606 GN = TULP2 PE = 4 SV = 1 | 24 kDa | 0 | 0 | 0 | 2 |
| Twinfilin-1 OS = *Homo sapiens* OX = 9606 GN = TWF1 PE = 1 SV = 3 | 40 kDa | 0 | 1 | 1 | 4 |
| Tyrosine-protein kinase OS = *Homo sapiens* GN = YES1 PE = 1 SV = 1 | 61 kDa | 0 | 7 | 0 | 0 |
| Tyrosine--tRNA ligase OS = *Homo sapiens* GN = YARS PE = 1 SV = 1 | 44 kDa | 0 | 6 | 0 | 0 |
| U1 small nuclear ribonucleoprotein A (Fragment) OS = *Homo sapiens* GN = SNRPA PE = 1 SV = 1 | 28 kDa | 0 | 7 | 0 | 0 |
| U3 small nucleolar ribonucleoprotein protein MPP10 OS = *Homo sapiens* GN = MPHOSPH10 PE = 1 SV = 2 | 79 kDa | 0 | 6 | 0 | 0 |
| U3 small nucleolar RNA-associated protein 14 *Homo*log A OS = *Homo sapiens* OX = 9606 GN = UTP14A PE = 1 SV = 1 | 88 kDa | 0 | 2 | 0 | 0 |
| U4/U6.U5 tri-snRNP-associated protein 1 OS = *Homo sapiens* GN = SART1 PE = 1 SV = 1 | 90 kDa | 0 | 4 | 0 | 0 |
| UAP56-interacting factor OS = *Homo sapiens* OX = 9606 GN = FYTTD1 PE = 1 SV = 3 | 36 kDa | 0 | 3 | 0 | 0 |
| Ubiquitin carboxyl-terminal hydrolase 24 OS = *Homo sapiens* OX = 9606 GN = USP24 PE = 1 SV = 3 | 294 kDa | 0 | 0 | 0 | 2 |
| Unconventional myosin-Id OS = *Homo sapiens* OX = 9606 GN = MYO1D PE = 1 SV = 2 | 116 kDa | 0 | 0 | 2 | 0 |
| Unconventional myosin-VI OS = *Homo sapiens* GN = MYO6 PE = 1 SV = 1 | 145 kDa | 0 | 26 | 0 | 0 |
| Unconventional myosin-XV OS = *Homo sapiens* OX = 9606 GN = MYO15A PE = 1 SV = 2 | 395 kDa | 0 | 0 | 2 | 0 |
| Urokinase-type plasminogen activator OS = *Homo sapiens* GN = PLAU PE = 1 SV = 1 | 47 kDa | 0 | 8 | 0 | 0 |
| UV excision repair protein RAD23 homolog B OS = *Homo sapiens* GN = RAD23B PE = 1 SV = 1 | 43 kDa | 0 | 5 | 0 | 0 |
| Vacuolar protein sorting-associated protein 26A OS = *Homo sapiens* OX = 9606 GN = VPS26A PE = 1 SV = 2 | 38 kDa | 0 | 5 | 0 | 3 |
| Very-long-chain enoyl-CoA reductase OS = *Homo sapiens* GN = TECR PE = 1 SV = 1 | 36 kDa | 0 | 6 | 0 | 0 |
| Vesicle-trafficking protein SEC22b OS = *Homo sapiens* GN = SEC22B PE = 1 SV = 4 | 25 kDa | 0 | 6 | 0 | 0 |
| V-type proton ATPase subunit B, brain isoform OS = *Homo sapiens* GN = ATP6V1B2 PE = 1 SV = 3 | 57 kDa | 0 | 16 | 0 | 0 |

TABLE 2-continued

| Amniotic Fluid Cell-Derived ECM Components | | | | | |
|---|---|---|---|---|---|
| | | Total Spectra Count | | | |
| Protein | MW | Matrix A | Matrix B | Matrix C | Matrix D |
| V-type proton ATPase subunit d 1 OS = *Homo sapiens* GN = ATP6V0D1 PE = 1 SV = 1 | 45 kDa | 0 | 22 | 0 | 0 |
| Zinc finger protein 469 OS = *Homo sapiens* OX = 9606 GN = ZNF469 PE = 2 SV = 3 | 410 kDa | 0 | 0 | 0 | 4 |

C. Example 3—Proliferation of iPSCs on Amniotic Fluid Cell-Derived ECM

Induced pluripotent stem cells (iPSCs) were allowed to proliferate on an amniotic fluid cell-derived ECM (Matrix B) from Example 1 in culture using the following procedure: commercially available, cryopreserved iPSCs were thawed using a water bath at 37° C. Cell suspension was diluted into commercially available media for stem cell proliferation (Miltenyi Biotec MACS iPS Brew) and seeded onto the ECM at approximately 1,000 cells/cm$^2$ in a 6-well-plate with 2 mL of media/well. No Rock inhibitor was used. At day 1, the full volume of media was aspirated gently from cells in culture and replaced with fresh media. Every 24 hours, full media was replaced with fresh media. Once cells began to approach confluence (as determined by brightfield microscopy), cells were passage manually, using a sterile needle to cut large colonies into approximately 100 smaller colonies and then re-plate those by physically lifting them off the dish with the sterile needle and placing them on a fresh plate of the ECM. This procedure can be repeated indefinitely.

Figure 4:
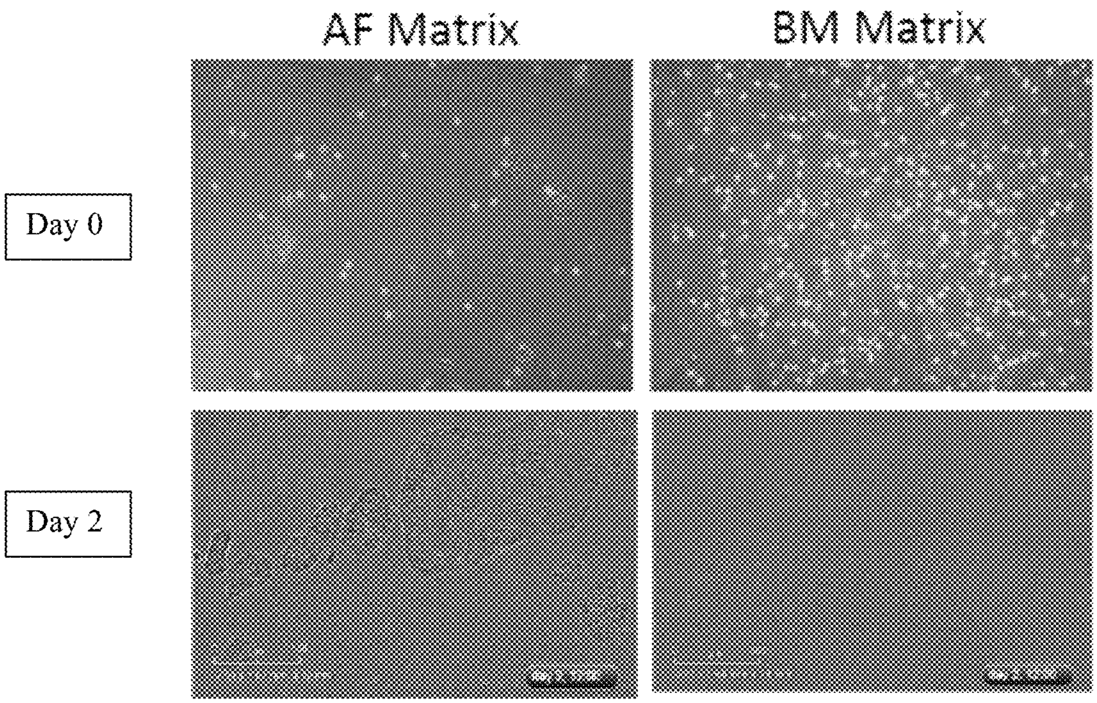
FIG. 4: a photomicrograph showing Day 0 and Day 2 culture of iPSCs on amniotic fluid cell-derived ECM and a bone marrow cell-derived ECM.

A photomicrograph showing Day 0 and Day 2 culture of iPSCs on amniotic fluid cell-derived ECM and a bone marrow cell-derived ECM is shown in FIG. 4.

Figure 5:
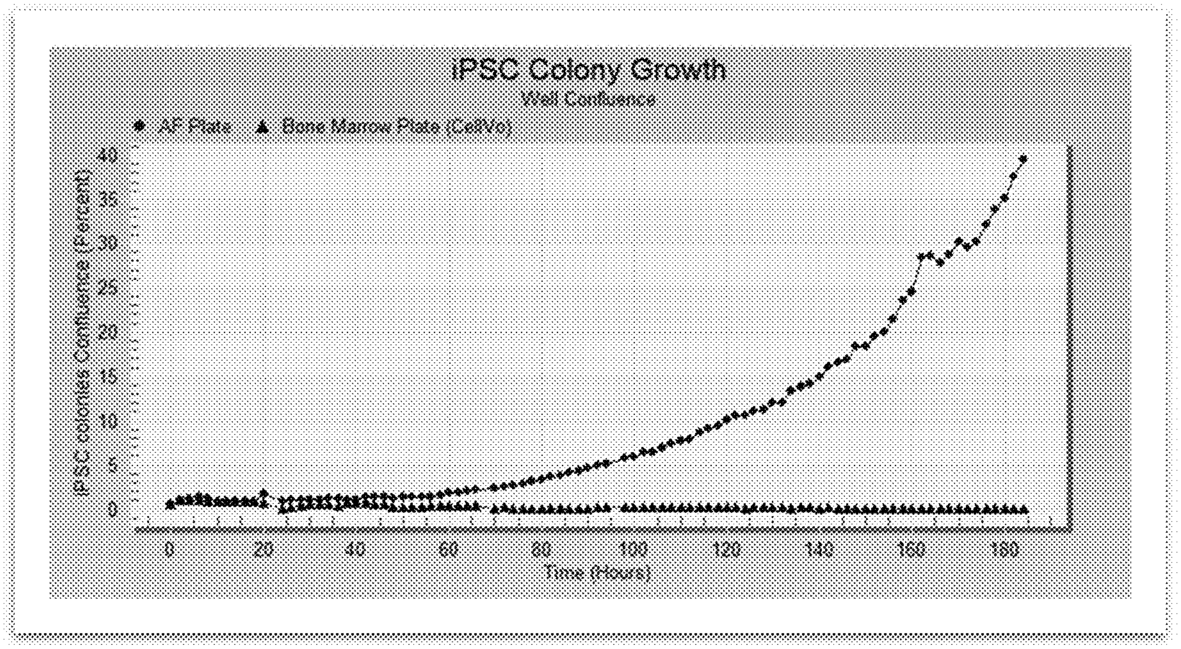
FIG. 5: a plot of growth curves of iPSCs cultured in the presence of the amniotic fluid cell-derived ECM and a bone marrow cell-derived ECM.

A plot of iPSC colony growth curves of iPSCs cultured in the presence of the amniotic fluid cell-derived ECM and a bone marrow cell-derived ECM is shown in FIG. 5.

As can be seen in FIG. 4 and FIG. 5, the iPSCs proliferated in culture in the presence of the amniotic fluid cell-derived ECM, whereas iPSCs cultured in the presence of a bone marrow cell-derived ECM had no growth.

Figure 6:
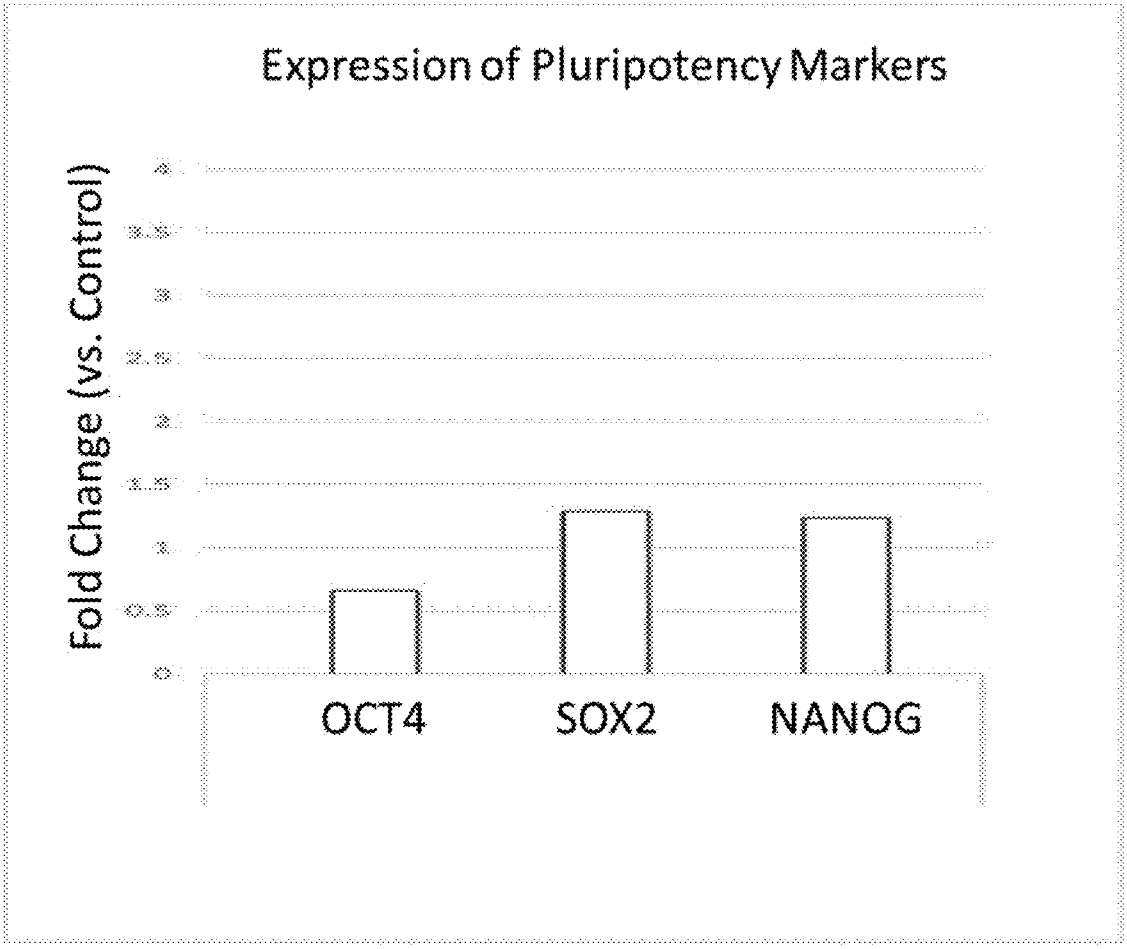
FIG. 6: a bar graph of pluripotent transcription factor expression in iPSCs cultured on amniotic fluid cell-derived ECM.

In another study, iPSCs were plated onto an amniotic fluid cell-derived ECM (AFC-ECM). Cells were passaged two times and then RNA was collected for gene expression analysis. Quantitative PCR was used to determine the gene expression. The iPSCs grown on the AFC-ECM maintained pluripotency during the course of the experiment and maintained expression of the core pluripotent transcription factors POU5F1 (OCT4), SOX2 and NANOG as shown in FIG. 6. The results from these studies suggest that the amniotic fluid cell-derived ECM supports pluripotent stem cell self-renewal and proliferation.

Figure 7:
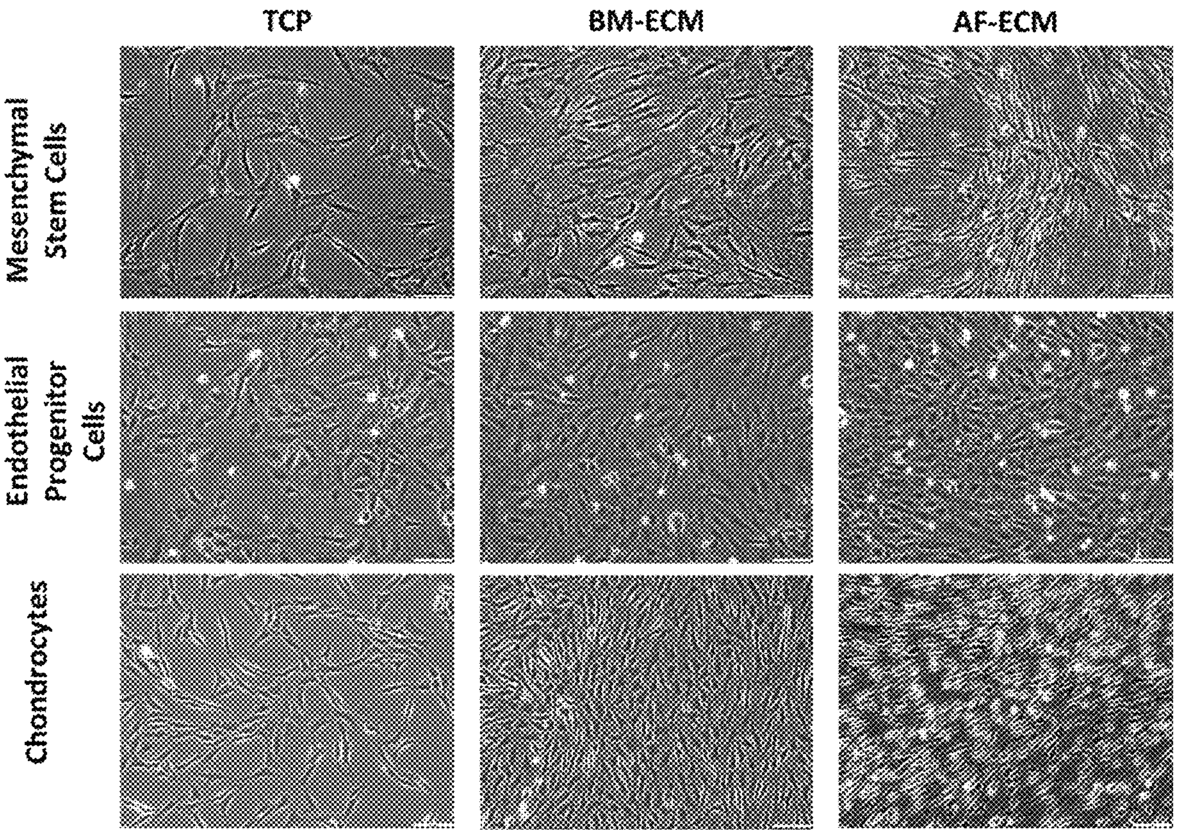
FIG. 7: photomicrographs of Brightfield Images of MSCs, EPCs, and Chondrocytes in culture on amniotic fluid cell-derived ECM vs. bone marrow ECM vs. tissue culture.
Figure 8A:
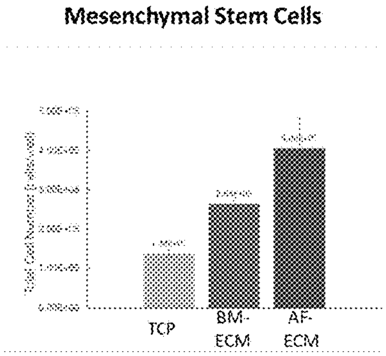
FIG. 8A: a bar graph quantifying the proliferation of MSCs in culture after 4 days on amniotic fluid cell-derived ECM.
Figure 8B:
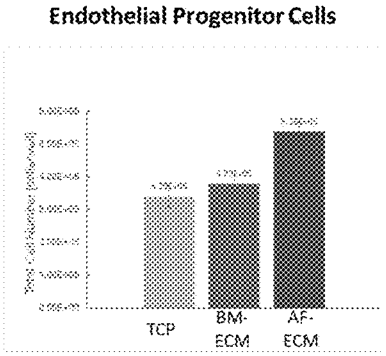
FIG. 8B: a bar graph quantifying the proliferation of EPCs in culture after 4 days on amniotic fluid cell-derived ECM.
Figure 8C:
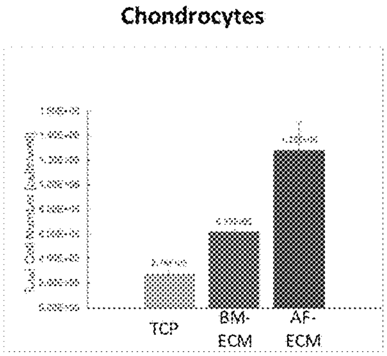
FIG. 8C: a bar graph quantifying the proliferation of chondrocytes in culture after 4 days on amniotic fluid cell-derived ECM.
Figure 9:
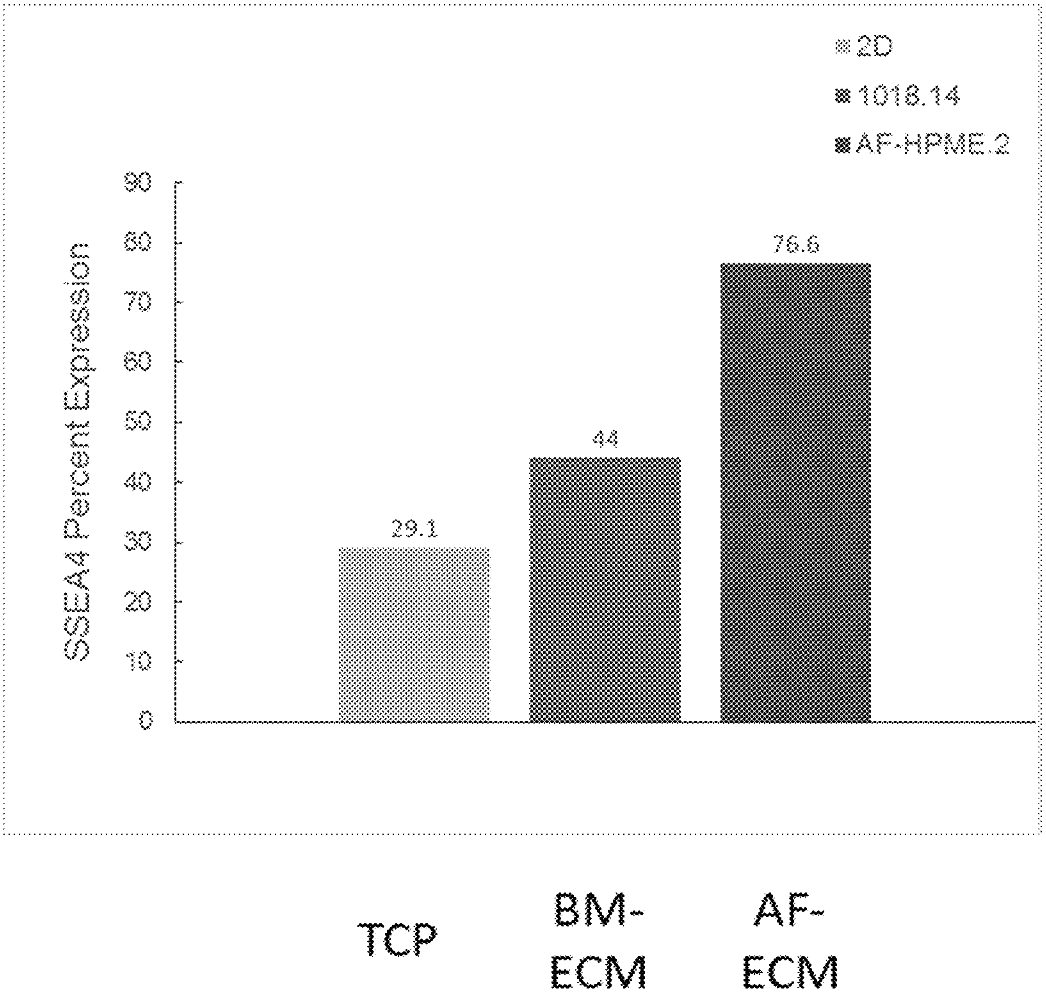
FIG. 9: a bar graph of the percentage of MSCs expressing SSEA-4 as measured by flow cytometry following culture on amniotic fluid cell-derived ECM vs. bone marrow cell ECM vs. tissue culture plastic for four days

D. Example 4—Proliferation of Various Cell Types on Amniotic Fluid Cell-Derived ECM Mesenchymal stem cells (MSCs) obtained from bone marrow, endothelial progenitor cells (EPCs), and chondrocytes were seeded onto amniotic fluid cell-derived ECM (AF-ECM), bone marrow cell-derived ECM (BM-ECM), and tissue culture plastic (TCP) at equal seeding density in standard commercially available media. For MSCs and chondrocytes the media was alpha minimum essential media (aMEM) modified without phenol red, supplemented with 15% by volume fetal bovine serum, 1% antibiotic-antimycotic (anti-anti), and 1% GlutaMax. For EPCs, the media was Iscove's Modified Dulbecco's Medium (IMDM) Supplemented with 20% FBS, 1% anti-anti, 1% GlutaMax, and growth factors (EGF and FGF). Photomicrographs showing increased proliferation on the two ECMs relative to TCP are shown in FIG. 7. The proliferation of the cells after 4 days of culture is quantified in the bar graphs in FIG. 8*a*, FIG. 8*b*, and FIG. 8*c*. Surprisingly, the amniotic fluid cell-derived ECM supports increased proliferation of the MSCs (produced by bone marrow) relative to the bone marrow cell-derived ECM. Additionally, FIG. 9 shows the percentage of MSCs expressing SSEA-4 as measured by flow cytometry after 4 days of culture on each substrate. SSEA-4 expression is elevated after culture on amniotic fluid cell-derived ECM relative to the other substrates.

E. Example 5—Differentiation of MSCs Cultured on Amniotic Fluid Cell-Derived ECM Mesenchymal stem cells (MSCs) obtained from human bone marrow were seeded on amniotic fluid cell-derived ECM (AFC-ECM) at $6\times10^3$ cells/cm$^2$ and cultured for 14 days in growth media.

Figure 10:
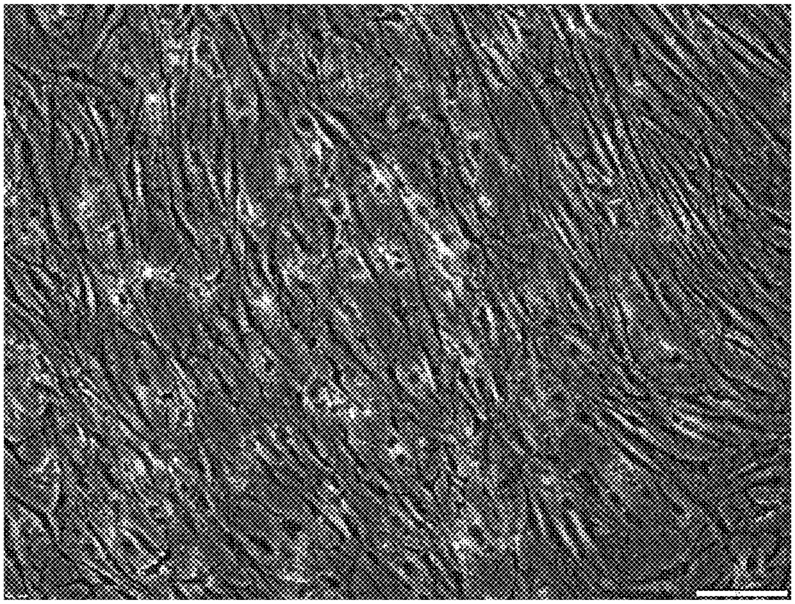
FIG. 10: a photomicrograph of adipogenic differentiation of MSCs cultured on amniotic fluid cell-derived matrix for four days.

To assess the adipogenic differentiation efficiency of the cells, cultures were transferred at Day 7 to adipogenic media (DMEM containing 10% FBS, 0.5 mM IBMX, $10^{-6}$ M dexamethasone, 10 μM insulin, and 200 μM indomethacin), maintained for an additional 10 days, fixed with 10% formalin for 1 hour at room temperature, and then stained with Oil Red O. Adipogenesis is verified by staining the differentiated cells with the Oil Red O. The Oil Red O stains the lipid droplets (red staining) formed within the cells following the differentiation of the MSCs to adipocytes in culture. Photomicrographs showing adipogenic differentiation of the MSCs on the AFC-ECM is shown in FIG. 10.

Figure 11:
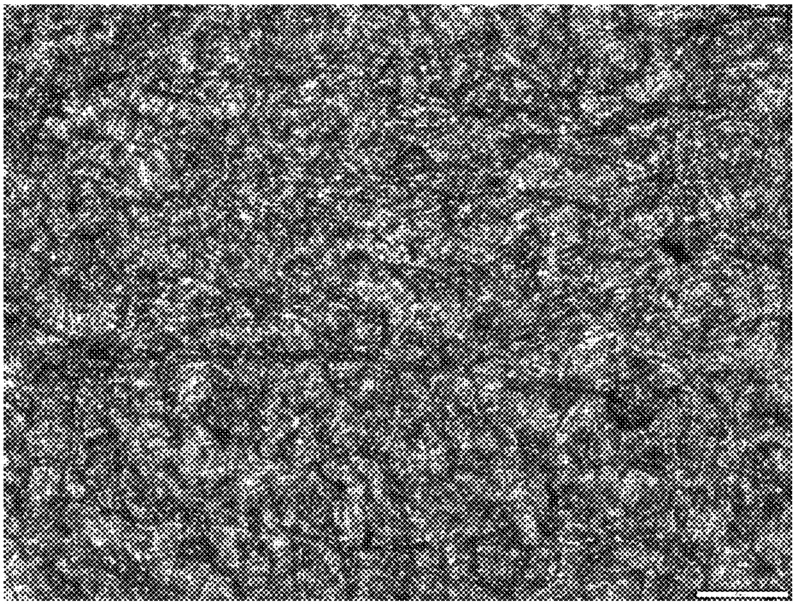
FIG. 11: a photomicrograph of osteogenic differentiation of MSCs cultured on amniotic fluid cell-derived matrix for four days.

To assess osteogenic differentiation efficiency, the cultures were transferred to osteoblast differentiation media (growth media supplemented with $10^{-7}$M dexamethasone (Sigma-Aldrich, St. Louis, MO) and $10^{-4}$M L-ascorbate-2-phosphate (Wako Chemicals, Richmond, VA), maintained an additional 25 days, fixed with 10% formalin for 1 hour at room temperature, and then stained with 1% Silver Nitrate (Von Kossa Staining). Osteogenesis is verified by staining the differentiated cells with 1% Silver Nitrate. The Silver Nitrate stains the minerals (dark staining) deposited following the differentiation of the MSCs to osteoblasts in culture. Photomicrographs showing osteogenic differentiation of the MSCs on the AFC-ECM is shown in FIG. 11. This study demonstrates that stem cells can be induced to differentiate into differentiated cell types in culture on an amniotic fluid cell-derived ECM.

The invention claimed is:

1. A cell-derived extracellular matrix (ECM) derived in vitro from isolated and culturally expanded cells from amniotic fluid, wherein the cells comprise fetal cells from amnion membrane, skin, and alimentary, respiratory, and urogenital tracts, wherein the amniotic fluid is obtained from a human at greater than 37 weeks of gestational age, and wherein the cell-derived ECM is in contact with somatic cells, progenitor cells, stem cells, chondrocytes, or osteoblasts.

2. The cell-derived ECM of claim 1, wherein the ECM comprises laminin, collagen alpha-1 (XVIII), basement membrane-specific heparan sulfate proteoglycan core protein, agrin, vimentin, and collagen alpha-2 (IV), or isoforms thereof.

3. The cell-derived ECM of claim 2, wherein the isoform of collagen alpha-1 (XVIII) is isoform 2.

4. The cell derived ECM of claim 1, wherein the cell-derived ECM further comprises fibronectin or an isoform thereof.

5. The cell-derived ECM of claim 1, wherein the cell-derived ECM does not contain decorin, perlecan, and collagen (III).

6. The cell-derived ECM of claim 1, wherein the cell-derived ECM is decellularized.

7. The cell-derived ECM of claim 1, wherein the cell-derived ECM is comprised in a container.

8. The cell-derived ECM of claim 7, wherein the container is a flask, a fermenter, a bioreactor, a rocking bottle, or a tube.

9. The cell-derived ECM of claim 8, wherein the container is a flask, and wherein the flask is a cell culture flask, a T-flask, a stirred flask, a spinner flask, or a shaking flask.

10. The cell-derived ECM of claim 8, wherein the container is a bioreactor.

11. The cell-derived ECM of claim 1, wherein the cells in contact with the cell-derived ECM are mammalian cells.

12. The cell-derived ECM of claim 1, wherein the stem cells are pluripotent stem cells (PSCs) or mesenchymal stem cells (MSCs).

13. The cell-derived ECM of claim 12, wherein the stem cells are PSCs, and wherein the PSCs are induced PSCs.

14. A method of proliferating cells in culture, the method comprising culturing the cells in the presence of the cell-derived extracellular matrix (ECM) of claim 1 in a culture media thereby proliferating the cells.

15. A method of inducing differentiation of stem cells into differentiated cell types, the method comprising culturing the stem cells in the presence of the cell-derived extracellular matrix (ECM) of claim 1 in a differentiation media thereby differentiating the stem cells.

16. The cell-derived ECM of claim 1, wherein the cell-derived ECM includes ECM proteins from ectoderm, mesoderm, and endoderm.

* * * * *